US005543417A

United States Patent [19]
Waldstreicher

[11] Patent Number: 5,543,417
[45] Date of Patent: Aug. 6, 1996

[54] COMBINATION METHOD OF TREATING ACNE USING 4-AZA-5α-CHOLESTAN-ONES AND 4-AZA-5α-ANDROSTAN-ONES AS SELECTIVE 5α-REDUCTASE INHIBITORS WITH ANTI-BACTERIAL, KERATOLYTIC, OR ANTI-INFLAMMATORY AGENTS

[75] Inventor: Joanne Waldstreicher, Scotch Plains, N.J.

[73] Assignee: Merck & Co., Inc., Rahway, N.J.

[21] Appl. No.: 327,078

[22] Filed: Oct. 21, 1994

[51] Int. Cl.$^6$ .................................................. A01N 43/42
[52] U.S. Cl. ............................................................. 514/284
[58] Field of Search ............................................. 514/284

[56] References Cited

U.S. PATENT DOCUMENTS

| | | |
|---|---|---|
| 2,227,876 | 1/1941 | Bolt . |
| 3,239,417 | 3/1966 | Ditullio et al. . |
| 3,264,301 | 8/1966 | Doorenbos et al. . |
| 3,285,918 | 11/1966 | Doorenbos et al. . |
| 4,220,775 | 9/1980 | Rasmusson et al. . |
| 4,377,584 | 3/1983 | Rasmusson et al. . |
| 4,732,897 | 3/1988 | Cainelli et al. . |
| 4,760,071 | 7/1988 | Rasmusson et al. . |
| 4,845,104 | 7/1989 | Carlin et al. . |
| 4,859,681 | 8/1989 | Rasmusson et al. . |
| 5,120,840 | 6/1992 | Weintraub et al. . |
| 5,130,424 | 7/1992 | Weintraub . |
| 5,143,909 | 9/1992 | Weintraub et al. . |
| 5,155,107 | 10/1992 | Panzeri et al. . |
| 5,215,894 | 6/1993 | Arison ........................................ 435/53 |

FOREIGN PATENT DOCUMENTS

| | | |
|---|---|---|
| 0435321A2 | 7/1991 | European Pat. Off. . |
| 0484094A2 | 5/1992 | European Pat. Off. . |
| 0511477A1 | 11/1992 | European Pat. Off. . |
| 0519353A2 | 12/1992 | European Pat. Off. . |
| 0532190A2 | 3/1993 | European Pat. Off. . |
| 0538192A1 | 4/1993 | European Pat. Off. . |
| 0579223A1 | 1/1994 | European Pat. Off. . |
| WO91/13550 | 9/1991 | WIPO . |
| WO92/13828 | 8/1992 | WIPO . |
| WO92/20700 | 11/1992 | WIPO . |
| WO93/02050 | 2/1993 | WIPO . |
| WO93/05019 | 3/1993 | WIPO . |
| WO93/13124 | 7/1993 | WIPO . |
| WO93/16996 | 9/1993 | WIPO . |
| WO93/19758 | 10/1993 | WIPO . |
| WO93/24442 | 12/1993 | WIPO . |
| WO94/00121 | 1/1994 | WIPO . |
| WO94/00125 | 1/1994 | WIPO . |
| WO94/03476 | 2/1994 | WIPO . |
| WO94/03475 | 2/1994 | WIPO . |
| WO94/03474 | 2/1994 | WIPO . |
| WO94/07909 | 4/1994 | WIPO . |
| WO94/11386 | 5/1994 | WIPO . |
| WO94/11385 | 5/1994 | WIPO . |
| WO94/14833 | 7/1994 | WIPO . |

OTHER PUBLICATIONS

"Synthesis and Antimicrobial Properties of 17β-Isopentyloxy-4-aza-5α-androstane and the 4-Methyl Derivative", Norman J. Doorenbos and William E. Solomons, Journal of Pharmaceutical Sciences, vol., 62, No. 4, 1973, pp. 638–640.

"4,17 α-Dimethyl-4-aza-5α-androstan-17β-ol Acetate and Related Azasteroids", Norman J. Doorenbos and Sister Jane Marie Brown, Journal of Pharmaceutical Sciences, vol. 60, No. 8, 1971, pp. 1234–1235.

"Synthesis and Evaluation of Antimicrobial Properties of Amidinoazaandrostanes and Guanidinoazaandrostanes", Norman J. Doorenbos and Jack C. Kim, Journal of Pharmaceutical Sciences, vol. 63, No. 4, 1974, pp. 620–622.

"Azasteroids as Inhibitors of Rat Prostatic 5α–Reductase", Gary H. Rasmusson, et al., Journal of Medicinal Chemistry, vol. 27, 1984, pp. 1690–1701.

"Azasteroids: Structure–Activity Relationships for Inhibition of 5α–Reductase and of Androgen Receptor Binding", Gary H. Rasmusson, et al., Journal of Medicinal Chemistry, vol. 29, 1986, pp. 2298–2315.

"Kinetic Parameters of 5α–Reductase Activity in Stroma and Epithelium of Normal, Hyperplastic, and Carcinomatous Human Prostates", Nicholas Bruchovsky, et al., Journal of Clincal Endocrinology and Metabolism, vol. 67, No. 4, 1988, pp. 806–816.

"Comparison of Nuclear 5α–Reductase Activities in the Stromal and Epithelial Fractions of Human Prostatic Tissue", Robert W. Hudson, Journal of Steroid Biochemistry, vol. 26, No. 3, 1987, pp. 349–353.

"Steroid 5α–Reductase in Cultured Human Fibroblasts––Biochemical and Genetic Evidence for Two Distinct Enzyme Activities", Ronald J. Moore and Jean D. Wilson, The Journal of Biological Chemistry, vol. 254, No. 19, 1976, pp. 5895–5900.

"Expression Cloning and Regulation of Steroid 5α–Reductase, an Enzyme Essential for Male Sexual Differentiation", Stefan Andersson, et al., The Journal of Biological Chemistry, vol. 264, No. 27, 1989, pp. 16249–16255.

"Structural and biochemical properties of cloned and expressed human and rat steroid 5α–reductases", Stefan Andersson, et al., Proceedings of the National Academy of Sciences, USA, vol. 87, 1990, pp. 3640–3644.

"Deletion of steroid 5 α–reductase 2 gene in male pseudohermaphroditism", Stefan Andersson, et al., Nature, vol. 354, 1991, pp. 159–161.

"Syndromes of Androgen Resistance", Jean D. Wilson, Biology of Reproduction, vol. 46, 1992, pp. 168–173.

"Indentification and selective inhibition of an isozyme of steroid 5α–reductase in human scalp", Georgianna Harris, et al., Proceedngs of the National Academy of Sciences, USA, vol. 89, 1992, pp. 10787–10791.

Primary Examiner—Paul J. Killos
Attorney, Agent, or Firm—Catherine D. Fitch; Robert J. North; Melvin Winokur

[57] ABSTRACT

Described is a combination method using selective inhibitors of 5α-reductase 1 and/or 2 including 7β-substituted 4-aza-5α-cholestan-3-ones and related 4-aza-5α-androstan-3-one compounds which are useful in the treatment of acne vulgaris in combination with at least one agent selected from an antibacterial, keratolytic, and/or an anti-inflammatory.

31 Claims, No Drawings

COMBINATION METHOD OF TREATING ACNE USING 4-AZA-5α-CHOLESTAN-ONES AND 4-AZA-5α-ANDROSTAN-ONES AS SELECTIVE 5α-REDUCTASE INHIBITORS WITH ANTI-BACTERIAL, KERATOLYTIC, OR ANTI-INFLAMMATORY AGENTS

BACKGROUND OF THE INVENTION

The present invention is directed to a combination method for treating ache using selective 5α-reductase 1 inhibitors, 5α-reductase 2 inhibitors, combinations thereof, or dual inhibitors, including but not limited to: 7β-substituted-4-aza-5α-cholestan-3-ones and related 4-aza-5α-androstan-3-one compounds, together with at least one agent selected from an antibacterial, a keratolytic, an anti-inflammatory agent, or mixture thereof.

DESCRIPTION OF THE PRIOR ART

Acne vulgaris is the most common skin condition evaluated and managed by physicians in the United States. It is estimated that more than 17 million people have some degree of acne. While it is most prevalent in adolescents, nearly 85% of 12–24 year olds, 8% of 25–34 year olds, and 3% of 35–55 year olds have acne. In 1990, nearly 4.5 million patient visits to dermatologists were for acne-related problems; an additional 500,000 visits were to primary care providers.

Acne is basically an androgen dependent disorder. Its peak incidence is at age 18, and it is more prevalent in men than in women. In some cases, it can be severe enough to cause significant scarring that does not resolve. In many patients, its presence is psychologically distressing. While it is not a life-threatening condition, it can have significant psychosocial effects on those who suffer with it. Acne has also been shown to be associated with impaired academic and social functioning, as well as to affect employment status. Thus, the accurate assessment and appropriate management of acne can have important consequences on the overall well-being and quality of life of the patient with acne.

Sebum is one of the major factors, along with abnormal keratinization of the follicular epithelium, intimation and colonization by the bacterium *P. acnes*, that causes acne. Since all of these factors are inter-related, affecting just one, e.g., sebum production, can have a profound influence on acne.

The hormonal milieu plays an important role in modulating sebum production in males and females. In children, onset of acne and sebum secretion occur coincident with the increasing androgens that accompany adrenarche and pubarche. Administration of androgens worsens acne and increases sebum production, while admininstration of estrogens decreases sebum production and is associated with an improvement in acne. Antiandrogens, such as cyproterone and spironolactone, are sometimes used for the treatment of acne in women. Although these clinical observations provided convincing evidence that androgens modulate sebum production, it had been uncertain which of the androgens plays the most important role.

It is now known in the an that the principal mediator of androgenic activity in some target organs is 5α-dihydrotestosterone (DHT), and that it is formed locally in the target organ by the action of testosterone-5α-reductase. It is also known that inhibitors of testosterone-5α-reductase will serve to prevent or lessen symptoms of hyperandrogenic stimulation.

A number of 4-aza steroid compounds are known in the art. For example, See U.S. Pat. Nos. 2,227,876, 3,239,417, 3,264,301 and 3,285,918; French Patent No. 1,465,544; Doorenbos and Solomons, *J. Pharm. Sci.*, 62, 4, pp. 638–640 (1973); Doorenbos and Brown, *J. Pharm. Sci.*, 60, 8, pp. 1234–1235 (1971); and Doorenbos and Kim, *J. Pharm. Sci.*, 63, 4, pp. 620–622 (1974).

In addition, U.S. Pat. Nos. 4,377,584, 4,220,775, 4,859,681, 4,760,071 and the articles "J. Med. Chem." 27, p. 1690–1701 (1984) and "J. Med. Chem." 29, 2998–2315 (1986) of Rasmusson, et at., U.S. Pat. No. 4,845,104 to Carlin, et at., and U.S. Pat. No. 4,732,897 to Cainelli, et al. describe 4-aza-17β-substituted-5α-androstan-3-ones which are said to be useful in the treatment of DHT-related hyperandrogenic conditions.

However, despite the suggestion in the prior art that hyperandrogenetic diseases are the result of a single 5α-reductase, there are reports regarding the presence of other 5α-reductase isozymes in both rats and humans. For example, in human prostate, Bruchovsky, et al. (See *J. Clin. Endocrinol. Metab.* 67, 806–816, 1988) and Hudson (see *J. Steroid Biochem.* 26, p 349–353, 1987) found different 5α-reductase activities in the stromal and epithelial fractions. Additionally, Moore and Wilson described two distinct human reductases with peaks of activities at either pH 5.5 or pH 7–9. (See *J. Biol. Chem.* 251, 19, p. 5895–5900, 1976).

Recently, Andersson and Russell isolated a cDNA which encodes a rat liver 5α-reductase (see *J. Biol. Chem.* 264 pp. 16249–55 (1989). They found a single mRNA which encodes both the liver and prostatic reductases of rats. The sequence of this rat gene was later used to select a human prostatic cDNA encoding a 5α-reductase termed "5α-reductase 1". (See *Proc. Nat'l. Acad. Sci.* 87, p. 3640–3644, 1990).

More recently, a second, human prostatic reductase (5α-reductase 2) has been cloned with properties identified with the more abundant form found in crude human prostatic extracts. (See *Nature*, 354, p. 159–161, 1991).

Further, "Syndromes of Androgen Resistance"—The Biology of Reproduction, Vol. 46, p. 168–173 (1992) by Jean O. Wilson indicates that the 5α-reductase 1 enzyme may be associated with hair follicles.

Thus, the art supports the existence of at least two genes for 5α-reductase and two distinct isozymes of 5α-reductase in humans. The isozyme that principally interacts in certain skin tissues, e.g., skin or scalp, is conventionally designated as 5α-reductase 1 (or 5α-reductase type 1), while the isozyme that principally interacts within the prostatic tissues is designated as 5α-reductase 2 (or 5α-reductase type 2). See, e.g., G. Harris, et at., *Proc. Natl. Acad. Sci. USA*, Vol. 89, pp. 10787–10791 (November 1992).

Local dihydrotesterone (DHT) formation via 5 alpha reductase (5 alphaR) plays a major role in sebum production and the pathophysiology of acne since it is known that the sebaceous gland is rich in 5 alpha reductase and that acne prone skin contains excessive 5 alphaR activity. On this basis, local DHT formation is responsible for increased sebum production in sebaceous follicles of acne prone tissue and 5 alpha $R^1$ or $R^2$ inhibition, or combination thereof, can be useful in the treatment of acne.

As described above, acne is a disease with multifactorial pathogenesis including the factors of: (a) increased sebum production, (b) follicular keratinization, (c) *Propionibacterium acnes* proliferation and (d) inflammation. On this basis, we believe that its effective management can best be brought about through combination therapy that concurrently addresses more than one of these pathogenic factors in a therapeutic protocol. In the treatment of acne vulgaris, it would be desirable to employ a 5α-reductase 1 or 2 inhibitor, combination thereof, or a dual inhibitor, which decreases sebum production, in combination with another agent to amplify the therapy against the other above-described pathogenic factors in the treatment.

Therefore it is an object of this invention to provide a combination method of agents that has sufficient activity in the inhibition of 5α-reductase isozyme 1,5α-reductase isozyme 2, combination thereof, or the use of a dual inhibitor, in combination with another agent that will enhance the effectiveness of the 5α-reductase 1 or 2 inhibitor, or combination thereof, in the treatment of acne vulgaris.

SUMMARY OF THE INVENTION

By this invention there is provided a combination method involving the use of a 5α-reductase 1 and/or 2 inhibitor, in combination with at least one agent selected from: an antibacterial, an anti-inflammatory, and a keratolytic, or combination thereof, in the treatment of acne vulgaris by topical and/or systemic administration.

The 5 alpha reductase 1 or 2 inhibitor inhibits the production of sebum while concurrently: the antibacterial improves both inflammatory and non-inflammatory lesions by reducing the population of *Propionibacterium acnes* and other Gram-negative and Gram-positive bacteria on the skin surface and within the follicles; the keratolytic, decreases follicular keratinization; and the anti-inflammatory decreases intimation and can lead to a mild drying and peeling of the skin. This combination of agents leads to a more effective method of treatment than use of either agent alone.

The invention is still further concerned with pharmaceutical formulations comprising one or more inhibitors of 5α-reductase 1 or 2, or combination thereof, or a dual inhibitor, in combination with at least one agent selected from an antibacterial, a keratolytic, and an anti-inflammatory, or combination thereof.

In one embodiment of this invention, is a method of treating acne employing 5α-reductase 1 inhibitors, i.e., 7β-substituted-4-aza-5α-cholestan-3-ones and 5α-androstan-3-one compounds, which are selected from the group consisting of the generic Formulae (I.):

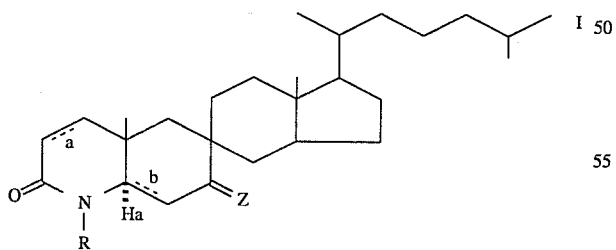

or a pharmaceutically acceptable salt or ester thereof, wherein for Structure I:

R is selected from hydrogen, methyl, ethyl, —OH, —NH₂, and —SCH₃; the dashed lines "- - -" a and b independently represent a single bond or a double bond providing that when b is a double bond, the 5α hydrogen, Ha, is absent;

=Z is selected from:

1) oxo,
2) α-hydrogen and a β-substituent selected from:
   a) $C_1$-$C_4$ alkyl,
   b) $C_2$-$C_4$ alkenyl,
   c) $CH_2COOH$,
   d) —OH,
   e) —COOH,
   f) —COO($C_1$-$C_4$ alkyl),
   g) —OCONR$^1$R$^2$ wherein R$^1$ and R$^2$ independently are selected from:
      i) H,
      ii) $C_1$-$C_4$ alkyl,
      iii) phenyl, and
      iv) benzyl, or
      R$^1$ and R$^2$ together with the nitrogen atom to which they are attached represent a 5–6 membered saturated heterocycle, optionally containing one other heteroatom selected from —O—, —S— and —N(R')— wherein R' is —H or methyl;
   h) $C_1$-$C_4$ alkoxy,
   i) $C_3$-$C_6$ cycloalkoxy,
   j) —OC(O)-$C_{1-4}$ alkyl
   k) halo,
   l) hydroxy-$C_1$-$C_2$ alkyl,
   m) halo-$C_1$-$C_2$ alkyl,
   n) —CF₃, and
   o) $C_3$-$C_6$ cycloalkyl;
3) =CR$^3$; wherein R$^3$ is selected from —H and $C_1$-$C_4$ alkyl; and
4) spirocyclopropane-R$^3$ of structure:

and

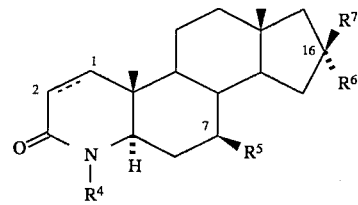

or a pharmaceutically acceptable salt or ester thereof wherein:

the $C_1$-$C_2$ carbon-carbon bond may be a single bond, or a double bond as indicated by the dashed line;

R$^4$ is selected from the group consisting of hydrogen and $C_{1-10}$ alkyl;

R$^5$ is selected from the group consisting of hydrogen and $C_{1-10}$ alkyl;

one of R$^6$ and R$^7$ is selected from the group consisting of hydrogen and methyl, and the other is selected from the group consisting of:
(a) amino;
(b) cyano;
(c) fluoro;
(d) methyl;
(e) OH;
(f) —C(O)NR$_b$R$_c$, where R$_b$ and R$_c$ are independently H, $C_{1-6}$ alkyl, aryl, or aryl$C_{1-6}$ alkyl; wherein the alkyl moiety can be substituted with 1–3 of: halo; $C_{1-4}$ alkoxy; or trifluoromethyl; and the aryl moiety can be substituted with 1–3 of: halo; $C_{1-4}$alkyl; $C_{1-4}$ alkoxy; or trifluoromethyl;

(g) $C_{1-10}$ alkyl-X—;

(h) $C_{2-10}$ alkenyl-X—; wherein the $C_{1-10}$ alkyl in (g) and $C_{2-10}$ alkenyl in (h) can be unsubstituted or substituted with one to three of:

i) halo; hydroxy; cyano; nitro; mono-, di- or trihalomethyl; oxo; hydroxysulfonyl; carboxy;

ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;

iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;

iv) —C(O)NR$_b$R$_c$; —N(R$_b$)—C(O)—R$_c$; —NR$_b$R$_c$; where R$_b$ and R$_c$ are defined above;

(i) aryl-X—;

(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring; wherein the aryl in (i) and heteroaryl in (j) can be unsubstituted or substituted with one to three of:

v) halo; hydroxy;cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxy-carbonyl; $C_{1-6}$ alkyloxycarbonyl $C_{1-6}$alkyl; R$_b$R$_c$N—C(O)-$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$ alkoxy; or trifluoromethyl;

viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is $C_{1-6}$alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$alkyl; $C_{1-4}$ alkoxy, or trifluoromethyl; —N(R$_b$)—C(O)NR$_c$R$_d$, wherein R$_d$ is selected from H, $C_{1-6}$ alkyl, and aryl; in which said $C_{1-6}$alkyl and aryl can be substituted as described above in (f) for R$_b$ and R$_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and (k) $R^6$ and $R^7$ taken together can be carbonyl oxygen;

(l) $R^6$ and $R^7$ taken together can be =CH—R$_g$, wherein R$_g$ is defined in viii); and wherein:

X is selected from the group consisting of: —O—; —S(O)$_n$—; —C(O)—; —CH(R$_e$)—; —C(O)—O—*; —C(O)—N(R$_e$)—*; —N(R$_e$)—C(O)—O—*; —O—C(O)—N(R$_e$)—*; —N(R$_e$)C(O)—N(R$_e$)—; —O—CH(R$_e$)—*; —N(R$_e$)—; wherein R$_e$ is H, $C_{1-3}$ alkyl, aryl, aryl-$C_{1-3}$ alkyl, or unsubstituted or substituted heteroaryl, as defined above in (j);

wherein the asterisk (*) denotes the bond which is attached to the 16-position in Structure II; and n is zero, 1 or 2.

DETAILED DESCRIPTION OF THE INVENTION

The present invention has the objective of providing a combination method of treating the hyperandrogenic conditions of acne, which can be comedonal, papulopustular, nodular or cystic, including acne vulgaris, seborrhea, neonatal acne, infantile acne, adolescent acne, adult acne, postmenopausal acne, acne conglobata, hidradenitis suppurativa, acne mechanica, perioral dermatitis, acne fulminans, pyoderma faciale, acne excoriée des jeunes filles, acne tropicalis, acne estivalis, Favre-Racouchot Syndrome, or acne venenata. The method involves the oral, systemic, parenteral or topical administration of a therapeutically effective amount of one or more 5 alpha reductase 1 inhibitor compounds of Formula I or II, or a 5α-reductase 2 inhibitor, or combination thereof, or a dual inhibitor, in combination with at least one agent selected from an antibacterial, a keratolytic, an anti-inflammatory, or mixture thereof.

By the term "5α-reductase 1 inhibitor" as used herein, is meant a compound which selectively interferes with the physiological action of the enzyme 5α-reductase 1 on human tissue. An example is 4,7β-dimethyl-4-aza-5α-cholestan-3-one, and related analogues, described herein.

By the term "5α-reductase 2 inhibitor" as used herein, is meant a compound which selectively interferes with the physiological action of the enzyme 5α-reductase 2 on human tissue. An example is finasteride, described in U.S. Pat. No. 4,760,071 (to Merck & Co., Inc.) and related analogues.

By the term "dual 5α-reductase 1 and 2 inhibitor" as used herein, is meant a compound which interferes with the physiological action of the enzymes, 5α-reductase 1 and 5α-reductase 2, on human tissue. Examples of these type of compounds are the 6-azaandrost-4-en-3-ones, described in "J. Med Chem.", 1993, Vol 36, pages 4313–4315, and related analogues, and aryl esters in U.S. Pat. No. 5,278,159.

In the treatment of acne, as described herein, the above described 5α-reductase can be used individually or in combination with one or more of the others.

DISCUSSION OF FORMULA I (STRUCTURE I)

The 17-substituent cholestane side chain in Formula I is in the beta configuration. Combinations of substituents and/or variables are permissible only if such combinations result in stable compounds.

The term "$C_1$–$C_4$ alkyl" as used herein, is meant to include methyl (Me), ethyl (Et), propyl (Pr), iso-propyl (i-Pr), n-butyl (n-Bu), sec-butyl (s-Bu), iso-butyl (i-Bu) and tert-butyl (t-Bu).

The term "$C_2$–$C_4$ alkenyl" as used herein is meant to include vinyl, allyl, 1-propen-1-yl, 1-propen-2-yl, 1-buten-1-yl, 1-buten-2-yl, and the like. Included in this invention are all E, Z diastereomers.

The term "$C_3$–$C_6$ cycloalkyl" as used herein is meant to include cyclopropyl, cyclobutyl, cyclopentyl, and cyclohexyl.

The term "halo" as used herein is meant to include fluoro, chloro, bromo, and iodo.

The term "$OC_1$–$C_4$ alkyl" or "$C_1$–$C_4$ alkoxy" as used herein is meant to include methoxy, ethoxy, propoxy, isopropoxy, n-butoxy, iso-butoxy, sec-butoxy, and tert-butoxy.

The term "$OC_3$–$C_6$ cycloalkyl" or "$C_3$–$C_6$ cycloalkoxy" as used herein is meant to include: cyclopropyloxy, cyclobutyloxy, cyclopentyloxy, and cyclohexyloxy.

Representative examples of =Z are where the α-substituent (dashed lines) is hydrogen and the β-substituent (wedge) is e.g. methyl, ethyl, propyl, allyl, carboxymethyl, hydroxy, methoxy, ethoxy, cyclopropyloxy, cyclopentyloxy, acetoxy, fluoro, chloro, bromo, trifluoromethyl, fluoromethyl, chloromethyl, carboxy, N,N-dimethylcarbamate, hydroxymethyl, and the like.

Representative examples where =Z is an alkenyl substituent, =CH—$R^3$, includes =$CH_2$, =CH—$CH_3$, =CH—$CH_2CH_3$, and the like.

Representative examples wherein =Z is the spirocyclopropyl substituent:

includes, e.g.,

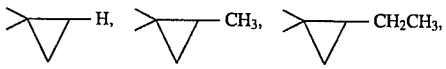

stereoisomers thereof and the like.

Representative examples wherein —$NR^1R^2$ represent a heterocycle include: N-piperidinyl, N-morpholinyl, N-piperazinyl, N-(4-methyl)piperazinyl, N-thiomorpholinyl, N-pyrrolidinyl, N-imidazolidinyl and the like.

Representative compounds of Formula I included in the invention wherein all of the 17-substituents are in the beta configuration are:
7β-ethyl-4-methyl-4-aza-cholest-5-en-3-one,
7β-ethyl-4-methyl-4-aza-cholestane-3-one,
7β-ethyl-4-aza-cholest-5-en-3-one,
7β-ethyl-4-aza-5α-cholestan-3-one,
7β-carboxymethyl-4-aza-cholest-5-en-3-one,
7β-carboxymethyl-4-aza-cholestan-3-one,
7β-propyl-4-methyl-4-aza-cholest-5-en-3-one,
7β-propyl-4-methyl-4-aza-5α-cholestan-3-one,
7β-propyl-4-aza-cholest-5-en-3-one,
7β-propyl-4-aza-5α-cholestan-3-one,
7β-methyl-4-aza-cholest-5-en-3-one,
7βmethyl-4-aza-cholestan-3-one,
4,7β-dimethyl-4-aza-cholest-5-en-3-one,
4,7β-dimethyl-4-aza-5α-cholestan-3-one,
4-methyl-4-aza-5α-cholestan-3,7-dione,
7β-acetoxy-4-methyl-4-aza-5α-cholestan-3-one,
4-methyl-4-aza-cholest-5-en-3,7-dione,
7β-hydroxy-4-methyl-4-aza-5α-cholestane-3-one,
7β-methoxy-4-methyl-4-aza-5α-cholestane-3-one,
7β-hydroxymethyl-4-aza-5α-cholestane-3-one,
7β-bromomethyl-4-aza-5α-cholestane-3-one,
7β-chloromethyl-4-aza-5α-cholestane-3-one,
7β-fluoromethyl-4-aza-5α-cholestane-3-one,
7β-carboxy-4-aza-5α-cholestane-3-one,
7βtrifluoromethyl-4-aza-cholest-5-en-3-one,
7,7-dimethoxy-4-methyl-4-aza-5α-cholestane-3-one,
7β-methoxy-4-methyl-4-aza-cholesta-5-eh-3-one,
7β-methoxy-4-methyl-4-aza-cholesta-6-en-3-one,
7β-cyclopropyloxy-4-methyl-4-aza-5α-cholestane-3-one,
7β-cyclopropyloxy-4-methyl-4-aza-cholesta-5,7-dien-3-one,
7β-propylidene-4-methyl-4-aza-5α-cholestane-3-one,
7β-(2-ethyl)spiroethylene-4-methyl-4-aza-5α-cholestane-3-one,
7β-methyl-4-aza-5α-cholest-1-en-3-one,
7β-methyl-5-oxo-A-nor-3,5-seco-cholestanoic acid,
7β-ethyl-5-oxo-A-nor-3,5-seco-cholestanoic acid,
7β-propyl-5-oxo-A-nor-3,5-seco-cholestanoic acid,
7β-i-propyl-5-oxo-A-nor-3,5-seco-cholestanoic acid,
7β-n-butyl-5-oxo-A-nor-3,5-seco-cholestanoic acid,
7β-i-butyl-5-oxo-A-nor-3,5-seco-cholestanoic acid,
7β-s-butyl-5-oxo-A-nor-3,5-seco-cholestanoic acid,
7β-t-butyl-5-oxo-A-nor-3,5-seco-cholestanoic acid,
7β-n-pentyl-5-oxo-A-nor-3,5-seco-cholestanoic acid, and
7β-n-hexyl-5-oxo-A-nor-3,5-seco-cholestanoic acid.

DISCUSSION OF FORMULA II (STRUCTURE II)

In one embodiment of the instant invention are compounds of Formula II wherein $R^4$ is hydrogen or methyl and $R^5$ is hydrogen or methyl.

A further embodiment of the instant invention are compounds of Formula II wherein:
one of $R^6$ and $R^7$ is selected from the group consisting of hydrogen and methyl, and the other is selected from the group consisting of:
  (b) cyano;
  (c) fluoro;
  (e) OH;
  (g) $C_{1-10}$ alkyl-X—; or $C_{1-10}$ alkyl-X—, where alkyl can be substituted with aryl, and wherein aryl in turn can be substituted with 1–2 of halo or $C_{1-6}$alkyl;
  (h) $C_{2-10}$ alkenyl-X—;
  (i) aryl-X—;
  (j) heteroaryl-X—, wherein heteroaryl is a 5 or 6 membered heteroaromatic ring containing 1–2 ring nitrogen atoms; wherein the aryl in (i) and heteroaryl in (j) can be unsubstituted or substituted with one to two of:
    x) halo; cyano; nitro; trihalomethyl; trihalomethoxy; $C_{1-6}$ alkyl; aryl; $C_{1-6}$ alkylsulfonyl; $C_{1-6}$ alkylarylsulfonamino;
    xi) —$NR_bR_c$; $R_b$—C(O)—N($R_c$)—; wherein $R_b$ and $R_c$ are independently H, $C_{1-6}$ alkyl, aryl, or aryl$C_{1-6}$alkyl; wherein the alkyl moiety can be substituted with 1–3 of: halo; $C_{1-4}$alkoxy; or trifluoromethyl; and the aryl moiety can be substituted with 1–3 of: halo; $C_{1-4}$alkyl; $C_{1-4}$ alkoxy; or trifluoromethyl;
    xii) a heterocyclic group, which is a 5 membered aromatic ring, containing one ring nitrogen atom, or one ring oxygen and one ring nitrogen atom; and
  (k) wherein $R^6$ and $R^7$ taken together can be carbonyl oxygen; and wherein:
X is selected from the group consisting of:
—O—; —S(O)$_n$—; —CH($R_e$)—; —C(O)—N($R_e$)—*; —O—C(O)—N($R_e$)—*;

wherein $R_e$ is H, $C_{1-3}$ alkyl, aryl, aryl $C_{1-3}$ alkyl;

wherein the asterisk (*) denotes the bond which is attached to the 16-position in Structure II; and n is zero or 2.

Novel compounds of the present invention exemplified by this embodiment include but are not limited to the following compounds:

4-aza-4,7β-dimethyl-5α-androstane-3,1 6-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propylox y)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenox y)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;

3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;
3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane;
pharmaceutically acceptable salts thereof, and analogs of the above-described compounds wherein the $C_1$–$C_2$ carbon-carbon bond is a double bond, and/or $R^4$ is —H, and/or $R^5$ is —H or methyl, where appropriate.

In another embodiment of this invention are compounds of Formula II further limited to those wherein the $C_1$–$C_2$ carbon-carbon bond is a single bond, $R^4$ is methyl, $R^5$ is methyl, $R^7$ is selected from unsubstituted or substituted aryloxy, and $R^6$ is hydrogen.

Some non-limiting examples of compounds within this embodiment are:
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenyl]-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
and the pharmaceutically acceptable salts thereof.

A useful compound of the present invention is 3-oxo-4-aza-4,7β-dimethyl-16β-(4-chlorophenoxy)-5α-androstane, or a pharmaceutically acceptable salt thereof.

The following discussion applies to terms used in both Formulas I and II.

As used herein "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonyl, decyl, iso-propyl (i-Pr), iso-butyl (i-Bu), tert-butyl (t-Bu), sec-butyl (s-Bu), iso-pentyl, and the like. "Alkyloxy" (or "alkoxy") represents an alkyl group having the indicated number of carbon atoms attached through an oxygen bridge, e.g., methoxy, ethoxy, propyloxy, and the like. "Alkenyl" is intended to include hydrocarbon groups of either a straight or branched configuration with one or more carbon-carbon double bonds which may occur in any stable point along the chain, such as ethenyl, propenyl or allyl, butenyl, pentenyl, and the like. Included in this invention are all E, Z diastereomers.

The alkyl and alkenyl groups can be unsubstituted or substituted with one or more, and preferably 1–3,
  i) halo; hydroxy; cyano; nitro; mono-, di- or trihalomethyl; oxo; hydroxysulfonyl; carboxy;
  ii) hydroxy$C_{1-6}$alkyl; $C_{1-6}$alkyloxy; $C_{1-6}$ alkylthio; $C_{1-6}$alkylsulfonyl; $C_{1-6}$ alkyloxycarbonyl; in which the $C_{1-6}$ alkyl moiety can be further substituted with 1–3 of: halo; $C_{1-4}$ alkoxy; or trifluoromethyl;
  iii) arylthio; aryl; aryloxy; arylsulfonyl; aryloxycarbonyl; in which the aryl moiety can be further substituted with 1–3 of: halo; $C_{1-4}$ alkyl; $C_{1-4}$ alkoxy; or trifluoromethyl;
  iv) —C(O)NR$_b$R$_c$; —N(R$_b$)—C(O)—R$_c$; —NR$_b$R$_c$; where R$_b$ and R$_c$ are defined above, and where halo is F, Cl, Br or I as used herein.

The term "oxo", as used herein, indicates an oxo radical which can occur in any stable point along the carbon chain resulting in a formyl group, if at the end of the chain, or an acyl or aroyl group at other points along the carbon chain.

As used herein the term "aryl" is intended to mean phenyl or naphthyl, including 1-naphthyl or 2-naphthyl, either unsubstituted or substituted as described below.

The term "heteroaryl" as used herein, is intended to include a 5, 6 or 7 membered heteroaromatic radical containing at least one member selected from the group consisting of: one ring oxygen atom, one ring sulfur atom, 1–4 ring nitrogen atoms, or combinations thereof; in o which the heteroaryl ring can also be fused with one benzo or heteroaromatic ring. This category includes the following either unsubstituted or substituted heteroaromatic rings(as described below): pyridyl, furyl, pyrryl, thienyl, isothiazolyl, imidazolyl, benzimidazolyl, tetrazolyl, pyrazinyl, pyrimidyl, quinolyl, quinazolinyl, isoquinolyl, s benzofuryl, isobenzofuryl, benzothienyl, pyrazolyl, indolyl, isoindolyl, purinyl, carbazolyl, isoxazolyl, thiazolyl, isothiazolyl, oxazolyl, benzthiazolyl, and benzoxazolyl. The heteroaryl ring may be attached within structural Formula II or substituted at any heteroatom or carbon atom in the ring. However, the attachment to —X— has to be through a ring atom which affords a stable structure. The heteroaryl ring can also be fused to a benzo ring.

The one or more, preferably one to three, substituents which can be on the aryl and heteroaryl groups named above are independently selected from:
  v) halo; hydroxy; cyano; nitro; mono-, di- or trihalomethyl; mono-, di- or trihalomethoxy; $C_{2-6}$ alkenyl; $C_{3-6}$ cycloalkyl; formyl; hydrosulfonyl; carboxy; ureido;

vi) $C_{1-6}$ alkyl; hydroxy $C_{1-6}$ alkyl; $C_{1-6}$ alkyloxy; $C_{1-6}$ alkyloxy $C_{1-6}$alkyl; $C_{1-6}$ alkylcarbonyl; $C_{1-6}$ alkylsulfonyl; $C_{1-6}$ alkylthio; $C_{1-6}$ alkylsulfinyl; $C_{1-6}$ alkylsulfonamido; $C_{1-6}$ alkylarylsulfonamido; $C_{1-6}$ alkyloxycarbonyl; $C_{1-6}$ alkyloxycarbonyl $C_{1-6}$alkyl; $R_bR_cN$—C(O)-$C_{1-6}$alkyl; $C_{1-6}$ alkanoylamino $C_{1-6}$ alkyl; aroylamino $C_{1-6}$ alkyl; wherein the $C_{1-6}$ alkyl moiety can be substituted with 1–3 of: halo; $C_{1-4}$alkoxy; or trifluoromethyl;

vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; $C_{1-4}$alkyl; $C_{1-4}$alkoxy; or trifluoromethyl;

viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is $C_{1-6}$alkyl or aryl, in which the alkyl moiety can be substituted with 1–3 of: halo; $C_{1-4}$alkoxy; or trifluoromethyl, and the aryl moiety can be substituted with 1–3 of: halo; $C_{1-4}$alkyl; $C_{1-4}$ alkoxy, or trifluoromethyl; —N(R$_b$)—C(O)NR$_c$R$_d$, wherein R$_d$ is selected from H, $C_{1-6}$ alkyl, and aryl; in which said $C_{1-6}$alkyl and aryl can be substituted as described above in (f) for R$_b$ and R$_c$;

ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group.

The fused heteroaromatic ring systems include: purine, imidazoimidazole, imidazothiazole, pyridopyrimidine, pyridopyridazine, pyrimidopyrimidine, imidazopyridazine, pyrrolopyridine, imidazopyridine, and the like.

The "heterocyclic" group includes the aromatic heteroaryl rings described above and also their respective dihydro, tetrahydro, hexahydro and fully saturated ring systems. Examples include: dihydroimidazolyl, dihydrooxazolyl, dihydropyridyl, tetrahydrofuryl, dihydropyrryl, tetrahydrothienyl, dihydroisothiazolyl, 1,2-dihydrobenzimidazolyl, 1,2-dihydrotetrazolyl, 1,2-dihydropyrazinyl, 1,2-dihydropyrimidyl, 1,2-dihydroquinolyl, 1,2,3,4-tetrahydroisoquinolyl, 1,2,3,4-tetrahydrobenzofuryl, 1,2,3,4-tetrahydroisobenzofuryl, 1,2,3,4-tetrahydrobenzothienyl, 1,2,3,4-tetrahydropyrazolyl, 1,2,3,4-tetrahydroindolyl, 1,2,3,4-tetrahydroisoindolyl, 1,2,3,4-tetrahydropurinyl, 1,2,3,4-tetrahydrocarbazolyl, 1,2,3,4-tetrahydroisoxazolyl, 1,2,3,4-tetrahydrothiazolyl, 1,2,3,4-tetrahydrooxazolyl, 1,2,3,4-tetrahydrobenzthiazolyl, and 1,2,3,4-tetrahydrobenzoxazolyl and the like.

The heterocyclic group can be substituted in the same fashion as described above for heteraryl.

Whenever the terms "alkyl", "alkenyl", "alkyloxy (or alkoxy)", "aryl" or "heteroaryl", or one of their prefix roots, appear in a name of a substituent in Formula I and II (e.g., aralkoxyaryloxy) they shall have the same definitions as those described above for "alkyl", "alkenyl", "alkyloxy (or alkoxy)", "aryl" and "heteroaryl", respectively. Designated numbers of carbon atoms (e.g., $C_{1-10}$) shall refer independently to the number of carbon atoms in an alkyl or alkenyl moiety or to the alkyl or alkenyl portion of a larger substituent in which alkyl or alkenyl appears as its prefix root.

Also included within the scope of this invention are pharmaceutically acceptable salts of the compounds of Formula I and II, where a basic or acidic group is present on the structure. When an acidic substituent is present, i.e., —COOH, there can be formed the ammonium, sodium, potassium, calcium salt, and the like, for use as the dosage form. Where a basic group is present, i.e., amino or a basic heteroaryl radical such as, e.g., 4-pyridyl, an acidic salt, i.e., hydrochloride, hydrobromide, acetate, pamoate, and the like, can be used as the dosage form.

Also, in the case of the —COOH group being present, pharmaceutically acceptable esters can be employed, e.g., acetate, maleate, pivaloyloxymethyl, and the like, and those esters known in the art for modifying solubility or hydrolysis characteristics for use as sustained release or prodrug formulations.

Representative salts include the following salts: acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, Iodide, tosylate, isothionate, triethiodide, lactate, and valerate.

In addition, some of the compounds of the instant invention may form solvates with water or common organic solvents. Such solvates are encompassed within the scope of this invention.

The compounds of Formula I and II of the present invention have asymmetric centers and may occur as racemates, racemic mixtures and as individual enantiomers or diastereomers, with all isomeric forms being included in the present invention as well as mixtures thereof. Furthermore, some of the crystalline forms for compounds of the present invention may exist as polymorphs and as such are intended to be included in the present invention.

The term "therapeutically effective amount" shall mean that amount of a drug or pharmaceutical agent that will elicit the biological or medical response of a tissue, system, animal or human that is being sought by a researcher, veterinarian, medical doctor or other clinician.

Formula I

The compounds of this invention can be made by procedures outlined in the following Flowsheets. All temperatures are in degrees Celsius.

GENERAL FLOWSHEET

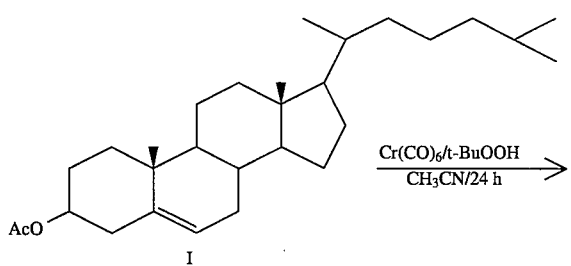

15
-continued
GENERAL FLOWSHEET

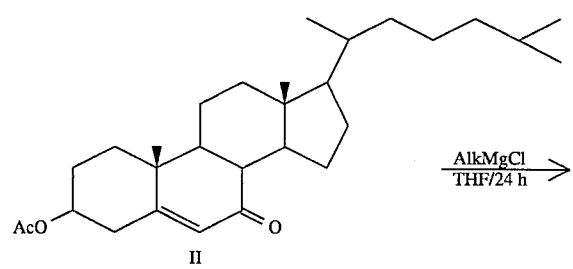
II $\xrightarrow{\text{AlkMgCl}}{\text{THF/24 h}}$

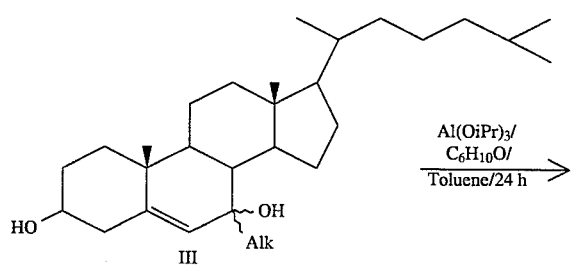
III $\xrightarrow{\text{Al(OiPr)}_3/ \atop C_6H_{10}O/}{\text{Toluene/24 h}}$

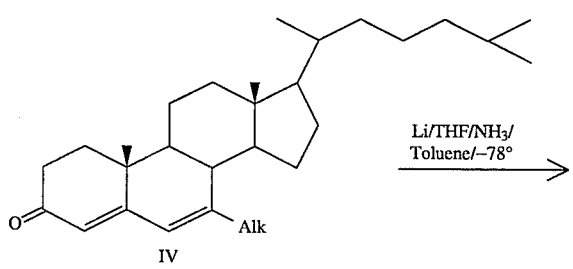
IV $\xrightarrow{\text{Li/THF/NH}_3/}{\text{Toluene/}-78°}$

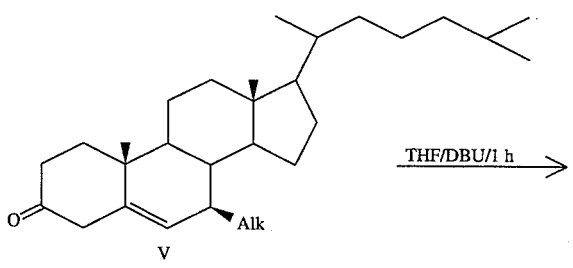
V $\xrightarrow{\text{THF/DBU/1 h}}$

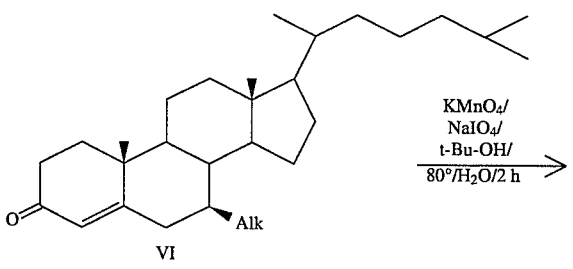
VI $\xrightarrow[\text{80°/H}_2\text{O/2 h}]{\text{KMnO}_4/ \atop \text{NaIO}_4/ \atop \text{t-Bu-OH/}}$

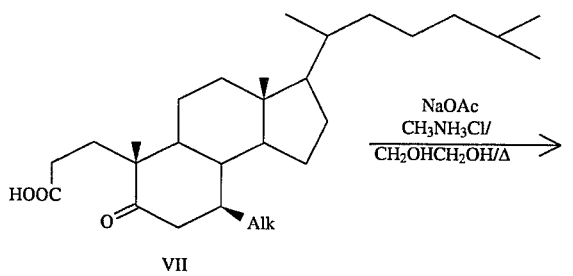
VII $\xrightarrow[\text{CH}_2\text{OHCH}_2\text{OH/}\Delta]{\text{NaOAc} \atop \text{CH}_3\text{NH}_3\text{Cl/}}$

16
-continued
GENERAL FLOWSHEET

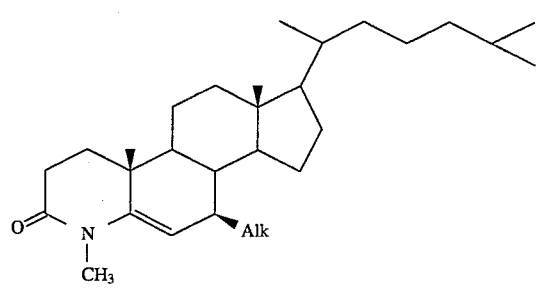
VIII

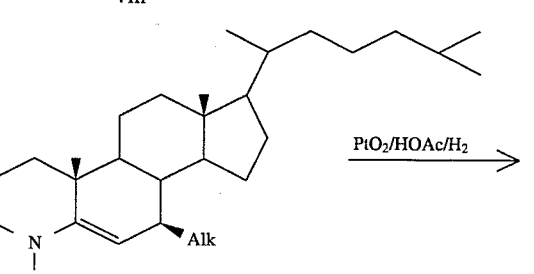
VIII $\xrightarrow{\text{PtO}_2/\text{HOAc/H}_2}$

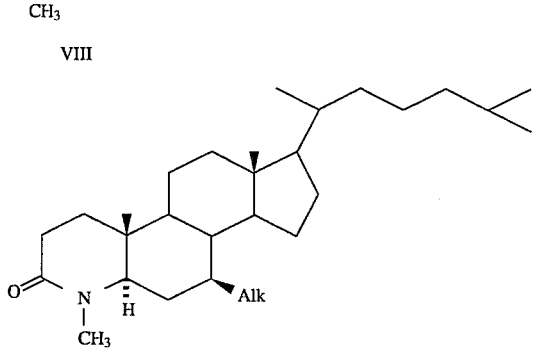
IX

VII $\xrightarrow{\text{NH}_4\text{OAc/HOAc}}$

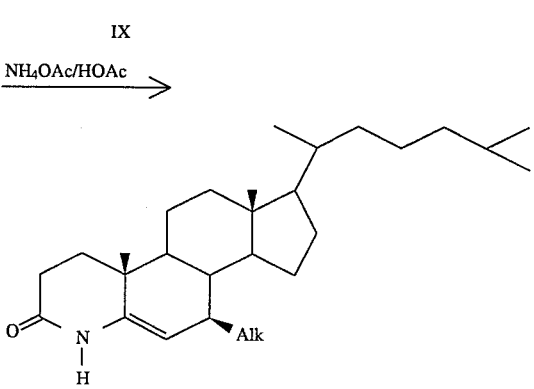
X

X $\xrightarrow{\text{PtO}_2/\text{H}_2}{\text{HOAc}}$

-continued
GENERAL FLOWSHEET

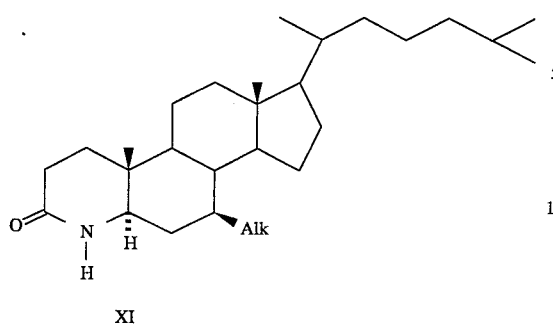

FLOWSHEET A

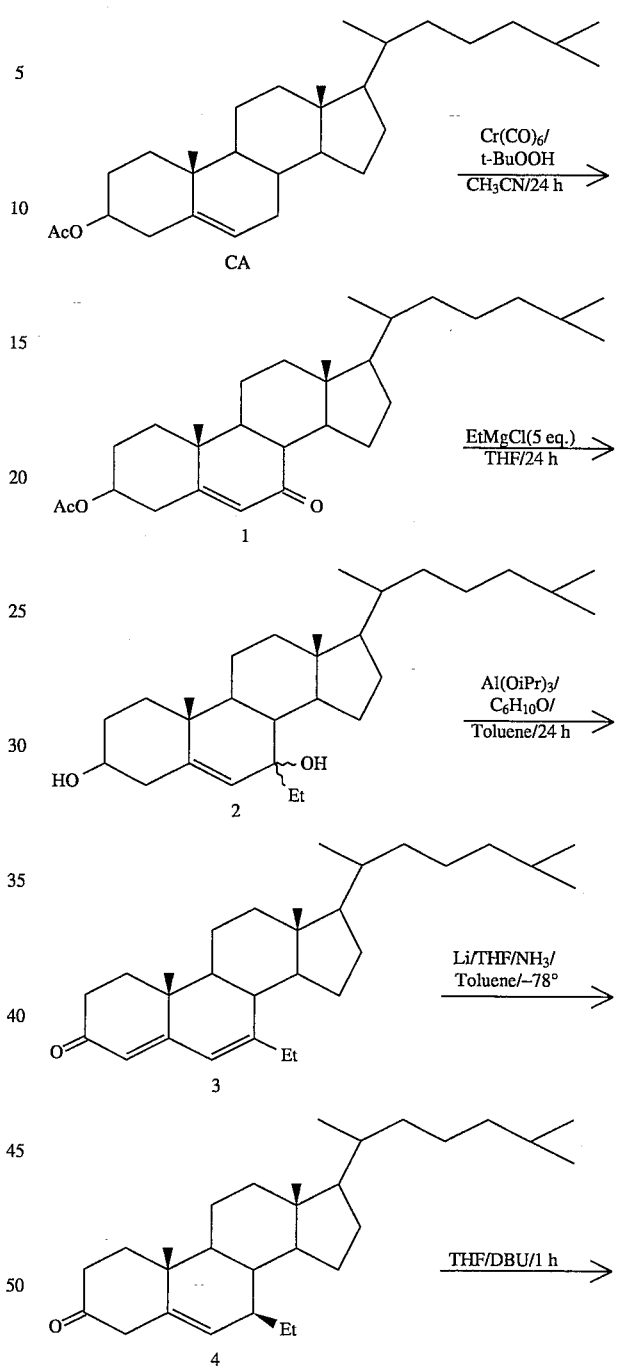

7-Beta Alkyl Series

The compounds of the instant invention comprising Z as a 7β alkyl group, e.g., methyl, ethyl, isopropyl, allyl, can be prepared by the procedure outlined in The General Flowsheet.

As seen in the Flowsheet, the starting 3-acetoxy-cholest-5-ene I (see Example 1 for synthesis) is oxidized to the corresponding 5-en-7-one II by treatment with hydrogen t-butyl peroxide and chromium hexacarbonyl in e.g., acetonitrile, at reflux. The $C_1$–$C_4$ alkyl group, designated Alk, e.g., methyl, can be introduced at this point by a Grignard reaction using e.g., alkyl magnesium chloride in e.g., anhydrous tetrahydrofuran (THF) at 0°–23° C. to produce the 7-alkyl-7-hydroxy adduct III. This is then oxidized with e.g., aluminum isopropoxide and cyclohexanone (Oppenauer oxidation conditions) in refluxing toluene solvent to produce the 7-alkyl-4,6-dien-3-one IV. This in turn is reduced via a e.g., metal-ammonia reduction, using lithium, liquid ammonia, THF and toluene at −78° C., quenching the reaction with dibromoethane and ammonium chloride, to selectively yield the 7-beta-alkyl-5-en-3-one V. In the next step the delta-5 double bond is isomerized to the 4-ene by use of DBU (1,8-diazabicyclo-[5.4.0]undec-7-ene) in, e.g., refluxing THF to produce the 7-beta-alkyl 4-en-3-one, VI. The A Ring is next cleaved by treatment with e.g., potassium permanganate, sodium periodate in t-butyl alcohol at 80° C. to produce the corresponding seco-acid VII. Treatment of the seco-acid with an appropriate amine e.g., methylamine hydrochloride and sodium acetate in ethylene glycol at 180° C., yields e.g., the 4-methyl-4-aza-cholest-5-en-3-one VIII. This in turn is selectively reduced with e.g., $PtO_2$ catalyst in a hydrogen atmosphere, to remove the 5-position double bond to produce the 5α-hydrogen compound IX. The seco-acid VII can be similarly treated with ammonium acetate in acetic acid (HOAc) to produce the corresponding N—H compound, X, which can then be analogously treated with $PtO_2$ in a catalytic hydrogenation to produce the corresponding 5α-4N—H compound XI. Similarly, use of hydroxylamine or hydrazine for ring A closure of the seco acid will afford the corresponding delta-5-4N—X compounds where —X can be —OH or —$NH_2$, respectively. Reaction of the anion of saturated 4N-compound (generated from the NH precursor by NaH treatment) with methylsulfenyl chloride can provide the corresponding 4N—X compound where —X is —$SCH_3$. Thus, R can also be —OH, —$NH_2$ or $SCH_3$ in the Formula.

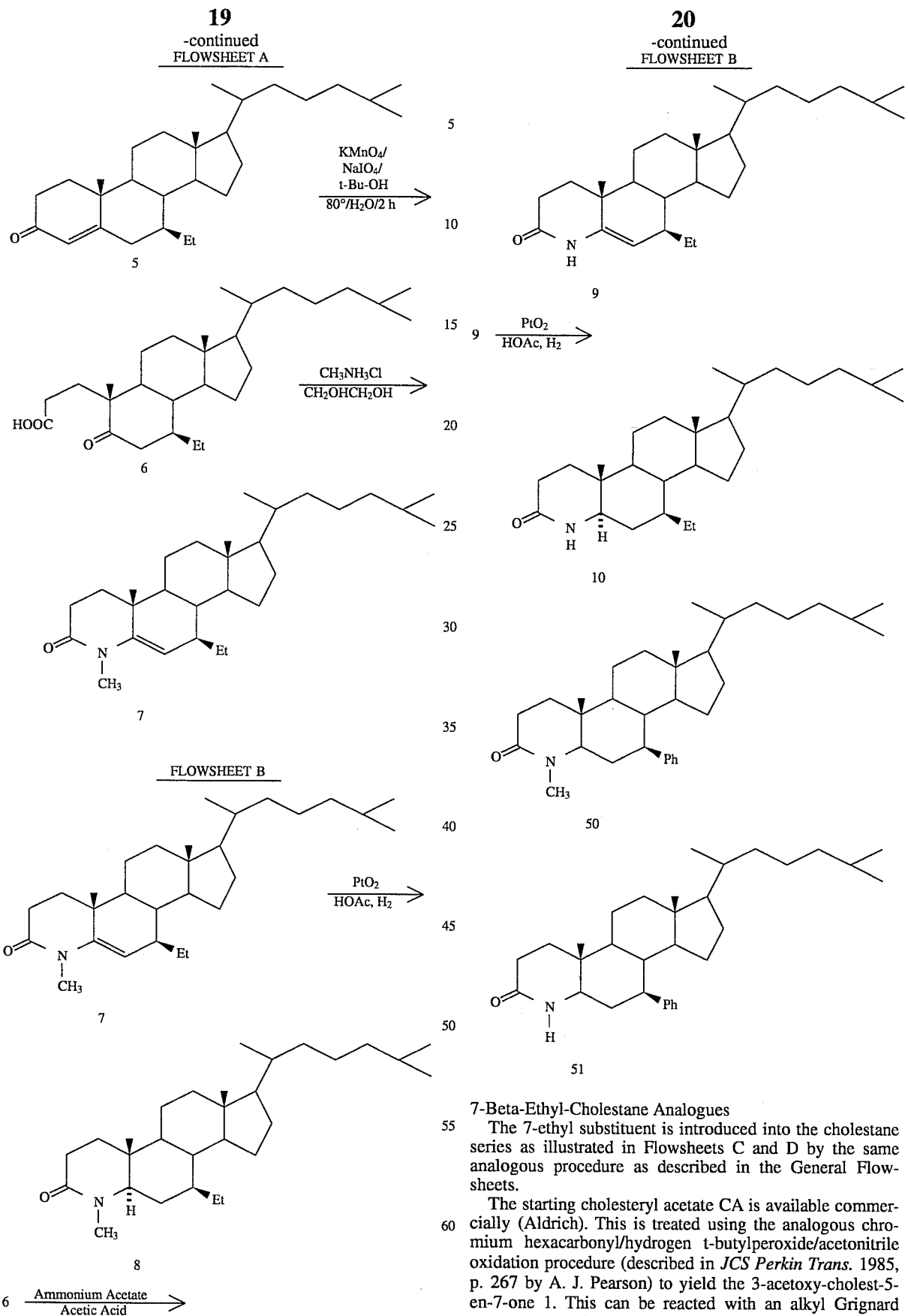

7-Beta-Ethyl-Cholestane Analogues

The 7-ethyl substituent is introduced into the cholestane series as illustrated in Flowsheets C and D by the same analogous procedure as described in the General Flowsheets.

The starting cholesteryl acetate CA is available commercially (Aldrich). This is treated using the analogous chromium hexacarbonyl/hydrogen t-butylperoxide/acetonitrile oxidation procedure (described in *JCS Perkin Trans.* 1985, p. 267 by A. J. Pearson) to yield the 3-acetoxy-cholest-5-en-7-one 1. This can be reacted with an alkyl Grignard reagent, e.g., ethyl magnesium chloride to form the adduct 2. This is oxidized under Oppenauer conditions to yield the dienone 3, which then can undergo metal-ammonia reduction to yield the 7β-ethyl-5-en-3-one, 4. This is isomerized using DBU to the 4-en-3-one, 5, which is oxidized to open Ring A to yield the seco-acid 6. This can be treated with amines, e.g. methylamine, to yield the A-ring closed 4-methyl-4-aza compound 7. This in turn can be catalytically hydrogenated to yield the 7-ethyl-5-alpha-4-methyl-4-aza-cholestan-3-one, 8.

Similarly, by treatment of the seco-acid 6 with ammonium acetate/acetic acid, the corresponding 4-NH analog 9, is produced which can be catalytically hydrogenated to yield the 7-beta-ethyl-5α-4-aza-cholestan- 3-one, 10.

Following the same procedure but using phenylmagnesium chloride as the Grignard reagent, the corresponding compounds 50 and 51 are produced ("Ph" represents phenyl).

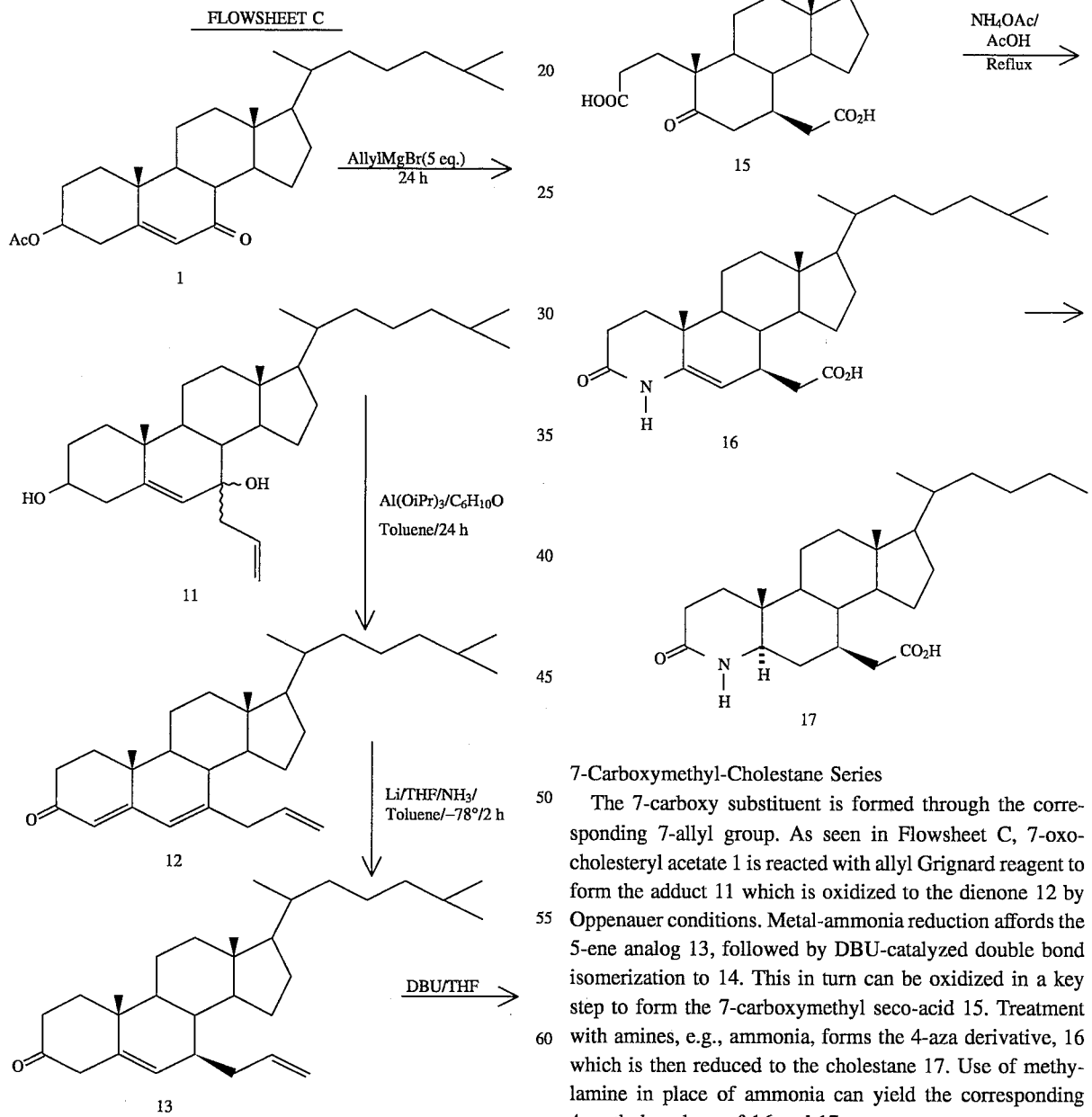

7-Carboxymethyl-Cholestane Series

The 7-carboxy substituent is formed through the corresponding 7-allyl group. As seen in Flowsheet C, 7-oxo-cholesteryl acetate 1 is reacted with allyl Grignard reagent to form the adduct 11 which is oxidized to the dienone 12 by Oppenauer conditions. Metal-ammonia reduction affords the 5-ene analog 13, followed by DBU-catalyzed double bond isomerization to 14. This in turn can be oxidized in a key step to form the 7-carboxymethyl seco-acid 15. Treatment with amines, e.g., ammonia, forms the 4-aza derivative, 16 which is then reduced to the cholestane 17. Use of methylamine in place of ammonia can yield the corresponding 4-methyl analogs of 16 and 17.

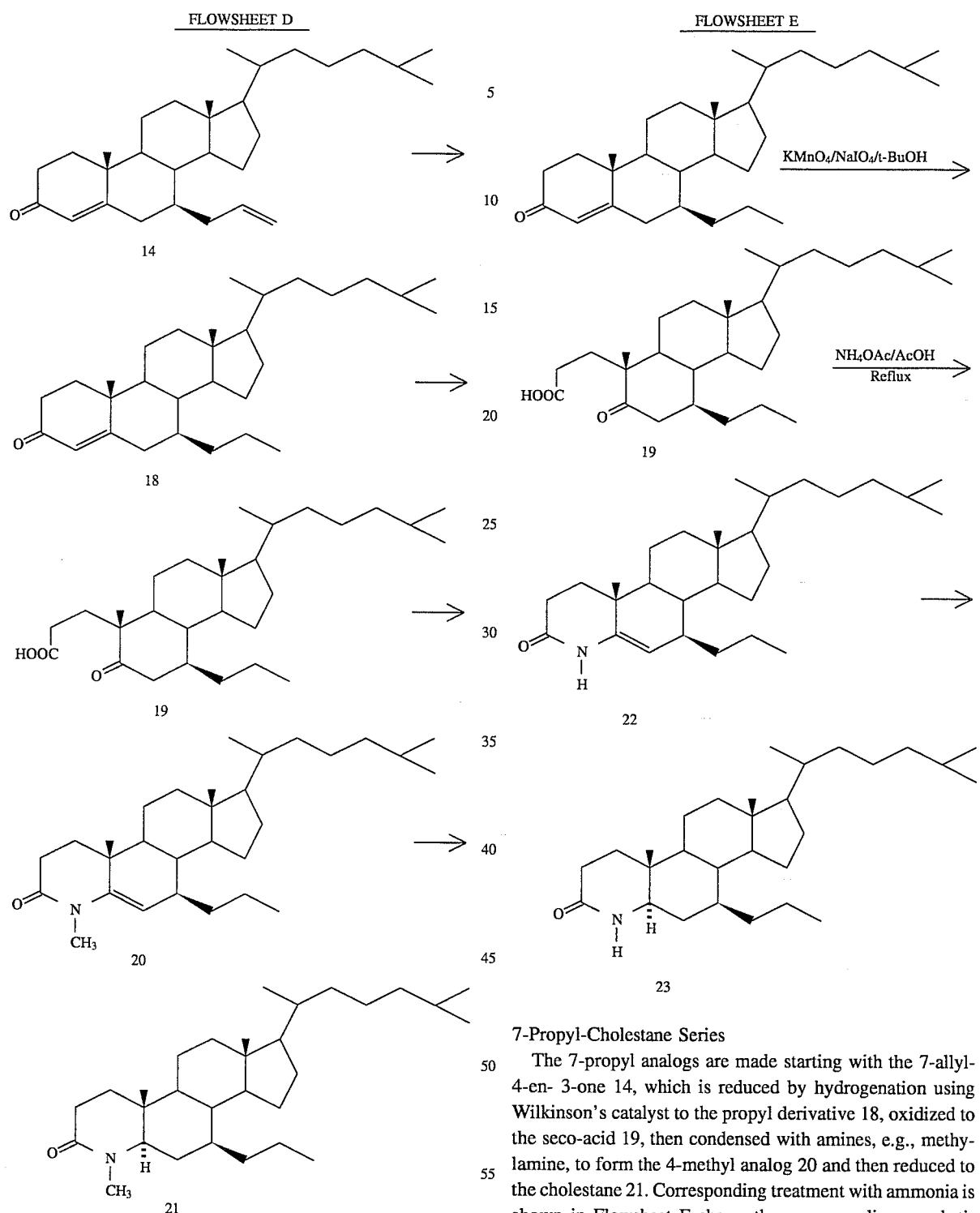

7-Propyl-Cholestane Series

The 7-propyl analogs are made starting with the 7-allyl-4-en- 3-one 14, which is reduced by hydrogenation using Wilkinson's catalyst to the propyl derivative 18, oxidized to the seco-acid 19, then condensed with amines, e.g., methylamine, to form the 4-methyl analog 20 and then reduced to the cholestane 21. Corresponding treatment with ammonia is shown in Flowsheet E shows the corresponding unsubstituted 4-aza 22 and cholestane 23 analogs.

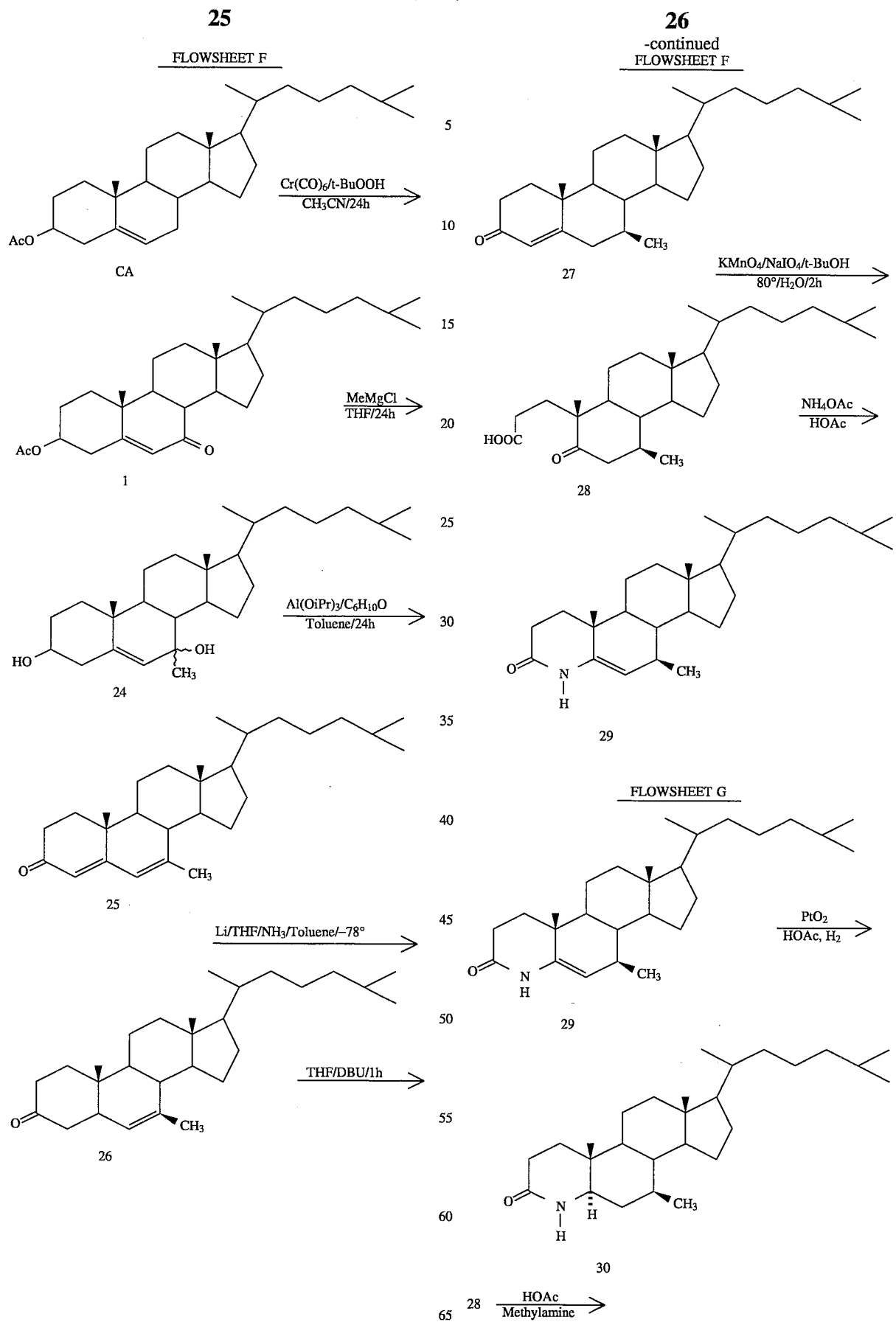

27
-continued
FLOWSHEET G

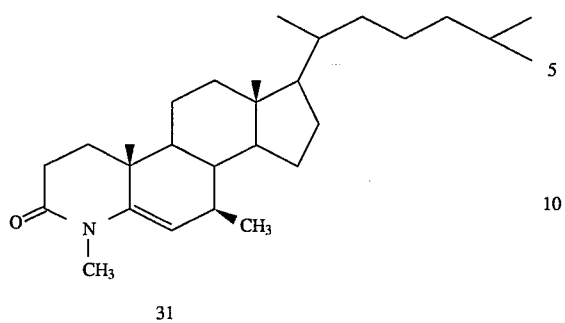

31

31 $\xrightarrow[\text{HOAc, H}_2]{\text{PtO}_2}$

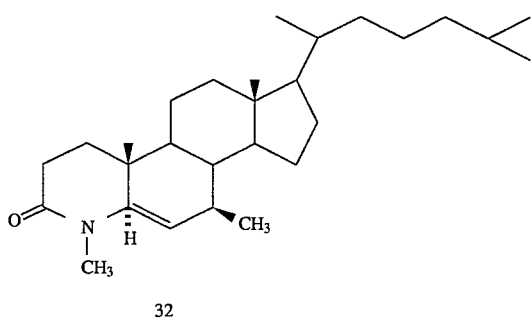

32

7-Beta Methyl Cholestane Series

The 7-beta methyl cholestane series is prepared by the analogously same route as described in Flowsheets A and B for the ethyl derivatives.

The methyl Grignard reagent is used to form the adduct 24, followed by Oppenauer oxidation to form 25, metal-ammonia reduction to form 26, double bond isomerization to form 27, seco-acid oxidation to form 28, and treatment by an ammonium salt to form 29, and reduction to form 30. Corresponding treatment with methylamine produces the corresponding 4-methyl-4-aza compounds, 31 and by reduction, 32.

FLOWSHEET H

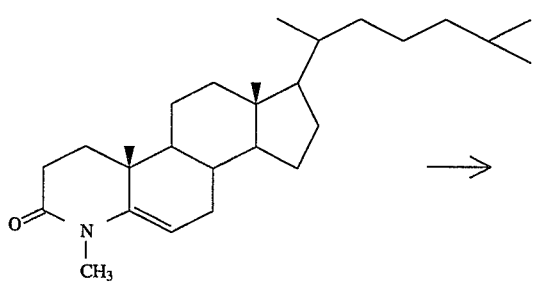

33

28
-continued
FLOWSHEET H

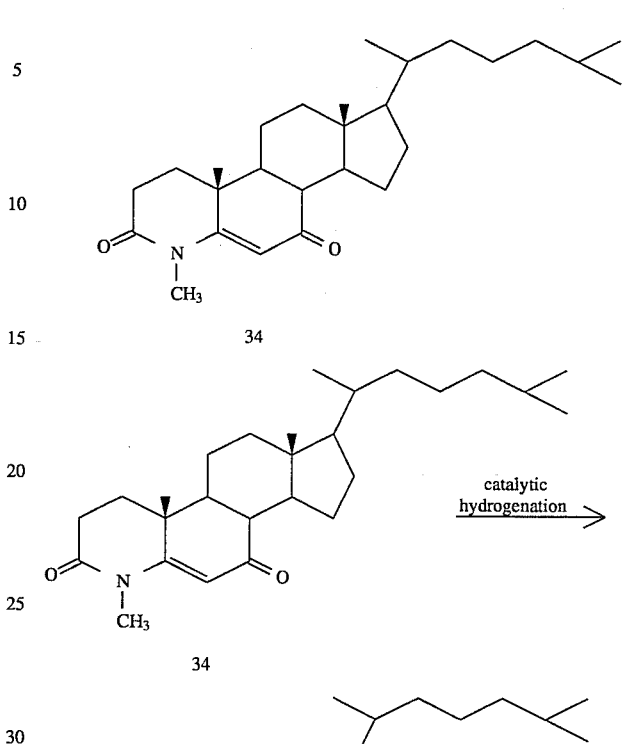

34 catalytic hydrogenation →

34

+ 36

35

FLOWSHEET I

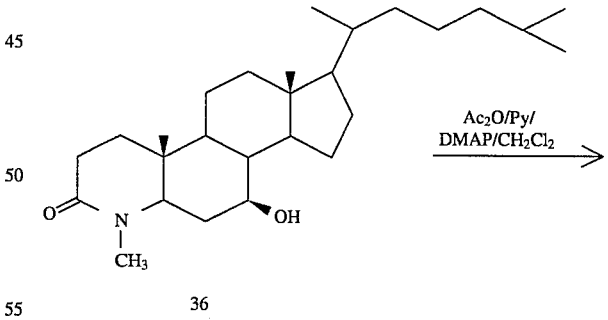

36

$\xrightarrow{\text{Ac}_2\text{O/Py/}}_{\text{DMAP/CH}_2\text{Cl}_2}$

-continued
FLOWSHEET I

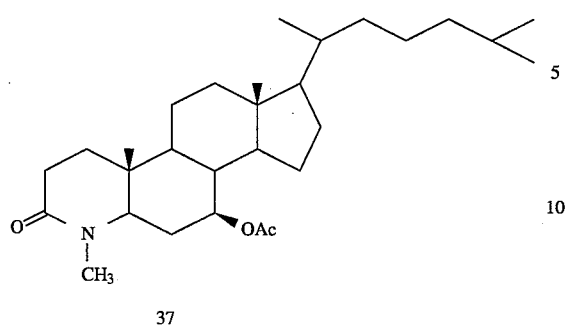

37

7-Beta Acetoxy Cholestane Series

The 7-beta acetoxy series is prepared by the oxidation of starting 33 to the 5-en-7-one 34 by the chromium hexacarbonyl procedure described for 1, or by pyridine-dichromate/ t-butyl hydroperoxide oxidation as described in the Examples. Subsequent noble metal, e.g., platinum, ruthenium, catalyzed reduction of 34 yields two products, the reduced 7-oxo compound 35, and 7-beta hydroxy compound 36. Acylation of 36 with acetic anhydride ($Ac_2O$) yields the 7-beta acetoxy compound 37. DMAP is dimethylaminopyridine; Py is pyridine; Ac is acetyl.

FLOWSHEET J

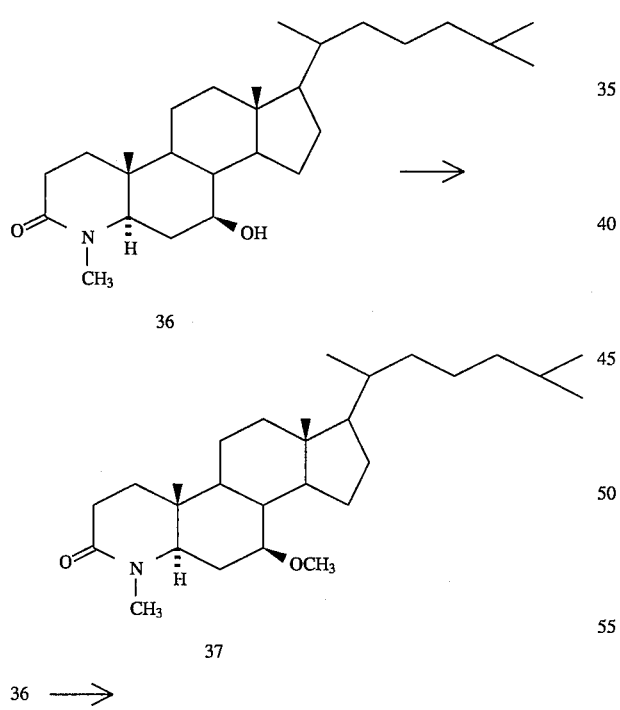

36 $\longrightarrow$

-continued
FLOWSHEET J

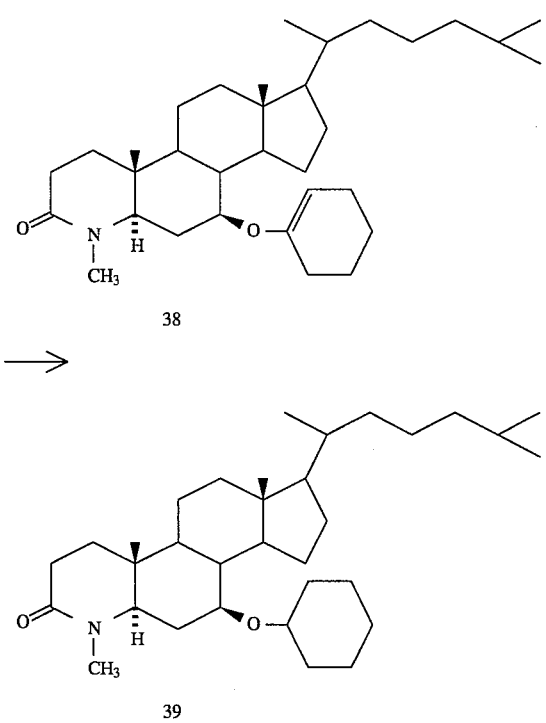

38 $\longrightarrow$

39

The 7-beta ethers in the cholestane series are prepared from the 7-beta-ol (7-beta hydroxy derivative). As illustrated in Flowsheet J, the 4-N-methyl-7-beta ol 36 can be reacted with e.g., methyl iodide and sodium hydride in e.g., dimethylformamide, to produce the corresponding methyl ether 37. The other $C_1$–$C_4$ ethers can be prepared in the same manner.

The $C_3$–$C_6$ cycloalkyl ethers can be prepared according to the analogous procedure of *Steroids*, 1972, vol. 19, pp. 639–647 by R. Gardi, et al. For example, 36 can be reacted with 1,1-dimethoxy-cyclohexane to produce the enol ether 38, which can be reduced to the corresponding saturated compound by the use of palladium catalyzed hydrogenation.

FLOWSHEET K

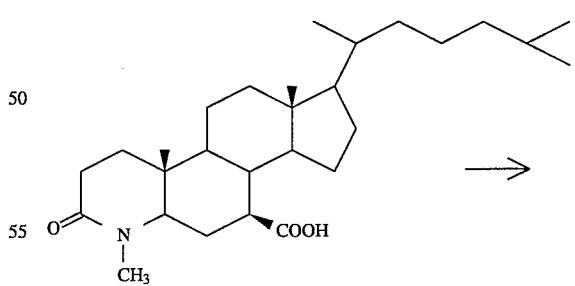

45

31
-continued
FLOWSHEET K
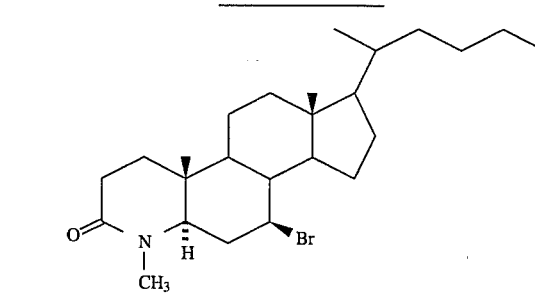
40
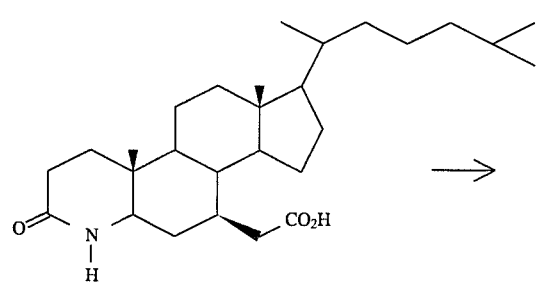
17
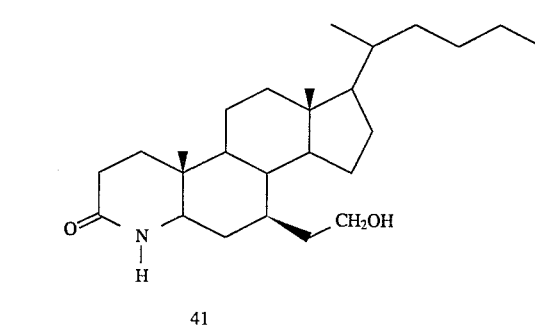
41
41 →
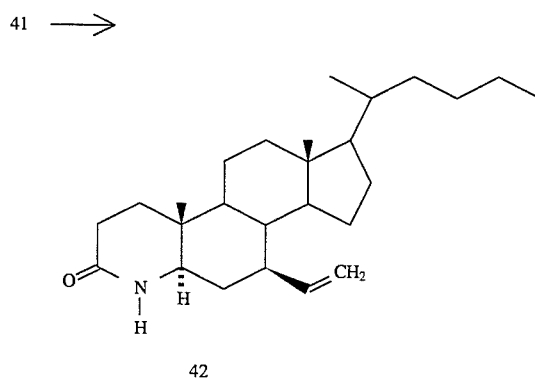
42
32
FLOWSHEET L
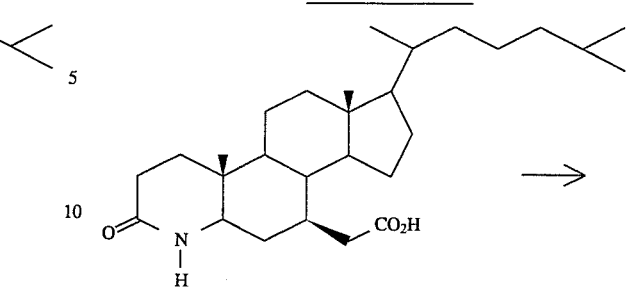
17
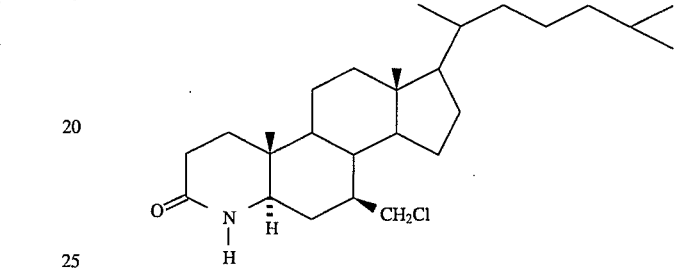
43
17 →
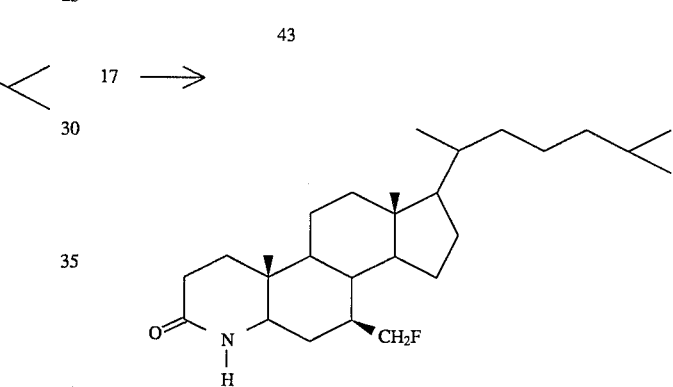
44
FLOWSHEET M
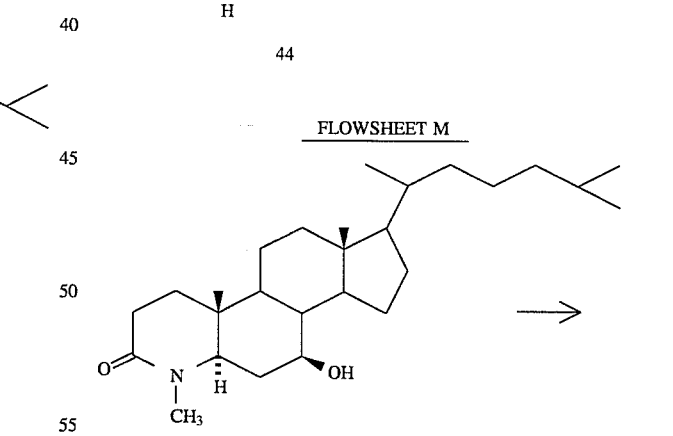
36

FLOWSHEET M -continued

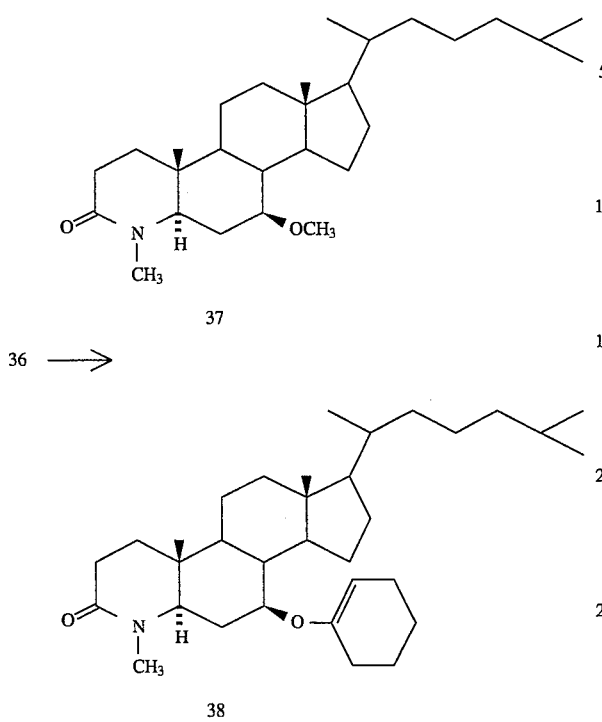

The 7-haloalkyl series is made by the procedure illustrated in Flowsheet K.

Starting with the 7-beta-carboxy, 45, this can be treated under Hunsdiecker reaction conditions, i.e., bromination of a mercury metal salt, to yield the 7-bromo derivative 40. The chloro and iodo derivatives can be made in substantially the same fashion.

The haloethyl compounds can be made by starting with the 7-carboxymethyl analog 17 which can be reacted with a reducing agent, e.g., borane, to produce the primary alcohol 41. This in turn can be reacted with triphenylphosphine and carbon tetrabromide to produce the bromoethyl derivative 42.

The halomethyl compounds can be produced starting with the carboxymethyl derivative 17. This is treated with lead tetraacetate under oxidative decarboxylation/halogenation conditions, with a chloride, bromide or iodide salt to yield, e.g., the 7-chloromethyl analog 43. The carboxymethyl compound 17 can be treated with a fluorinating agent ($XeF_2$) to yield the 7-fluoromethyl analog 44.

The 7-trifluoromethyl derivative can be made from the 7-carboxy derivative 45, by conventional Dast halogenation conditions using $SF_4$ to yield the 7-trifluoromethyl analog 46.

FLOWSHEET N

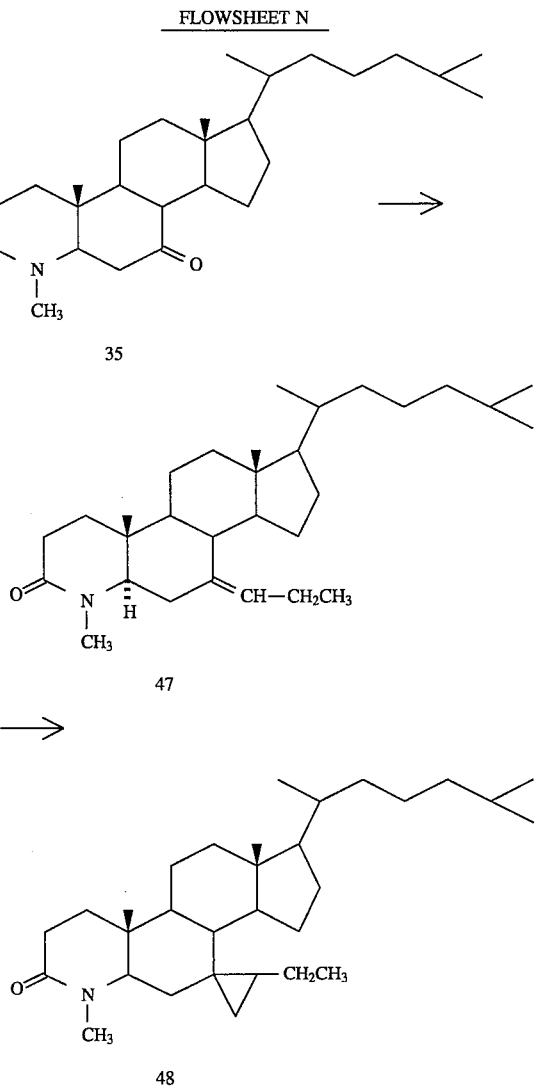

Flowsheet N illustrates the 7-methylene series. As seen, the Wittig reaction, using e.g., $Ph_3PCH(CH_2CH_3)$, carded out on the 7-oxo compound 35, leads to the 7-(ethyl)methylene compound 47.

Subsequent treatment of 47 with the cyclopropyl forming reagents, $CH_2I_2$ and zinc, produces the ethyl cyclopropyl spiro compound 48, which is a mixture of stereoisomers.

FLOWSHEET O

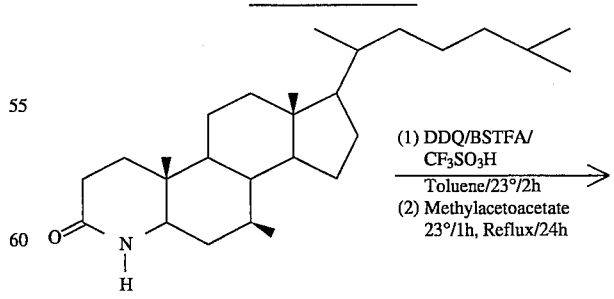

-continued
FLOWSHEET O

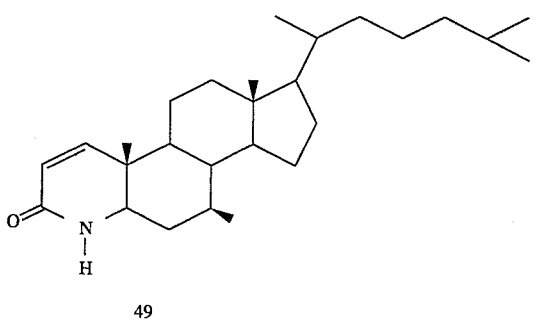

49

Flowsheet O illustrates the synthesis of the 1-ene 7-substituted analogs. For example compound 30 is stirred with DDQ, BSTFA (bis-trimethylsilyltrifluoroacetamide) and trifluoromethyl sulfonic acid in toluene at room temperature for 24 hours, methyl acetoacetate is added and the mixture refluxed for 24 hours and purified by preparative thin layer chromatography on silica gel using 3:1 chloroform/acetone to yield 49.

Formula II

The compounds of Formula II useful in the present invention can be prepared readily according to the following reaction Schemes and Examples or modifications thereof using readily available starting materials, reagents and conventional synthesis procedures. In these reactions, it is also possible to make use of variants which are themselves known to those of ordinary skill in this art, but are not mentioned in greater detail. Specific definitions of variables in the Schemes are illustrative only, and are not intended to limit the procedures described. Some abbreviations used herein are as follows: Ph is phenyl; Ac is an acyl group; t-Bu is tert-butyl; Et is ethyl; Me is methyl; i-Am is iso-amyl; EtOAc is ethyl acetate.

The inhibitors described in Scheme 1 can be prepared as follows. 4-Aza-4-methyl-5α-androstan-3,17-dione (A) is first converted into the isomeric 3,16-dione (52) by the following sequence of reactions: (1) treatment of A with isoamyl nitrite in t-butanol in the presence of potassium t-butoxide to generate the intermediate 16-oximino-17-ketone; (2) reduction of the 17-keto group with hydrazine hydrate and potassium hydroxide in ethylene glycol at elevated temperatures to give 16-oxime (B); and (3) cleavage of the 16-oximino group in B either by hydrolysis with aqueous acetic acid at elevated temperatures or with sodium bisulfite followed by treatment with aqueous hydrochloric acid to afford (52). Reduction of the 16-ketone (52) to the 16β-alcohol (53) is carried out with a suitable hydride-based reducing agent, such as sodium borohydride in methanol or lithim tri-sec-butylborohydride in tetrahydrofuran (THF). Alcohol (53) is converted into its alkyl ether derivatives (54) and (55), by first generating the alkoxide anion with potassium hydride in N,N-dimethylformamide (DMF) or potassium hydroxide in dimethyl sulfoxide (DMSO) followed by addition of the appropriate alkyl bromide or iodide. The 16β-(n-propyloxy) derivative (56) is obtained from the precursor 16β-(allyloxy) derivative (55) by catalytic hydrogenation.

The inhibitors described in Scheme 2 can be prepared as follows. 16-Oxime (B) is converted into the 16β-amine (C) by catalytic hydrogenation in the presence of a heterogeneous catalyst such as platinum oxide in aqueous acetic acid. Acylation of (C) is effected with the appropriate acid anhydride or acid chloride in the presence of an acid acceptor such as pyridine, triethylamine, and 4-dimethylaminopyridine (DMAP). In this fashion are obtained Examples 6 and 7. Carbamates, such as (59) depicted in Scheme 3, are made by treatment of alcohol (53) with the appropriate isocyanate in the presence of an organic base, such as triethylamine, pyridine, and 4-dimethylaminopyridine.

The inhibitors described in Scheme 4 can be prepared as follows. The 16β-alcohol (53) is converted into the 16α-alcohol (60) by treatment with 4-nitro-benzoic acid in the presence of diethyl azadicarboxylate (DEAD) and triphenylphosphine to generate the intermediate 16α-(p-nitrobenzoate) ester (D) followed by hydrolysis in aqueous base in an appropriate alcohol solvent. Alkylation of (60) is carried out in an analogous fashion as described above with alcohol (53) to yield the desired 16α-alkyl ethers, such as the 16α-methoxy derivative (Example 10) shown in Scheme 4.

The 7β-methyl inhibitors described in Scheme 5 are prepared in a similar manner as that described above for the examples in Scheme 1, but using instead as starting material, 4-aza-4,7β-dimethyl-5α-androstan-3,17-dione (E).

The 7β-methyl inhibitors described in Scheme 6 are prepared as follows. Compound (71) is prepared by treatment of alcohol (63) with t-butyl trichloroacetimidate in the presence of an organic sulfonic acid, such as trifluoromethanesulfonic acid. The 16β-aryloxy derivatives, such as Compounds 72-75, are obtained by first generating the alkoxide anion from alcohol (63) with potassium or sodium hydride in tetrahydrofuran or N,N-dimethylformamide or potassium hydroxide in dimethylsulfoxide and subsequent addition of the appropriately substituted fluorobenzene.

The 7β-methyl inhibitors described in Scheme 7 are prepared in a similar manner as that described above for the examples in Scheme 4, but using instead as starting material the 7β-methyl-16β-ol intermediate (63). Inversion of configuration at the 16-position to form (F) is effected using a Mitsunobu-based transformation as shown in Scheme 7. O-Alkylation to generate 16α-ethers, such as (77), is performed as already described above.

The inhibitors described in Scheme 8 are prepared as follows. Addition of methylmagnesium bromide in tetrahydrofuran to either ketone (52) or (62) affords the corresponding 16α-methyl-16β-alcohol (78) or (79). O-Alkylation or O-arylation is then carried out as described in the previous Schemes to afford the 16α-methyl-16β-ether derivatives, Compounds (80) and (81).

The inhibitors described in Scheme 9 are prepared as follows. The 7β-methyl-16α-alcohol (76) is converted into the 16β-thiol (H) by treatment with thiolacetic acid in the presence of diisopropyl azodicarboxylate (DIAD) and triphenylphosphine to give the intermediate 16β-thioacetate (G), which is then hydrolyzed under basic conditions to yield thiol (H). Alkylation is effected by generating the mercaptide anion with sodium hydride or potassium hydride in tertahydrofuran or N,N-dimethylformamide followed by addition of the appropriate alkyl halide. In this fashion are prepared Compounds 82-84. The corresponding sulfones, such as Compound 85, are obtained by treatment of the precursor thioethers (82-84) with an oxidizing agent, such as organic peracid or potassium peroxymonosulfate (OXONE), the latter in aqueous methanol.

The inhibitors described in Scheme 10 are prepared by the following synthetic pathways. The p-nitrophenoxy derivative (101) is reduced with Pd on carbon at room temperature in a $H_2$ atmosphere to yield the p-amino-phenoxy derivative (102). The amine is then acylated with acetyl chloride in methylene chloride in the presence of pyridine to yield the p-acetylaminophenoxy derivative (103), or likewise treated with benzoyl chloride to yield the corresponding p-benzoylamino analog (104). Alternately, the amino compound (102) is treated with tosyl chloride to yield the p-tosylamino analog (105).

The inhibitors described in Scheme 11 are prepared as follows. The N-2,4-dimethoxybenzyl protected 16-alcohol (106) is treated with p-fluorochlorobenzene and potassium hydride in dimethylform-amide to yield the p-chlorophenoxy derivative (107), which is then treated with trifluoroacetic acid in methylene chloride to remove the N-2,4-dimethoxybenzyl protecting group to yield (108). This is treated with hydrogen gas and a palladium on carbon catalyst in methanol to dechlorinate the phenyl ring to yield the phenoxy derivative (109). This compound is treated with methyl iodide and sodium hydride in dimethylformamide to methylate the ring nitrogen to yield (112). Alternately, (109) is treated with DDQ and BSTFA in toluene to introduce a double bond at the 1-position to yield (110). Utilizing the same reduction reaction scheme, the 1,2-dihydro androstane (108) yields the p-chloroandrost-1-ene (111). This is then methylated at the 1-position by treatment with methyl iodide, sodium hydride in dimethylformamide to yield (113).

The inhibitors described in Scheme 12 are prepared via similar reaction pathways as described in Scheme 11. The N-2,4-dimethoxybenzyl protected 16-alcohol (106) is treated with 4-methyl-3-chlorofluorobenzene and potassium hydride in dimethylformamide to yield the 4-methyl-3-chlorophenoxy derivative (114), which is then treated with trifluoroacetic acid in methylene chloride to remove the N-2,4-dimethoxybenzyl protecting group to yield (115). This is treated with hydrogen gas and a palladium on carbon catalyst in methanol to dechlorinate the phenyl ring to yield the p-methylphenoxy derivative (116). This compound is treated with methyl iodide and sodium hydride in dimethylformamide to methylate the ring nitrogen to yield (118). Alternately, (116) is treated with DDQ and BSTFA in toluene to introduce a double bond at the 1-position to yield (117).

The inhibitors in Scheme 13 are prepared as follows. The starting 16-alcohol (76) is treated with methanesulfonic acid in pyridine containing DMAP to yield the mesylate (119). This in turn is treated with an appropriate thiophenol in anhydrous THF containing sodium hydride to yield the thiophenoxy (120), 4-chlorothiophenoxy (121), 4-fluorothiophenoxy (122), 4-methylthiophenoxy (127) and the 4-methoxy-thiophenoxy (124) derivatives. Treatment of the thiophenoxy (120) derivative with m-chloroperbenzoic acid in methylene chloride at 0° C. for one hour yields the phenylsulfinyl derivative (125). Treatment of the phenylsulfinyl compound (125) under the same reaction conditions prolonged however for three hours, yields the phenylsulfonyl derivative (126).

The inhibitors for Scheme 14 are prepared as follows. The 16-ketone (62) is treated with an appropriate arylmethyl diethylphosphonate under Wittig conditions using sodium hydride in DMF at 80°–100° C. to yield the corresponding 4-chlorobenzylidene (128), benzylidene (127) and 4-methylbenzylidene (129) analogs. These are reduced in ethanol under a hydrogen atmosphere using a 5% rhodium on carbon catalyst to yield the corresponding 4-chlorobenzyl (130) and 4-methylbenzyl (131) derivatives. The 3-pyridyl-methyl (132) analog is made in the same two step manner.

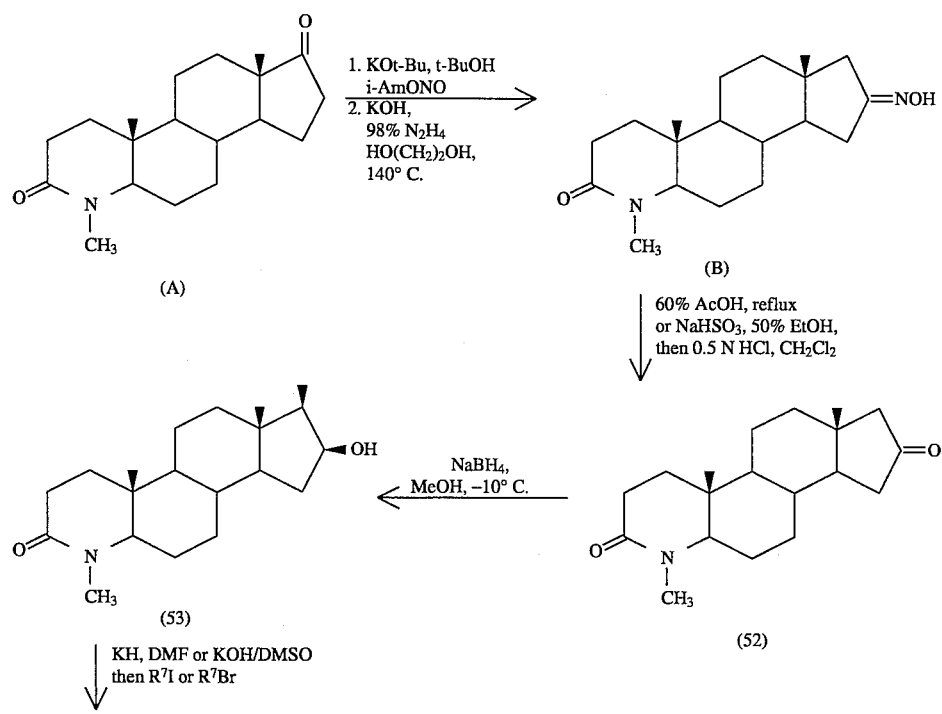

SCHEME 1

-continued
SCHEME 1
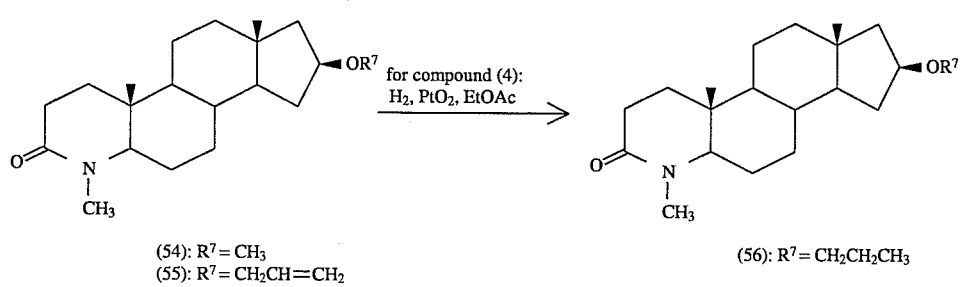
(54): $R^7 = CH_3$
(55): $R^7 = CH_2CH=CH_2$
(56): $R^7 = CH_2CH_2CH_3$
SCHEME 2
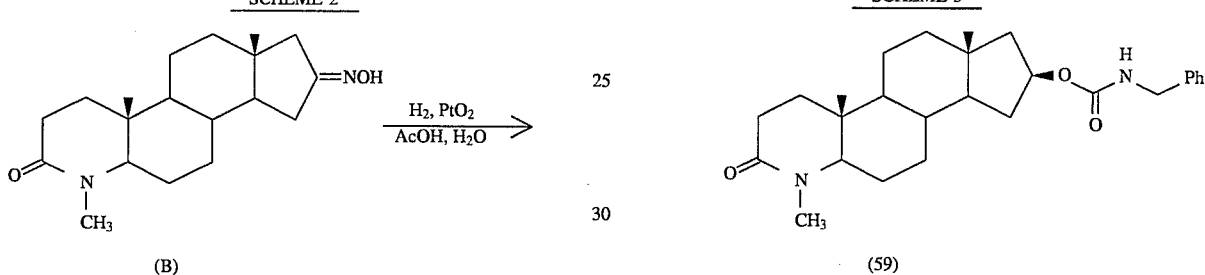
(B)
(C)
(57): $R^8 = CH_3$
(58): $R^8 = Ph$
SCHEME 3
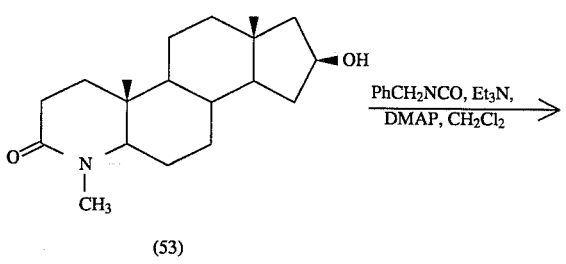
(53)
-continued
SCHEME 3
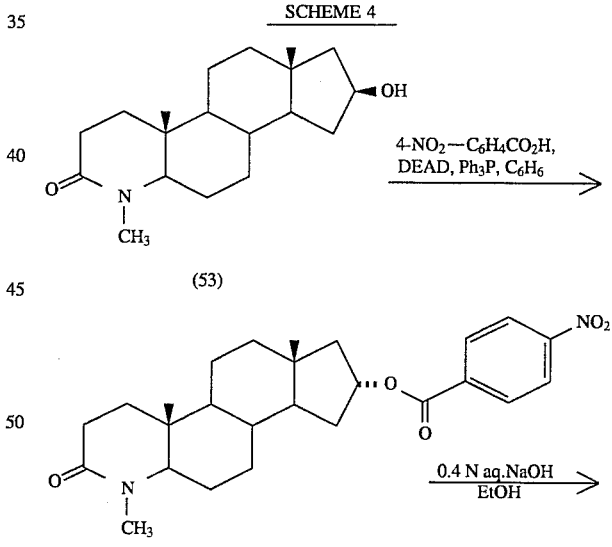
(59)
SCHEME 4
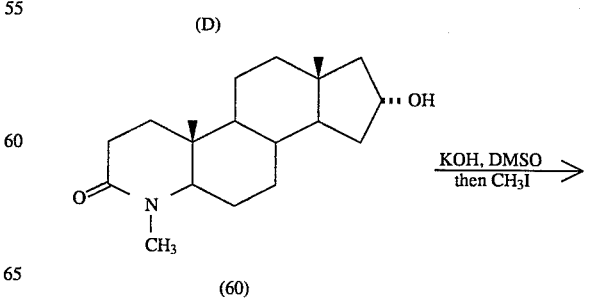
(53)
(D)
(60)

-continued
SCHEME 4
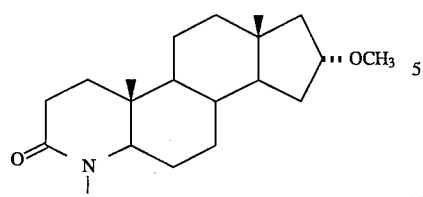
(61)
SCHEME 5
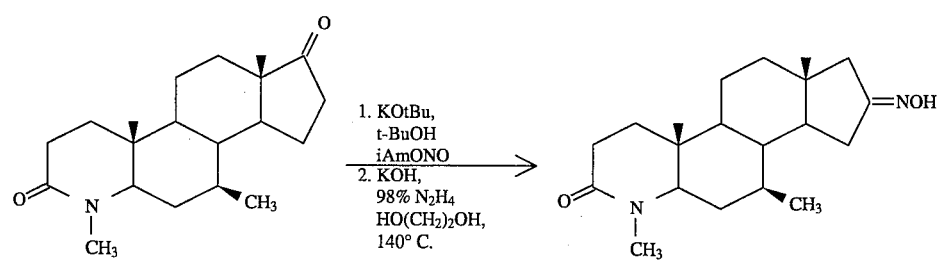
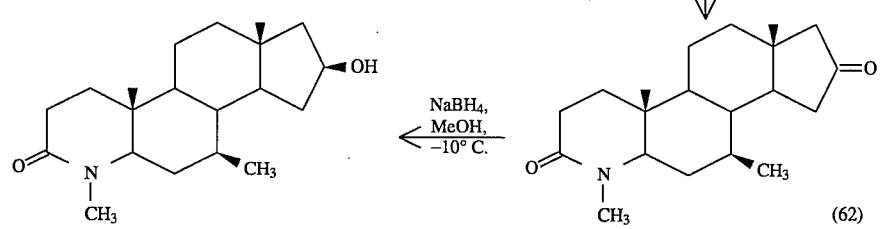
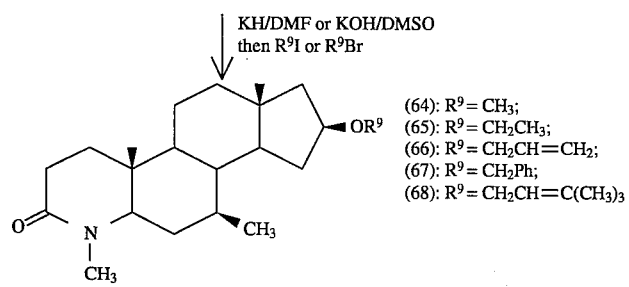
(64): $R^9 = CH_3$;
(65): $R^9 = CH_2CH_3$;
(66): $R^9 = CH_2CH=CH_2$;
(67): $R^9 = CH_2Ph$;
(68): $R^9 = CH_2CH=C(CH_3)_3$
for compound (66):
$H_2$, $PtO_2$, EtOAc;
for compound (68):
$H_2$, 10% Pd(C), EtOAc -continued
SCHEME 5
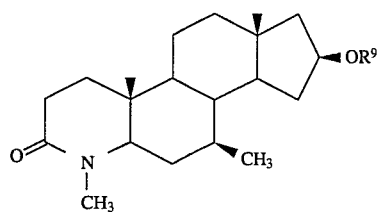
(69): $R^9$ = $CH_2CH_2CH_3$;
(70): $R^9$ = $CH_2CH_2CH(CH_3)_3$
SCHEME 6
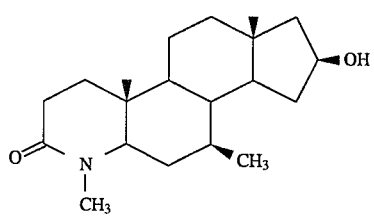
(63)
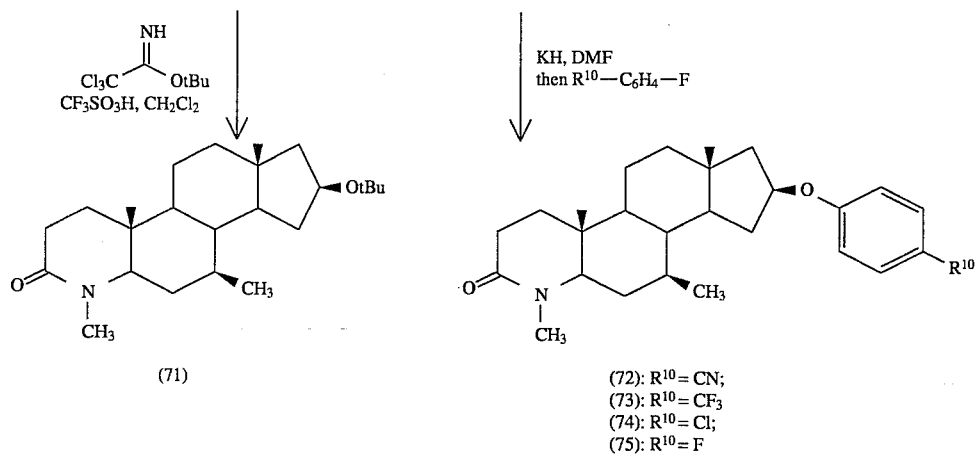
(71)
(72): $R^{10}$ = CN;
(73): $R^{10}$ = $CF_3$
(74): $R^{10}$ = Cl;
(75): $R^{10}$ = F
SCHEME 7
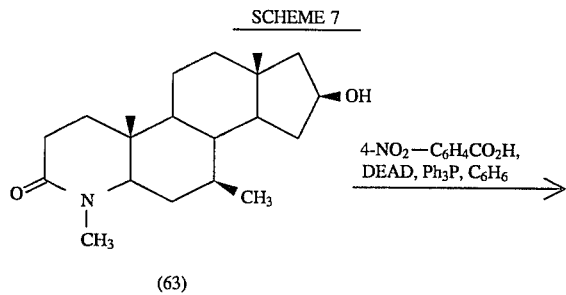
(63)
$\xrightarrow{\text{4-NO}_2\text{—C}_6\text{H}_4\text{CO}_2\text{H,}\\ \text{DEAD, Ph}_3\text{P, C}_6\text{H}_6}$
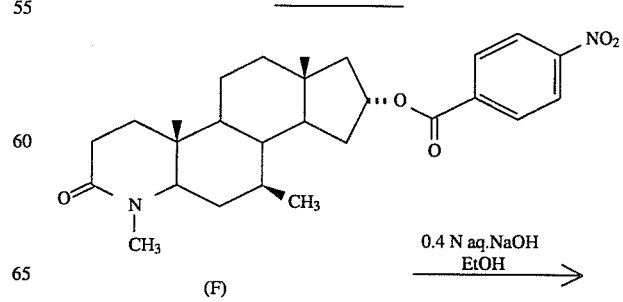
(F)
$\xrightarrow{\text{0.4 N aq.NaOH}\\ \text{EtOH}}$
-continued
SCHEME 7

45
-continued
SCHEME 7
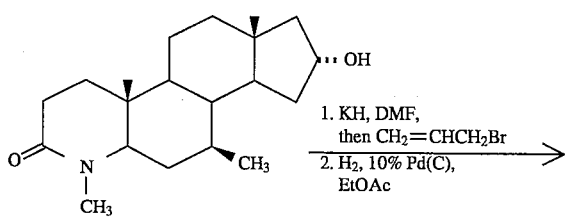
(76)
1. KH, DMF, then CH$_2$=CHCH$_2$Br
2. H$_2$, 10% Pd(C), EtOAc
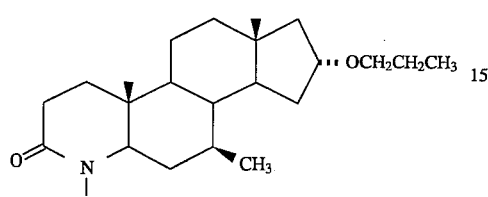
(77)
SCHEME 8
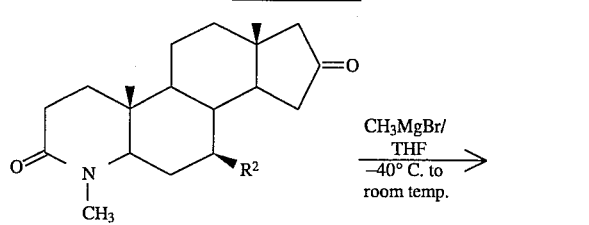
R$^2$ = H or CH$_3$
CH$_3$MgBr/ THF
−40° C. to room temp.
46
-continued
SCHEME 8
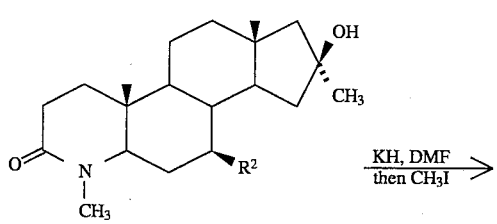
(78): R$^2$ = H
(79): R$^2$ = CH$_3$
KH, DMF then CH$_3$I
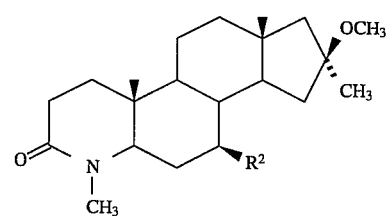
(80): R$^2$ = H;
(81): R$^2$ = CH$_3$
SCHEME 9
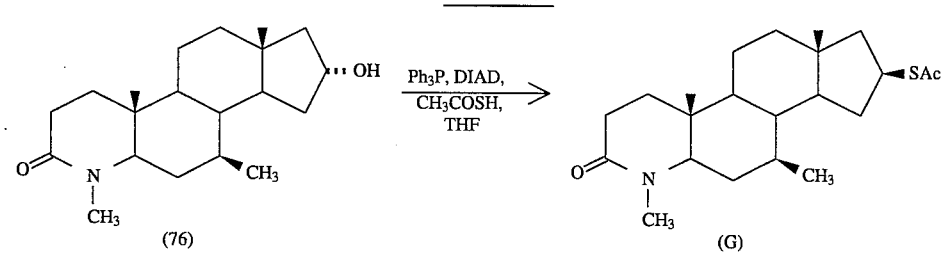
(76)  Ph$_3$P, DIAD, CH$_3$COSH, THF  (G)
0.4 N NaOH, EtOH

SCHEME 9 -continued
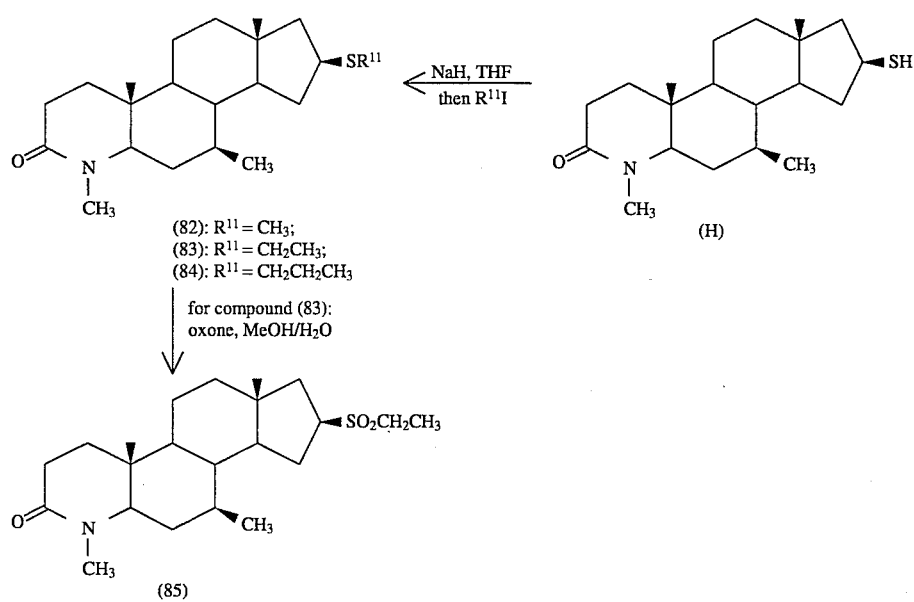
(82): R[11] = CH_3;
(83): R[11] = CH_2CH_3;
(84): R[11] = CH_2CH_2CH_3
for compound (83):
oxone, MeOH/H_2O
(H)
(85)
SCHEME 10
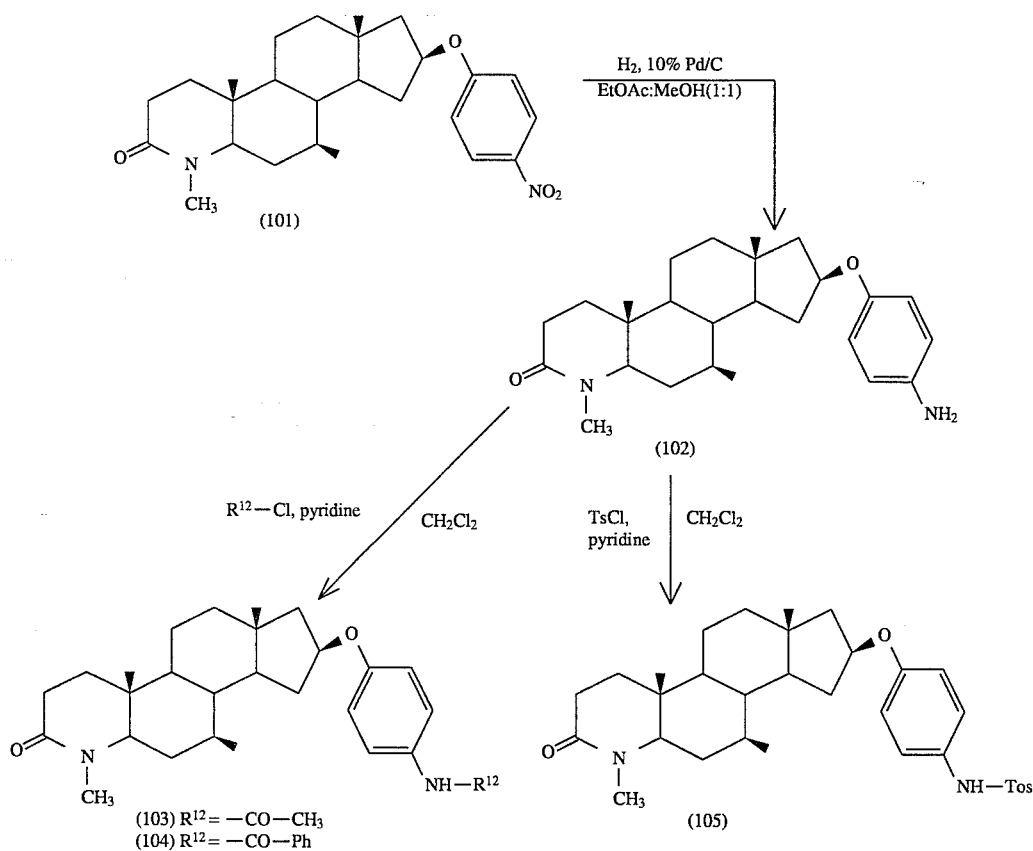
(101)
(102)
(103) R[12] = —CO—CH_3
(104) R[12] = —CO—Ph
(105)

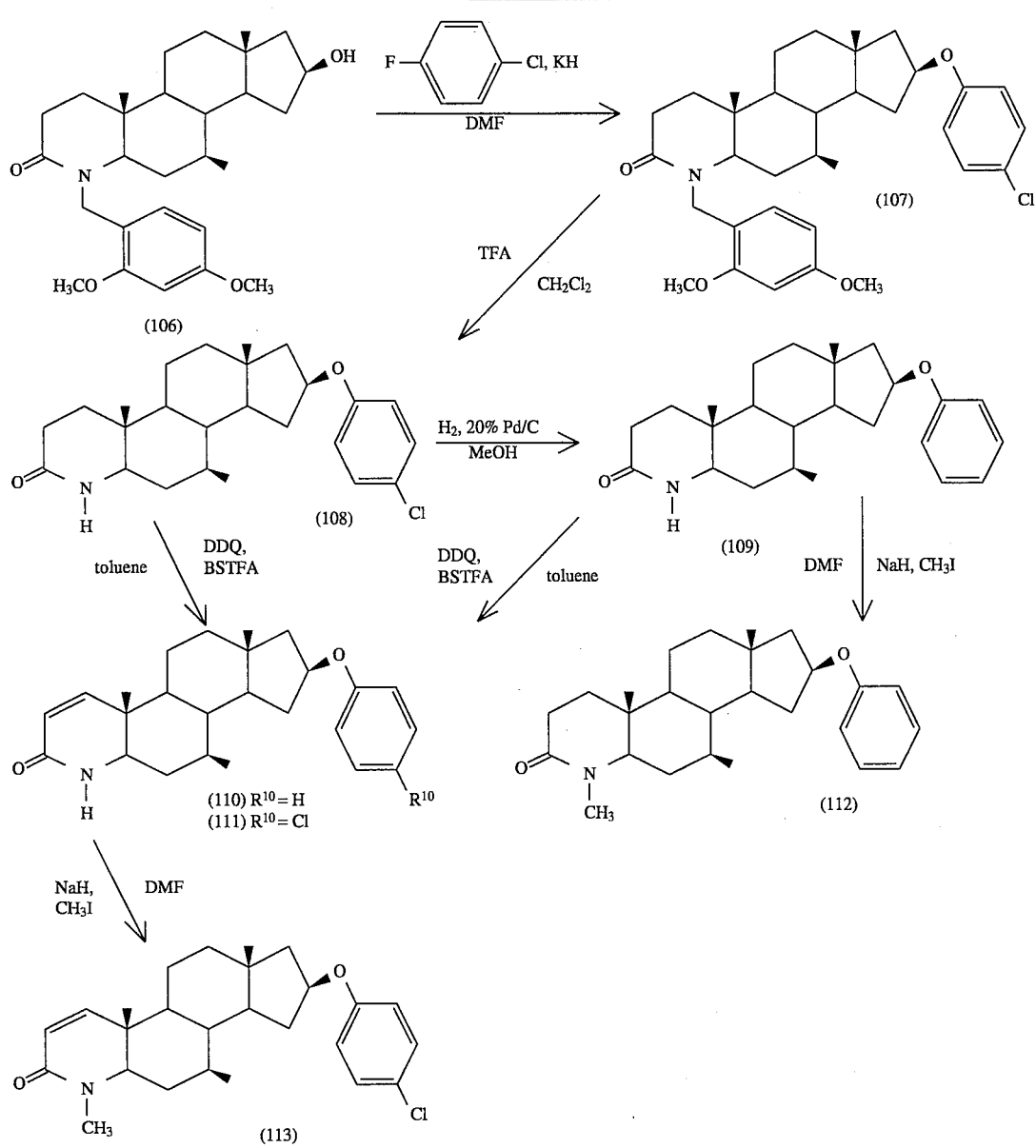

5,543,417
51 52
SCHEME 12
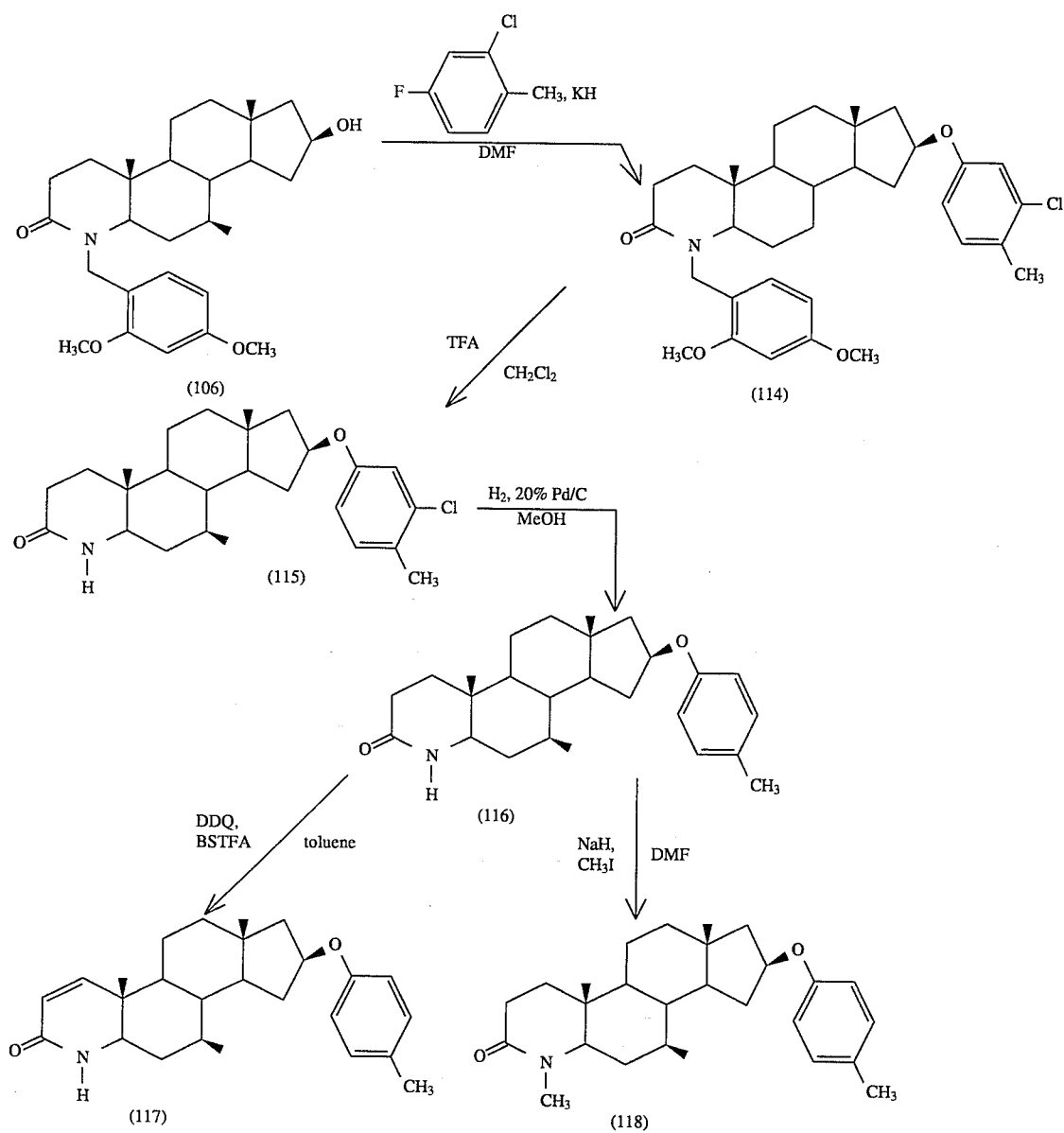
SCHEME 13
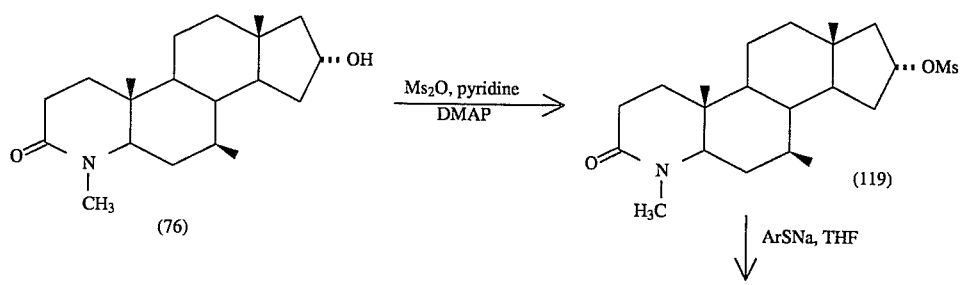

-continued
SCHEME 13

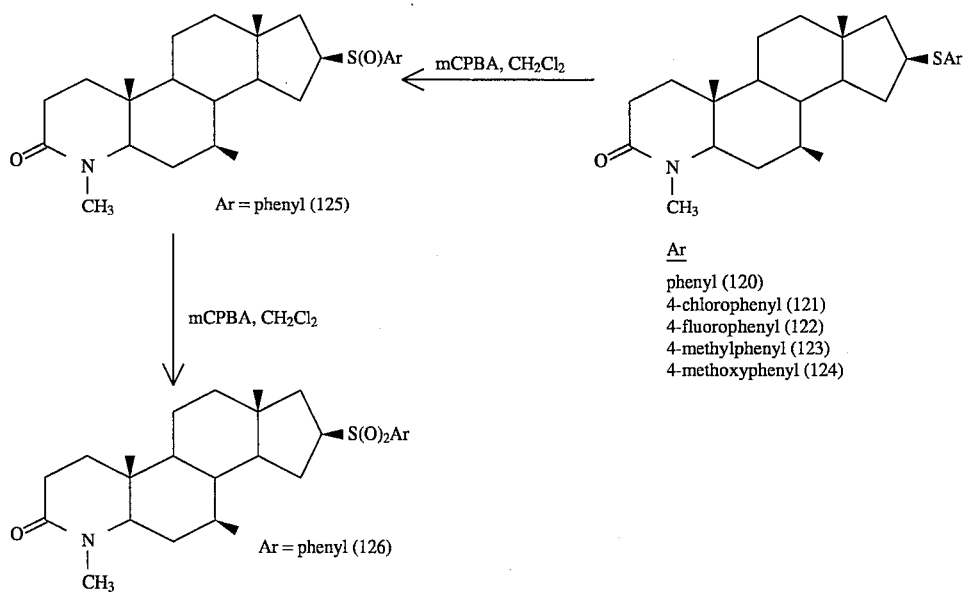

Ar phenyl (120)
4-chlorophenyl (121)
4-fluorophenyl (122)
4-methylphenyl (123)
4-methoxyphenyl (124)

SCHEME 14

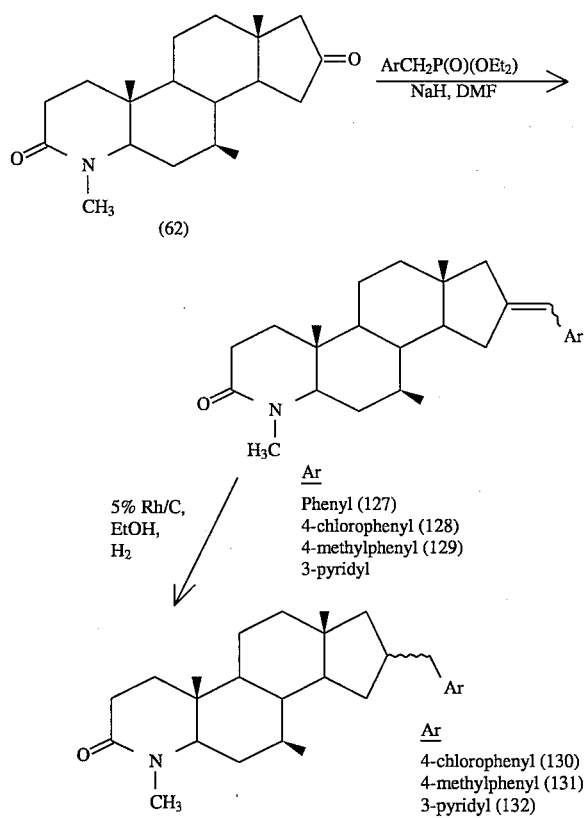

In another embodiment of this invention there is provided a combination method involving the use of a 5α-reductase 1 and/or 2 inhibitor, in combination with at least one agent selected from: an antibacterial, an anti-inflammatory, and a keratolytic, or combination thereof, in the prevention of acne vulgaris by topical and/or systemic administration The activity of the compounds as selective 5α-reductase 1 or 2 inhibitors, or dual inhibitors, can be determined by the following Biological assays:

BIOLOGICAL ASSAYS

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

Cloned enzyme protocol:

For $IC_{50}$ determinations, the test 5α-reductase 1 and 2 inhibitors were dissolved in ethanol and serially diluted to the appropriate concentration. The baculovirus-expressed recombinant type 15α-reductase was preincubated with inhibitor (0.1–1,000 nM) in 40 mM sodium phosphate, pH 7.0, 500 gM NADPH, 1 mM DTT and 1 mg/ml BSA for 18 h at 4° C. The reaction was initiated by the addition of [7-$^3$H]T (NEN, 20 Ci/mmol) and NADPH to a final concentration of 0.3 μM and NADPH and incubated at 37° C. for 90 min. Similarly, baculovirus-expressed type 2 5α-reductase was preincubated with inhibitor (1–10,000 nM) in 40 mM sodium citrate, pH 5.5, 500 μM NADPH, 1 mM DTT and 1 mg/ml BSA for 18 h at 4° C. The reaction was initiated by the addition of [7-$^3$H]T (NEN, 20 Ci/mmol) and NADPH to a final concentration of 0.3 μM and 500 μM, respectively. The conversion of T to DHT was monitored using a radio-flow detector following separation by reverse phase HPLC (Whatman RACII $C_{18}$ column, 1 ml/min 0.1% TFA in water:methanol (42:58); retention times T, 6.3 min, DHT, 9.7 min).

5α-reductase assay

The reaction mixture for the type 1 5α-reductase contained 40 mM potassium phosphate, pH 6.5, 5 μM [7-$^3$H]-testosterone, 1 mM dithiothreitol and 500 μM NADPH in a final volume of 100 μl. The reaction mixture for the type 2 5α-reductase contained 40 mM sodium citrate, pH 5.5, 0.3 μM [7-$^3$H]-testosterone, 1 mM dithiothreitol and 500 μM NADPH in a final volume of 100 μl. Typically, the assay was initiated by the addition of 50–100 μg prostatic homogenate or 75–200 μg scalp homogenate and incubated at 37° C. After 10–50 min the reaction was quenched by extraction with 250 μl of a mixture of 70% cyclohexane: 30% ethyl acetate containing 10 μg each DHT and T. The aqueous and organic layers were separated by centrifugation at 14,000 rpm in an Eppendorf microfuge. The organic layer was subjected to normal phase HPLC (10 cm Whatman partisil 5 silica column s equilibrated in 1 ml/min 70% cyclohexane: 30% ethyl acetate; retention times: DHT, 6.8–7.2 min; androstanediol, 7.6–8.0 min; T, 9.1–9.7 min). The HPLC system consisted of a Waters Model 680 Gradient System equipped with a Hitachi Model 655A autosampler, Applied Biosystems Model 757 variable UV detector, and a Radiomatic Model A120 radioactivity analyzer. The conversion of T to DHT was monitored using the radioactivity flow detector by mixing the HPLC effluent with one volume of Flo Scint 1 (Radiomatic). Under the conditions described, the production of DHT was linear for at least 25 min. The only steroids observed with the human prostate and scalp preparations were T, DHT and androstanediol.

Inhibition studies

Compounds were dissolved in 100% ethanol. $IC_{50}$ values represent the concentration of inhibitor required to decrease enzyme activity to 50% of the control. $IC_{50}$ values were determined using a 6 point titration where the concentration of the inhibitor was varied from 0.1 to 1000 nM.

A compound referred to herein as a 5α-reductase 1 inhibitor is a compound that shows inhibition of the 5α-reductase lisozyme in the above-described assay, having an $IC_{50}$ value of about or under 600 nM.

A compound referred to herein as a 5α-reductase 2 inhibitor is a compound that shows inhibition of the 5α-reductase 2 isozyme in the above-described assay, having an $IC_{50}$ value of about or under 600 nM.

A compound referred to herein as a dual 5α-reductase 1 and 2 inhibitor is a compound that shows inhibition of both the 5α-reductase 1 and 2 isozymes in the above-described assay, having an $IC_{50}$ value for each of type 1 and type 2 of about or under 600 nM, and preferably 100 nM.

Fuzzy Rat Acne Model

Adult fuzzy rats are a variety of rat that has stunted hair growth, brown colored seborrhea covering their entire back skin and abnormally increased sebum production after puberty that has been demonstrated to be due to circulating androgens. 0.1, 0.05 and 0.025% solutions of a selected 5α-reductase inhibitor of interest are prepared in a vehicle of propylene glycol, isopropanol, isopropyl myristate and water (50/30/2/18%), and is topically applied onto the backs of adult male fuzzy rats, 0.2 ml per animal daily for 4 weeks. Controls receive the vehicle alone and 5 of them are castrated. After 2 weeks seborrhea will be dose-dependently depleted and after 4 weeks bromodeoxyuridine (BrdU, 200 mg/kg) is intraperitoneally injected 2 hours before sacrifice. The skin tissues are incubated with EDTA (20 mM) in phosphate buffer, 1.5 hours at 37° C. The pilo-sebaceous unit attached to the epidermis is striped from the dermis and fixed with formalin for immuno-staining of BrdU. DNA synthesis cells showing a BrdU-positive nucleus are located in the outer glandular border. The number of S-phase cells per lobe is determined with a micro-image apparatus. Using formalin fixed skin, frozen serial sections are stained with 1% osmium and the size of the lobes is measured. A positive inhibitor of skin 5α-reductrase will induce suppression of sebum production by inhibiting the rate of glandular cell turnover, and showing reduced lobular size.

Representative compounds of Formulas I and II were tested in the above described inhibition assay for 5α-reductase type 1 and type 2 inhibition. For the inhibition of 5α-reductase type 1, the compounds have $IC_{50}$ values lower than 600 nM, with the majority of compounds in general having $IC_{50}$ values ranging from about 0.3 nM to about 200 nM. For the inhibition of 5α-reductase type 2, the same compounds have $IC_{50}$ values greater than about 155 nM, with the majority of compounds having $IC_{50}$ values greater than 1000 nM. The compounds in general have at least a 2-fold greater selectivity for inhibition of 5α-reductase type 1 over type 2, with the majority of the compounds having a 10-fold or greater selectivity for inhibition of 5α-reductase type 1 over type 2. These results demonstrate the utility of the compounds of the instant invention for the treatment of hyperandrogenic conditions.

A compound referrred to herein as a 5α-reductase 1 inhibitor is a compound that shows inhibition of the 5α-reductase 1 isozyme in the above-described assay.

A compound referrred to herein as a 5α-reductase 2 inhibitor is a compound that shows inhibition of the 5α-reductase 2 isozyme in the above-described assay.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carders, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

Antibacterials useful in the instant invention are active against various bacteria which are associated with acne and include Gram-positive and Gram-negative classes of bacteria. One particular bacteria which is associated with acne is *Propionibacterium acne*.

The antibacterial can be selected from the classes of aminoglycosides, amphenicols, ansamycins, beta-lactams including carbapenems, cephalosporins, cephamycins, monobactams, oxacephems, penicillins; lincosamides, macrolides, polypeptides, tetracyclines, 2,4,-diaminnopyrimidines, nitrofurans, quinolones, sulfonamides, sulfones, and other structural types.

Specific antibacterials which are non-limiting are listed in *The Merck Index, Eleventh Edition*, 1989, (published by Merck & Co. Inc.) and include the following:

Aminoglycosides:

amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, streptonicozid, tobramycin Amphenicols:

azidamfenicol, chloramphenicol, chloramphenicol palmitate, chloramphenicol pantothenate, florfenicol, thiamphenicol Ansamycins:

rifamide, rifampin, rifamycin SV, rifaximin

Beta-Lactams:

Carbapenems:

imipenem

Cephalosporins:

cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, pivcefalexin Cephamycins:

cefbuperazone, cefmetazole, cefminox, cefotetan, cefoxitin

Monbactams:

aztreonam, carumonam, tigemonam

Oxacephems:

flomoxef, moxolactam

Penicillins:

amidinocillin, amidinocillin pivoxil, amoxicillin, ampicillin, apalcillin, aspoxicillin, azidocillin, azlocillin, bacampicillin, benzylpenicillinic acid, benzylpenicillin sodium, carbenicillin, carfecillin sodium, carindacillin, clometocillin, cloxacillin, cyclacillin, dicloxacillin, diphenicillin sodium, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, talampicillin, temocillin, ticarcillin Lincosamides:

clindamycin, lincomycin

Macrolides:

azithromycin, carbomycin, clarithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin Polypeptides:

amphomycin, bacitracin, capreomycin, colistin, enduracidin, enviomycin, fusafungine, gramicidin(s), gramicidin S, mikamycin, polymyxin, polymyxin B-methanesulfonic acid, pristinamycin, ristocetin, teicoplanin, thiostrepton, tuberactinomycin, tyrocidine, tyrothricin, vancomycin, viomycin, viomycin pantothenate, virginiamycin, zinc bacitracin Tetracyclines:

apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin, tetracycline 2,4-Diaminopyrimidines:

brodimoprim, tetroxoprim, trimethoprim

Nitrofurans:

furaltadone, furazolium chloride, nifuradene, nifuratel, nifurfoline, nifurpirinol, nifurprazine, nifurtoinol, nitrofurantoin Ouinolones:

amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, pefloxacin, pipemidic acid, piromidic acid, rosoxacin, temafloxacin, tosufloxacin, OPC 7251(Otsuka) a fluoroquinolone Sulfonamides:

acetyl sulfamethoxypyrazine, acetyl sulfisoxazole, azosulfamide, benzylsulfamide, chloramine-B, chloramine-T, dichloramine-T, formosulfathiazole, N-formylsulfisomidine, N-beta-D-glucosylsulfanilamide, mafenide, 4'-(methylsulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, s sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, N-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole Sulfones:

acedapsone, acediasulfone, acetosulfone sodium, dapsone, diathymosulfone, glucosulfone sodium, solasulfone, succisulfone, sulfanilic acid, p-sulfanilylbenzylamine, p,p'-sulfonyldianiline-N,N'-digalactoside, sulfoxone sodium, thiazolsulfone Others:

cycloserine, mupirocin, tuberin, clofoctol, hexedine, methenamine, methenamine anhydromethylene-citrate, methenamine hippurate, methenamine mandelate, methenamine sulfosalicylate, nitroxoline, xibornol and benzoyl peroxide.

Very useful antibacterials in the invention method are the following: clindamycin, erythromycin, teracycline, benzoyl peroxide meclocycline, chloramphenicol, neomycin, metronidazole, and OPC 7251 (Otsuka).

Keratolytic agents useful in the instant invention in some instances are active as bactericidal agents that can be used for the treatment of mild acne, e.g., salicylic acid. By the term "keratolytic agent" as used herein is meant a compound that displays properties of a keratolytic and can in some instances also display properties of an antibacterial, e.g., benzoyl peroxide. Keratolytics act by improving inflammatory and/or noninflammatory acne lesions by reducing the population of *P. acnes* and facilitating a decrease in hyperkeratosis.

Specific keratolytics which are non-limiting are listed in The Merck Index, Eleventh Edition, 1989, (published by Merck & Co. Inc.) and include the following: algestone acetophenide, azelaic acid, cyoctol, dichloroacetic acid, metronidazole, motretinide, resorcinol, salicylic acid, sulfur, tetroquinone, and alpha-hydroxy acids including glycolic acid.

Very useful keratolytics in the invention method are the following: azelaic acid, salicylic acid, and glycolic acid.

Anti-inflammatories useful in the instant invention are active against inflammation caused by various bacteria which are associated with acne and include Gram-positive and Gram-negative classes of bacteria. One particular bacteria which is associated with acne is *Propionibacterium acne*.

The anti-inflammatory can be steroidal or non-steroidal. The non-steroidal anti-inflammatory can be selected from the classes of aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, and other structural types.

Specific non-steroidal anti-inflammatories which are non-limiting are listed in The Merck Index, Eleventh Edition, 1989, (published by Merck & Co. Inc.) and include the following:

Aminoarylcarboxylic acid derivatives:

enfenamic acid, etofenamate, flufenamic acid, isonixin, meclofenamic acid, mefenamic acid, nifiumic acid, talnifiumate, terofenamate, tolfenamic acid Arylacetic acid derivatives:

acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin, zomepirac Arylbutyric acid derivatives:

bumadizon, butibufen, fenbufen, xenbucin

Arylcarboxylic acids:

clidanac, ketorolac, tinoridine

Arylpropionic acid derivatives:

alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen, tiaprofenic acid Pyrazoles:

difenamizole, epirizole

Pyrazolones:

apazone, benzpiperylon, feprazone, mofebutazone, morazone, oxyphenbutazone, phenylbutazone, pipebuzone, propyphenazone, ramifenazone, suxibuzone, thiazolinobutazone Salicylic acid derivatives:

acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acid, salicylsulfuric acid, salsalate, sulfasalazine Thiazinecarboxamide derivatives:

droxicam, isoxicam, piroxicam, tenoxicam

Other Structural Types:

epsilon-acetamidocaproic acid, S-adenosylmethionine, 3-ámino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, tenidap Specific steroidal anti-inflammatories are listed in The Merck Index, Eleventh Edition, 1989, (published by Merck & Co. Inc.) and include the following:

Glucocorticoids:

21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethaxsone, diflorasone, diflucortolone, defluprednate, enoxolone, fluazacort, flucloronide, flumethasone, flunisolide, fluocinolone acetonide, fluocinonide, fluocortin butyl, fluocortolone flujorometholone, fluperolone acetate, fluprednidene acetat, fluprednisolone, flurandrenolide, formocortal, halcinonide, halometasone, halopredone acetate, hydrocortamate, hydrocortisone, hydrocortisone acetate, hydrocortisone phosphate, hydrocortisone 21-sodium succinate, hydrocortisone tebutate, maziprednone, medrysone, meprednisone, methylprednisonole, mometasone furoate, paramethasone prednicarbate, prednisolone, prednisolone 21-diethylaminoacetate, prednisolone sodium phosphate, prednisolone sodium succinate, prednisolone sodium 21-m-sulfobenzoate, prednisolone 21-stearoylglycolate, prednisolone tebutate, prednisolone 21-trimethylacetate, prednisone, prednival, prednylidene, prednylidene 21-diethylaminoacetate, tixocotrol, triamcinolone, triamcinolone acetonide, triamcinolone benetonide, triamcinolone hexacetonide.

Very useful anti-inflammatories in the invention method are the following:glucocorticoids, including prednisone, prednisolone and the like.

The 5 alpha reductase 1 or 2 inhibitor, or mixture thereof, anti-flammatory, keratolytic and anti-inflammatory can each be administered orally, systemically or topically, as separate or concurrent dosage forms, or together as one formulation. A useful protocol is the use of the anti-inflammatory, keratolytic and antibacterial topically and the use of the 5 alpha reductase 1 and/or 2 inhibitor orally. For combination treatment where the combination agents are in separate dosage formulations, they can be administered concomitantly, or they each can be administered separately at staggered times.

For example, a compound of Formula I, e.g., 4,7-beta-dimethyl- 4-aza-5-alpha-cholestan-3-one, and antibacterial, i.e., erythromycin, can be administered together in a single topical dosage formulation, or each active agent can be separately administered in a particular dosage formulation, e.g., as a 'separate oral ($5\alpha$-reductase inhibitor) and topical erythromycin dosage formulations, or a topical dosage formulation of the antibacterial in combination with an oral dosage formulation of a compound of Formula I. See, e.g., U.S. Pat. Nos. 4,377,584 and 4,760,071 which describe dosages and formulations for $5\alpha$-reductase inhibitors.

One useful combination is erythromycin benzoyl peroxide, and a $5\alpha$-reductase 1 inhibitor, e.g., 3-oxo-4-aza-4,7$\beta$-dimethyl-16$\beta$-(4-chlorophenoxy)-5$\alpha$-androstane.

In the methods described above, the daily dosage of the 5 alpha reductase 1 inhibitor compounds of Formula I and II may be varied over a wide range from 0.1 mg to 1,000 mg per adult human/per day. An effective amount of one of the novel compounds of this invention is ordinarily from about 0.002 mgs/kg to 50 mgs./kg of body weight per day, and more particularly the range is from about 0.01 mgs/kg to 7 mgs/kg of body weight per day.

The daily dosage of the keratolytic is topically administered in a 0.025% to 0.1% by weight cream or gel.

The daily dosage of the antibacterial systemically is from about one mg to 2000 mg per adult human/per day, and more particularly from about 200 mg to 1000 mg per adult human/per day. The daily amount of antibacterial is from 1 mgs/kg to 50 mgs/kg of human body weight daily.

The daily dosage of the anti-inflammatory topically or systemically is from about 0.01 mg to 2000 mg per adult human/per day, and more particularly from about one mg to 1000 mg per adult human/per day. The daily amount of anti-inflammatory is from 0.02 mgs/kg to 40 mgs/kg of human body weight daily.

For mild to moderate acne, topical daily therapy is generally indicated to avoid the side effects of the more rigorous systemic therapy with its attendant side effects. For moderate to severe acne, systemic therapy is generally used, which can also be combined with topical therapy, where warranted. Duration of therapy, depending on the severity, can last for 3–6 months, and in some cases, for several years.

Advantageously, the combination of the present invention may be administered in a single daily dose, or the total daily dosage may be administered in divided doses of two, three or four times daily. The combination for the present invention can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For the treatment of acne vulgaris, the compounds of the instant invention can also be combined with a therapeutically effective amount of a 5α-reductase 2 inhibitor, such as finasteride, in a single oral, systemic, or parenteral pharmaceutical dosage formulation. Also, for the skin and scalp related disorders of acne vulgaris, the compounds of the instant invention and a 5α-reductase 2 inhibitor can be formulated for topical administration. Alternatively, a combined therapy can be employed wherein the compound of Formula I and the 5α-reductase 2 inhibitor are administered in separate oral, systemic, parenteral or topical dosage formulations. For example, a compound of Formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of Formula I. See, e.g., U.S. Pat. Nos. 4,377,584 and 4,760,07 1 which describe dosages and formulations for 5α-reductase inhibitors. Where the active agents are in separate dosage formulations, they can be administered concomitantly, or they each can be administered at separately staggered times.

Other 5α-reductase 2 inhibitors, both steroidal and non-steroidal, which can be employed in the instant invention include (listed by company of development and publications/patents containing the pertinent disclosure):

STEROIDAL:
SmithKline Beecham (SKB)—*Epristeride* (SK&F 105657)described in PCT applications: WO91/13550, WO 93/19758; 4-aza-unsat'd-steroid- 17-acyl derivatives which are described in WO 94/00121; 17-acyl- 3-carboxyestranes which are described in WO 94/00125; 17-(ar)alkylacyl analogs as dual inhibitors and described in WO94/11386; 17α-acyl-3-carboxysteroids which are described in WO 94/11385;
Sankyo—Japanese Patent J05/170789, which describes 11-oxygenated 4-aza-17-(benzhydrylcarbamoyl) steroids; J05/213987, which describes B-noranalogs; EP 0484094 which discloses 17 -N-(benzhydryl; benzyl carbamoyl) analogs as SKB type inhibitors;
Glaxo—WO93/13124 and U.S. Pat. No. 5,528,589 which describe 4,6-cyclo-6 -aza derivatives; WO 94/14833, which describes 6-aza-17-aryl X compounds, including e.g., anilides;
Farmitalia—*Turosteride*, U.S. Pat. No. 5,155,107 contains the azasteroid disclosure and WO 92/20700 discloses SKB analogs; WO 94/03475 discloses fluorinated amide side-chains; WO 94/03474 and WO 94/03476 disclose 17-carboxamides of α-aminoketones and fluorinated acyl ureas; Great Britain Patent 2,273,096 describes azasteroidal 16,17-piperidinone derivatives;
Ciba-Geigy—EP 0538192, which discloses 4-azasteroidal 17-acyls with cyano substitution;
Richter Gedeon—WO 94/07909, which discloses piperidino/pyrrolidino 4azasteroidal 17carboxamides;
Merrill-Dow—U.S. Pat. Nos 5,143,909, 5,120,840 and 5,130,424, which disclose 4-amino-3-oxo-4-ene steroids; EP 435321, which discloses A-nor-3-carboxysteroids;
NON-STEROIDAL:
Fujisawa—J05/178856, which discloses indolidine-butyric acids; WO 93/05019, which discloses 3,4-disubstd indole derivatives; EP 0519353, which discloses indolizines; WO 93/16996, which discloses 1,3-disubstituted indoles;
Ono—J05140062, which discloses nitro substituents on oxybutric bearing ring;
Kyowa Hakko Kogyo KK—EP 511477, which discloses a 5-substituted indole on an Ono like structure, particularly KF-18678 (Also described by T. Kumazawa, Pharmac. Soc. Japan, 114th Mtg, Abstract 30);
Pfizer—WO 93/02050, which discloses 1,3-disubstituted indole Ono-Fujisawa type compounds;
Yamanouchi—WO 13828, which discloses Ono-like compounds with reversed amide linkages; WO 93/24442 and JP 05331059 which disclose p-substituted benzoic acids;
Mitsubishi Kasei—EP 579223, which discloses benzamide derivatives of 1-amino-6-carboxydecalines; JP 06025211, which discloses flavone-2-benzoic acids; JP 06025277, which discloses 16-ring dilactone tetraenes (Snow Brand Milk Prod Co Ltd.);
Lilly—EP 0532190, 0591582, 0591583) which disclose azaphenanthrenes;
Indena SpA—Extracts of Curcubita seeds disclosed in FR2698791.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

In the methods of the present invention, the combination of 5 alpha reductase 1 and/or 2 inhibitor, antibacterial, keratolytic and anti-inflammatory, herein described in detail, are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

Oral administration can be conducted in the form of a tablet or capsule, the combination drug components can be combined with an oral, non-toxic pharmaceutically acceptable inert carrier such as ethanol, glycerol, water and the like. Capsules containing the combination agents of this invention can be prepared by mixing combination agents of the present invention with lactose and magnesium stearate, calcium stearate, starch, talc, or other carriers, and placing the mixture in gelatin capsule. Tablets may be prepared by mixing the combination ingredients with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. The oral compositions can be provided in the form of scored or unscored tablets containing 0.1, 0.5, 1.0, 2.5, 5.0, 10.0, 15.0, 25.0, 50.0, and 100.0 milligrams of the active ingredients, the 5 alpha reductase 1 inhibitor, tretinoin/isotretinoin, anti-inflammatory, keratolytic, antibacterial, for the symptomatic adjustment of the dosage to the patient to be treated.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 15% by weight each of 5 alpha reductase 1 inhibitor compound, anti-inflammatory, keratolytic, antibacterial in admixture with a pharmaceutically acceptable carrier. Topical preparations containing the combination active drug components can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

Liquid forms of the combination can also be administered in intravenous (both bolus and infusion), intraperitoneal, subcutaneous, topical with or without occlusion, or intramuscular form, all using forms well known to those of ordinary skill in the pharmaceutical arts. The liquid forms can contain suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

The combination agents of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of Structures I and II, of the present invention, can also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The following examples are provided to further illustrate details for the preparation of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds. All temperatures are in degrees Celsius unless noted otherwise.

The Rf values cited were carried out on standard thin layer chromatographic Si gel plates. The elution solvent system used is given in the parentheses following the Rf value.

The fast atom bombardment (FAB) mass spectral values are reported as (M+1) molecular ion peaks, being the molecular weight plus one atomic mass unit. The electron impact (EI) mass spectrum values are reported as molecular ion peaks and are indicated in parentheses, either being (M) or (M+2), the molecular weight, MW, or the MW plus two atomic units.

The nuclear magnetic resonance data was taken at 400 MHz in $CDCl_3$ and is tabulated for unique proton values of each compound at the end of the Examples. The coupling constant J is given in Hertz, Hz.

EXAMPLE 1

Synthesis of 7-Oxo-Cholesterol-3-acetate, (1)

Cholesteryl acetate (CA) is known in the art and can be oxidized to the known 7-oxo-derivative 1 by the analogous procedure described in the JCS Perkins article by Pearson, "supra".

EXAMPLE 2

Synthesis of 7-Ethyl-7-Hydroxy-cholesterol, (2)

To a solution of 1 from Example 1, being 5.0 g (11.32 mmol) in dry tetrahydrofuran at 0° C. was added dropwise 56.6 ml ethyl magnesium bromide (1M) over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield a yellowish-white foam. The Rf value was 0.2 (30% EtOAc/hexane). Proton NMR confirmed the assigned structure of the title compound 2 which was used in the next step without further purification.

EXAMPLE 3

Synthesis of 7-Ethyl-Cholest-4,6-Dien-3-one, (3)

The above Grignard product 2, 5.13 g (11.9 mmol) was dissolved in 50 ml toluene and cyclohexanone and about 40 ml of solvent distilled off under vacuum. To this was added 7.2 g aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, the ethyl acetate layer, washed with brine, dried and purified by column chromatography on silica gel, eluting with 5% EtOAc/hexane to yield the title compound 3. Rf=0.58 (20% EtOAc/hexane). Mass spec: 412(M=1) by FAB, Calc'd. 411.9.

EXAMPLE 4

Synthesis of 7β-ethyl-Cholest-5-en-3-one, (4)

To a solution of 3.1 g of 3, from Example 3, in 46 ml ammonia, 10 ml THF, 10 milliliters toluene, was added 449 mg of metallic lithium in small pieces. After stirring the blue solution for 2 hours at −78° C., a solution of 1,2-dibromethane in 2 ml THF was added. After stirring the solution at −78° C. for 10 minutes, 2.1 g of ammonium chloride was added and the mixture stirred for 10 minutes. The excess ammonia was removed by evaporation under a nitrogen stream. The reaction mixture was diluted with brine, extracted with ethyl acetate. The organic layer was washed with brine, dried and concentrated to yield crude brown viscous liquid 4 which was used as such in Example 5. Rf=0.70 (20% EtOAc/hexane). Mass Spec. 412 (EI); calculated MW 412.70.

EXAMPLE 5

Synthesis of 7β-ethyl-cholest-4-en-3-one, (5)

To a solution of 4, from Example 4, being 3.1 g in 30 ml THF was added 1.1 ml DBU (1,8-diazabicyclo[5.4,0]undec-7-ene under nitrogen with stirring. The mixture was refluxed for 1.5 hours, then cooled and diluted with $NH_4Cl$. Then THF solvent was removed under vacuum and the residue extracted with ethyl acetate. The organic layer was then washed with water, brine, dried and concentrated under reduced pressure to yield a crude viscous oil. The titled product 5 was purified by chromatography on silica gel using 10% EtOAc/hexane as eluant. Mass Spec 412 (EI), calc'd MW 412.70. Rf=0.6 (20% EtOAc/hexane).

EXAMPLE 6

Synthesis of 7-ethyl-17β-(6-methyl-2-heptyl)-5-oxo-A-nor-3,5-secoandrostan-3-oic acid. (6)

To a solution of 1.0 g of 5 in 18 ml t-butyl alcohol at 80° C. was added 300 mg sodium carbonate in 1.8 ml water followed by a dropwise addition over 15–20 minutes of a mixture of 2.74 g sodium periodate with 20.3 mg potassium permanganate in 15 ml water. The reaction mixture was heated at 80° C. for 2 hours, cooled, filtered, the residue washed with water, and then the filtrate concentrated under vacuum, acidified with aqueous HCl, extracted with ethyl acetate and the organic layer washed with aqueous $NaHSO_3$, brine, dried and concentrated to yield crude 6. The proton NMR confirmed the assigned structure. Fast atom bombardment yielded an m/z molecular ion of 434(m+2); calculated 432.69.

EXAMPLE 7

Synthesis of 7-Ethyl-4-methyl-4-aza-cholest-5-en-3-one, (7)

To a solution of 6, 500 mg in 10 ml ethylene glycol was added 1.3 g sodium acetate and 1.0 g methylamine hydrochloride. After stirring the reaction mixture 4 hours at 180° C., the mixture was cooled, diluted with water, extracted with ethyl acetate, dried and concentrated to afford crude title compound 7. Proton NMR confirmed the assigned structure. Rf=0.70 (20% EtOAc/hexane).

Mass Spectral m/z ion (FAB) showed 429 (M+2); calculated, 427.72. Analysis: Calc. for $C_{29}H_{49}NO$ Calcd: C, 81.44; H, 11.55; N, 3.27 Found: C, 82.19; H, 10.92; N, 3.11

EXAMPLE 8

Synthesis of 7-Ethyl-4-methyl-4-Aza-Cholestan-3-one, (8)

To a solution of 7 from Example 7, being 180 mg in 5 ml acetic acid was added 54 mg platinum dioxide and the resulting mixture was evacuated and flushed with hydrogen. The reaction was shaken overnight at room temperature under hydrogen. Filtered, washed solid with EtOAc, combined EtOAc layers were washed with aqueous $NaHCO_3$, brine, dried, concentrated to yield the title compound 8.

Mass spectral analysis by FAB yielded m/z ion of 431 (m+2), calculated 429.74. Analysis for $C_{29}H_{51}NO$ Calcd: C, 81.06; H, 11.96, N, 3.26 Found: C, 81.42; H, 12.24; N, 3.16

EXAMPLE 9

Synthesis of 7-Ethyl-4-Aza-Cholest-5-en-3-one, (9)

The seco acid 6, 0.5 g. and ammonium acetate, 0.5 g, in 3.5 ml acetic acid were refluxed for 3 hours. The reaction mixture was cooled, water added and then extracted with ethyl acetate. The organic layer was dried over sodium sulfate and concentrated to yield a residue which was eluted on a silica gel column with 10% EtOAc/hexane to give pure title compound 9, mp. 147°–149° C.

Mass Spec. 414 (Mtl). Calc'd; 413.69. Rf=0.45 (30% EtOAc/hexane). Analysis for $C_{28}H_{49}NO$, MW 413.69 Calcd: C, 81.30; H, 11.45; N, 3.39 Found: C, 81.30; H, 11.87; N, 3.45

EXAMPLE 10

Synthesis of 7β-Ethyl-4-aza-5α-cholestan-3-one, (10)

Following the general analogous procedure described in Example 8, 9 was catalytically hydrogenated to yield the titled compound, 10. Chromatography on silica gel with 50% EtOAc:hexane eluant yielded pure product, mp. 169°–170° C.

Analysis for $C_{28}H_{49}NO$, MW=415.17. Calcd: C; 80.90; H, 11.88; N, 3.37 Found: C; 81.02; H, 12.57; N, 3.47 Mass Spec.: 416 (M+1) Rf=0.30 (30% EtOAc/hexane).

EXAMPLE 11

Synthesis of 7-Allyl-3,7-dihydroxy-cholest-5-ene, (11)

Following the analogous general Grignard procedure of Example 2, allyl magnesium bromide was reacted with Compound 1 in dry THF to yield the titled product 11. Proton NMR confirmed the assigned structure.

Mass Spec. 441 (M+1). Calc'd. 440.71. Rf=0.25 (30% EtOAc/hexane).

EXAMPLE 12

Synthesis of 7-allyl-cholest-4,6-dien-3-one, (12)

Following the analogous general Oppenauer oxidation procedure of Example 3, compound 11 was oxidized to yield the titled compound 12. Proton NMR confirmed the assigned structure as well the (FAB) mass spec. 423 (M+1) Calc'd. 422.35.

Rf=0.78 (30% EtOAc/hexane).

EXAMPLE 3

Synthesis of 7-Allyl-cholest-5-en-3-one, (13)

Compound 12, was subjected to the analogous metal-ammonia reduction conditions of Example 4 to yield the title compound 13.

Rf=0.5 (5% EtOAc/hexane).

EXAMPLE 14

Synthesis of 7-Allyl-Cholest-4-en-3-one, (14)

Following the general DBU catalyzed isomerization conditions of Example 5, compound 13 was analogously treated to yield the title compound 14.

Mass Spec. 425 (M+1) by FAB. Calc'd.: 424.37 Rf=0.45 (5% EtOAc/hexane).

EXAMPLE 15

Synthesis of 7-Propyl-Cholest-4-en-3-one, (18)

1.0 g of the 7-allyl-enone 14, 5 ml. EtOAc and 50 mg triphenylphosphine rhodium chloride (Wilkinson's catalyst) were allowed to stir two hours (under $H_2$ atmosphere). The reaction products were filtered through 25 ml silica gel, and evaporated to dryness to yield fairly pure title product, 18, as confirmed by proton NMR.

Mass Spec. 427 (M+1) Calc'd.: 426.39 Rf=0.15 (5% EtOAc/hexane).

EXAMPLE 16

Synthesis of 7-propyl-5-oxo-A-nor-3,5-seco-cholestanoic acid, (19)

Following the general procedure of Example 6 for the oxidative Ring A cleavage, compound 18 (7-propyl analogue) was analogously treated to yield the above-titled seco-acid 19. The assigned structure was confirmed by proton NMR.

Mass Spec.: 447 (M+1) (FAB) Calc'd.: 446.38 Rf=0.1 (20% EtOAc/hexane).

EXAMPLE 17

Synthesis of 7-propyl-4-methyl-4-aza-cholest-5-en-3-one, (20)

Following the general procedure of Example 7, compound 19, was analogously treated with methylamine hydrochloride and sodium acetate in ethylene glycol to yield the above-titled liquid product 20. The assigned structure was confirmed by proton NMR.

Mass Spec. 442 (M+1) (FAB), Calc'd.: 441.74 C,H,N analysis for C H N O as $0.2H_2O$, MW=441.74; Calcd: C, 80.91; H, 11.63; N, 3.15 Found: C, 81.00; H, 12.06; N, 2.93 Rf=0.3 (20% EtOAc/hexane).

EXAMPLE 18

Synthesis of 7-Propyl-4-methyl-4-aza-5α-cholestan-3-one, (21)

Following the analogous general procedure of Example 8, compound 20 was catalytically hydrogenated in HOAc to yield the title liquid compound 21. Proton NMR confirmed the assigned structure.

Mass spec. 444 (M+1) (FAB), C,H,N analysis for C H N; Calcd: C, 81.19; H, 12.05; N, 3.16 MW=443.41. Found: C, 80.78; H, 12.06; N, 3.22 Rf=0.17 (20% EtOAc/hexane).

EXAMPLE 19

Synthesis of 7-Propyl-4-aza-cholest-5-en-3-one, (22)

Following the analogous procedure of Example 9, compound 19 was treated with ammonium acetate in acetic acid to yield the titled compound, 22. Recrystallized from EtOAc/$Et_2O$ to yield a white crystalline solid, mp. 91°–94° C., C,H,N analysis as the $0.25H_2O$ hydrate: Calc'd MW 427.39 Calcd: C, 80.59; H, 11.54; N, 3.24 Found: C, 80.59; H, 11.69; N, 3.36 Mass Spec. 428 (M+1).

EXAMPLE 20

Synthesis of 7-Propyl-4-aza-5α-cholestan-3-one, (23)

Following the analogous procedure described in Example 8, compound 22 was catalytically hydrogenated to yield the title compound 23, mp. 65°–68° C.

Analysis for C,H,N, calc'd as 0.25 $H_2O$ hydrate: Calcd: C, 80.21; H, 11.95; N, 3.23 Found: C, 80.20; H, 12.14; N, 3.07 Mass Spec. =430 (M+1) calc'd MW 429.40. Rf=0.12 (20% EtOAc/hexane).

EXAMPLE 21

Synthesis of 7-Methyl-7-Hydroxy-cholesterol, (24)

Following the analogous Grignard procedure of Example 1, cholesteryl acetate-7-one 1 was reacted with methyl magnesium bromide under standard Grignard conditions to yield title compound 24, a solid. NMR confirmed the assigned structure and mass spectral analysis confirmed the molecular weight.

EXAMPLE 22

Synthesis of 7-Methyl-Cholest-4,6-Dien-3-one, (25)

Following the analogous procedure of Example 2, the above Grignard product 24, was subjected to Oppenauer oxidation conditions to yield the title compound, 7β-methyl-cholest-4,6-dien-3-one, 25.

EXAMPLE 23

Synthesis of 7β-methyl-cholest-5-en-3-one, (26)

Following the analogous procedure of Example 4 for the metal-ammonia reduction, 25 was similarly treated with lithium in ammonia/THF/toluene to yield title compound 26.

EXAMPLE 24

Synthesis of 7β-methyl-cholest-4-en-3-one, (27)

Following the general isomerization procedure of Example 5 using DBU in THF, 26 was analogously treated to yield the title compound 27.

EXAMPLE 25

Synthesis of 7-methyl-17β-(2,6-Dimethylhexyl)-5-oxo-A-nor-3,5-Secoandrostan-3-oic acid, (28)

Following the general procedure of Example 6 for the oxidative Ring A cleavage, compound 27 was analogous treated to yield the above titled seco-acid 28. The proton NMR confirmed the assigned structure.

EXAMPLE 26

Synthesis of 7-Methyl-4-aza-cholest-5-en-3-one, (29)

Following the general procedure of Example 9, compound 28 was analogously treated with ammonium chloride in acetic acid to yield the above-titled product 29.

Mass Spectral m/z ion (FB) showed 400.2 (M+1) (M+2).calculated, 399.

EXAMPLE 27

Synthesis of 7-Methyl-4-Aza-Cholestan-3-one, (30)

Following the analogous general procedure of Example 8, compound 29 was catalytically hydrogenated in HOAc to yield the title compound 30.

Mass spectral analysis by EI yielded m/z ion of 401 calculated 401.

EXAMPLE 28

Synthesis of 7-Methyl-4-methyl-4-Aza-Cholest-5-en-3-one, (31)

The seco acid 28, was treated analogously as in Example 7 to give pure title compound 31.

Mass Spec. 414 (m+1) by FAB, calc'd., 413.

EXAMPLE 29

Synthesis of 7β-Methyl-4-methyl-4-aza-5α-cholestan-3-one, (32)

Following the general analogous procedure described in Example 8, 31 was catalytically hydrogenated to yield the titled compound, 32. Chromatography on silica gel with 30% EtOAc/hexane, eluant yielded pure product.

Mass Spec. (EI) 415, calc'd., 415.

EXAMPLE 30

Synthesis of 4-methyl-4-aza-cholest-5-en-3,7-dione, (34)

An oxidation procedure is carried out on 4-methyl-4-aza-cholest- 5-en-3-one 33 to yield the title compound, 34. (See U.S. Pat. No. 3,264,301 by Doorenboos and *J. Org. Chem.* 1961, Vol. 26, p. 4548.) The compound 33 was heated at 70° C. with a mixture of pyridinium dichromate/t-butyl hydroperoxide in benzene over a 3–4 hour period to produce 34.

EXAMPLE 31

Synthesis of 7β-Acetoxy-4-methyl-4-aza-5α-cholestan-3-one, (37)

Compound 34 is hydrogenated by the analogous procedure of Example 8 to produce the 7-H analog 35, and the 7β-ol, 36. Acylation of 36 with acetic anhydride, in the presence of pyridine, 4-dimethylaminopyridine in methylene chloride at 23° C. for 24 hrs. produces the title compound 37.

EXAMPLE 32

Synthesis of 7-Beta Methyl-4-aza-5α-cholest-1-en-3-one, (49)

To a solution of 280 mg (0.698 mmol) of 30 in 4 milliliters toluene, was added 178.8 mg DDQ, 0.7186 mg. BSTFA and 8.163 mg triflic acid and the reaction contents allowed to stir at room temperature for 24 hours. Methyl acetoacetate, 8.1 mg, was added and the reaction refluxed for 24 hours. The contents were cooled, diluted with ethyl acetate, washed with aqueous sodium carbonate, aqueous sodium bisulfite, brine, dried over magnesium sulfate and concentrated to yield an oil. The crude compound was purified by preparative TLC on silica gel, eluting with 3:1 CHCl$_3$/acetone to yield pure 49, whose proton NMR confirmed the assigned structure.

The following Table lists the unique proton NMR values (400 MHz in CDCl$_3$) for each compound. The data are reported as: s=singlet, d=doublet, m=multiplet, J=coupling constant. The absorption values are given in delta (δ) scale with a reference point signal from tetramethylsilane, and are illustrated for the C-18, C-19 and C-21 angular ring methyl protons and protons associated with unique portions of the molecule.

The numbering of the 4-aza steroid is given by the following structure:

TABLE

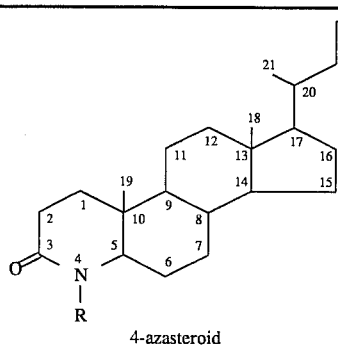

4-azasteroid

| Compound No. | 18-CH₃ | 19-CH₃ | 21-CH₃ | Others |
|---|---|---|---|---|
| 2 | s 0.660 0.662 | s 1.030 1.060 | d 0.940 J = 7 | 6H s 6.120 (values given for second isomer) |
| 3 | s 0.755 | s 1.061 | d 0.915 J = 7 | 4H and 6H s 5.61, 5.97 |
| 4 | s 0.720 | s 1.110 | d 0.930 J = 7 | 4 CH₂ m 2.83–3.28 |
| 5 | s 0.730 | s 1.12 | d 0.930 J = 7 | 4H s 5.74 |
| 6 | s 0.66 | s 0.963 | d 0.894 J = 7 | |
| 7 | s 0.692 | s 0.977 | d 0.908 J = 7 | N—CH₃ s 3.153 |
| 8 | s 0.690 | s 0.830 | d 0.900 J = 7 | N—CH₃ s 2.93 |
| 9 | s 0.653 | s 0.991 | d 0.903 J = 7 | 6H d 4.91 J = 4 |
| 10 | s 0.675 | s 0.808 | d 0.893 J = 7 | 5H, m, 2.97–3.13 |
| 11 | s 0.66 | s 0.90 | d 0.915 J = 7 | allylic H m(5.8–5.94) |
| 12 | s 0.78 | s 1.07 | d 0.96 J = 7 | allylic H m(5.73–5.85) |
| 13 | s 0.70 | s 1.08 | d 0.90 J = 7 | 6H, s (5.23) |
| 14 | s 0.73 | s 1.13 | d 0.93 J = 7 | 4H s 5.72 |
| 18 | s 0.71 | s 1.13 | d 0.93 J = 7 | 4H s 5.71 |
| 19 | s 0.65 | s 0.963 | d 0.91 J = 7 | |
| 20 | s 0.691 | s 0.974 | d 0.902 J = 7 | (6H) - d, 4.92 (J = 4) (N—CH₃) s 3.16 |
| 21 | s 0.665 | s 0.795 | d 0.883 J = 7 | (N—CH₃) s 2.92 5H m (2.96–3.00) |
| 22 | s 0.680 | s 1.01 | d 0.890 J = 7 | (6H) d 4.86 J = 4 |
| 23 | s 0.680 | s 0.808 | d 0.884 J = 7 | 5H m (3.0–3.1) |
| 24 | s, 0.68, 0.69 | s, 0.94, 1.04 | d 0.91 J = 7 | 6H, s, 5.19, 5.21 |
| 25 | s, 0.76 | s, 1.07 | d 0.92 J = 7 | 4H, 6H 5.59, 5.92 |
| 27 | s, 0.70 | s, 1.15 | d 0.92 J = 7 | 7-CH₃, d, 1.04, J = 6.5 4H, s, 5.71 |
| 28 | s, 0.69 | s, 1.12 | d 0.92 J = 7 | 7-CH₃, d, 0.96, J = 6.5 |
| 29 | s, 0.69 | s, 1.04 | d 0.91 J = 7 | 7-CH₃, d, 0.97, J = 6.5 6H, d, 4.59, J = 3.0 |
| 30 | s, 0.67 | s, 0.835 | d 0.91 J = 7 | 7-CH₃, d, 1.00, J = 6.5 5H, dd, J = 3.3, 12.63 |

TABLE-continued

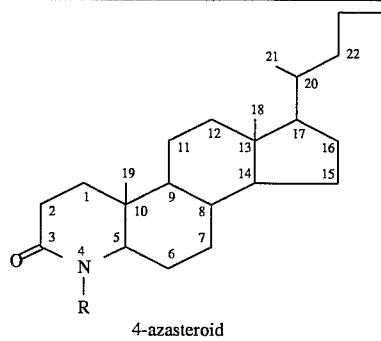

4-azasteroid

| Compound No. | 18-CH₃ | 19-CH₃ | 21-CH₃ | Others |
|---|---|---|---|---|
| 31 | s, 0.69 | s, 1.00 | d 0.95 J = 7 | 7-CH₃, d, 1.05, J = 6.5 6H, d, J = 3.0 |
| 32 | s, 0.68 | s, 0.825 | d 0.91, J = 7H | 7-CH₃, d, 1.05, J = 6.5 4-CH₃, s, 3.92 |
| 33 | s, 0.69 | s, 1.23 | d 0.91 J = 7 | C6 - s, 5.42 N—CH₃, s, 3.14 Mass Spec (EI) = 413 |
| 49 | s, 0.69 | s, 0.90 | d 0.915 J = 7 | C-7CH₃, 1.02, d, J = 6, C-2, 1H, 5.79, dd J = 2.5 J = 9.1 |
| 50 | s, 0.62 | s, 1.01 | d 0.86 J = 7 | C-5, 1H, 3.08, dd J = 3.87 J = 12.9 C-7Ph, 5H, m, 7.1–7.3 |
| 51 | s, 0.63 | s, 1.02 | d 0.8 J = 7 | C-5, 1-H, 3.2, dd J = 5.88 J = 10.5 C-7Ph, 5H, m, 7.08–7.3 |

Examples for Formula II

The starting material 4-aza-4-methyl-5α-androstan-3,17-dione (Compound A in Scheme 1 above, for Formula II) can be made according to the methods described in Rasmusson, et al., *J. Med. Chem.*, 27, p. 1690–1701 (1984). The starting material 4-aza-4,7β-dimethyl-5α-androstan-3,17-dione can be synthesized according to the procedure described in Example 33, below.

EXAMPLE 33

4-Aza-4-methyl-5α-androstan-3,16-dione

Step 1: 4-aza-4-methyl-5α-androstan-3,17-dione-16-oxime

To 2-methyl-2-propanol (14 mL) in a round-bottom flask under a stream of nitrogen gas was added potassium tert-butoxide (740 mg, 6.59 mmol). After complete solution was achieved, 4-aza-4-methyl-5α-androstan-3,17-dione (1.0 g, 3.30 mmol) was added and stirring was continued for 1 hour affording a gold-colored solution. To the reaction mixture was added dropwise with stirring isoamyl nitrite (0.884 mL, 6.58 mmol), and stirring was continued overnight at room temperature affording a deep-orange solution. The mixture was then diluted with an equal volume of water and acidified to pH~2 with 2N hydrochloric acid. Diethyl ether was added, and the solid that formed was filtered, washed with ether, and dried in vacuo, to yield the title compound.

Step 2: 4-aza-4-methyl-5α-androstan-3-one-16-oxime (B)

To a mixture of 4-aza-4-methyl-5α-androstan-3,17-dione-16-oxime (596 mg, 1.79 mmol) in ethylene glycol (5 mL) were added 98% hydrazine (57 μL, 1.74 mmol) and powdered potassium hydroxide (568 mg, 10.12 mmol). The mixture was heated for 16 h at 140°, cooled, and neutralized with 2N hydrochloric acid. The resulting solid was filtered, washed with water, and dried in vacuo to yield the title compound; mass spectrum: m/z 318(M).

Step 3: 4-aza-4-methyl-5α-androstan-3,16-dione, (152)

A mixture of 4-aza-4-methyl-5α-androstan-3-one-16-oxime (218 mg, 0.684 mmol) and sodium bisulfite (249 mg, 23.9 mmol) in 50% aqueous ethanol (10 mL) was heated for 3 h at reflux temperature. Dilute hydrochloric acid (0.5N, 33 mL) and methylene chloride (50 mL) were added, and the mixture was vigorously agitated for several minutes. The organic layer was separated and washed with sodium hydrogencarbonate solution, saturated brine solution, dried ($Na_2SO_4$), and evaporated. The desired product was purified by flash silica gel chromatography using 15% acetone/methylene chloride as eluant to yield the title compound; FAB mass spectrum: m/z 304 (M+1).

400 MHz $^1$H NMR ($CDCl_3$): δ0.89 (s, 3H); 0.91 (s, 3H); 2.90 (s, 3H); and 3.05 (dd, 1H).

EXAMPLE 34

3-Oxo-4-aza-4-methyl-16β-hydroxy-5α-androstane (53)

A solution of 4-aza-4-methyl-5α-androstan-3,16-dione (100 mg, 0.330 mmol) in methanol (2 mL) was cooled in an ice bath and treated with sodium borohydride (38 mg, 0.989 mmol) for 1 h. The reaction mixture was diluted with water and extracted with methylene chloride (2×20 mL). The combined organic extracts were washed with saturated brine solution, dried ($Na_2SO_4$), and evaporated. The desired product was purified by flash silica gel chromatography using 10% acetone/methylene chloride as eluant to yield the title compound; FAB mass spectrum: m/z 306 (M+1).

400 MHz $^1$H NMR ($CDCl_3$): δ0.88 (s, 3H); 0.95 (s, 3H); 2.90 (s, 3H); 3.00 (dd, 1H); and 4.39 (m, 1H).

EXAMPLE 35

3-Oxo-4-aza-4-methyl-16β-methoxy-5α-androstane (54)

To a solution of 3-oxo-4-aza-4-methyl-16β-hydroxy-5α-androstane (35 mg, 0.115 mmol) in dimethyl sulfoxide (1.0 mL) was added powdered potassium hydroxide (32 mg, 0.575 mmol). After stirring for 15 min at room temperature under an nitrogen atmosphere, iodomethane (36 μl, 0.575 mmol) was added and stirring was continued for a further 4 hours. The mixture was diluted with diethyl ether (30 mL), which was washed with water, saturated brine solution, dried ($Na_2SO_4$), and evaporated. The desired product was purified by flash silica gel chromatography using 10% acetone/methylene chloride as eluant to yield the title compound; mass spectrum: m/z 391 (M).

400 MHz $^1$H NMR ($CDCl_3$): δ0.88 (s, 6H); 2.90 (s, 3H); 3.00 (dd, 1H); 3.21 (s, 3H); and 3.83 (m, 1H).

EXAMPLE 36

3-Oxo-4-aza-4-methyl-16β-allyloxy-5α-androstane (55)

This compound was prepared in a similar fashion as Example 35, but substituting allyl bromide in place of iodomethane to yield the title compound; mass spectrum: m/z 345 (M).

400 MHz $^1$H NMR ($CDCl_3$): δ0.88 (s, 3H); 0.90 (s, 3H); 2.90 (s, 3H); 3.00 (dd, 1H); 3.90 (m, 2H); 3.99, (m, 1H); 5.11–5.27 (m, 2H); and 5.83–5.93 (m, 1H).

EXAMPLE 37

3-Oxo-4-aza-4-methyl-16β-(n-propyloxy)-5α-androstane (56)

A solution of 3-oxo-4-aza-4-methyl-16β-allyloxy-5α-androstane in ethyl acetate (0.85 mL) was hydrogenated at atmospheric pressure in the presence of platinum oxide (4 mg) for 30 min at room temperature. The catalyst was removed by filtration through a Millex-HV 0.45 μm Filter Unit. Purification was achieved by flash silica gel chromatography using 10% acetone/methylene chloride as eluant to yield the title compound; mass spectrum: m/z 348 (M+1).

400 MHz NMR ($CDCl_3$): δ0.88 (s, 3H); 0.89 (s, 3H); 2.90 (s, 3H); 3.00 (dd, 1H); 3.28 (t, 2H); and 3.92 (m, 1H).

EXAMPLE 38

3-Oxo-4-aza-4-methyl-16β-(acetamido)-5α-androstane (57) Step 1:
3-Oxo-4-aza-4-methyl-16β-(amino)-5α-androstane (C)

A solution of 4-aza-4-methyl-5α-androstan-3-one-16-oxime (150 mg, 0.471 mmol) in ethanol (15 mL)-acetic acid (7 mL) was hydrogenated at atmospheric pressure in the presence of platinum oxide (50 mg) overnight at room temperature. The catalyst was removed by filtration through a Millex-HV 0.45 μm Filter Unit, and the filtrate was evaporated. The residue was dissolved in methylene chloride (50 mL), and the solution was washed with saturated sodium hydrogencarbonate solution, saturated brine solution, dried ($Na_2SO_4$), and evaporated to afford the desired amine.

Step 2: 3-Oxo-4-aza-4-methyl-16β-(acetamido)-5α-androstane (57)

The amine from Step 1 (56 mg, 0.184 mmol) was dissolved in methylene chloride (1.0 mL) and treated with pyridine (0.6 mL), 4-dimethylaminopyridine (5 mg), and acetic anhydride (0.3 mL) for 2 h at room temperature. The mixture was diluted with methylene chloride (50 mL), and the solution was washed with water, 1N hydrochloric acid, saturated sodium hydrogencarbonate solution, saturated brine solution, dried ($Na_2SO_4$), and evaporated. The product was purified by flash silica gel chromatography using 2% methanol/methylene chloride as eluant to yield the title compound; mass spectrum: m/z 346 (M).

400 MHz $^1$H NMR ($CDCl_3$): δ0.82 (s, 3H); 0.87 (s, 3H); 1.93 (s, 3H); 2.90 (s, 3H); 3.00 (dd, 1H); 4.28 (m, 1H); and 5.54 (d, 1H).

EXAMPLE 39

3-Oxo-4-aza-4-methyl-16β-(benzamido)-5α-androstane (58)

This compound was prepared in a similar fashion as Example 38, but substituting benzoyl chloride in place of acetic anhydride to yield the title compound; mass spectrum: m/z 408 (M).

400 MHz $^1$H NMR ($CDCl_3$): δ0.89 (s, 3H); 0.90 (s, 3H); 2.90 (s, 3H); 3.01 (dd, 1H); 4.48 (m, 1H); and 6.12 (d, 1H).

EXAMPLE 40

3-Oxo-4-aza-4-methyl-16β-(benzylaminocarbonyloxy)-5α-androstane (59)

To a solution of 3-oxo-4-aza-4-methyl-16β-hydroxy-5α-androstane (40 mg, 0.131 mmol) in methylene chloride (2 mL) were added triethylamine (67 μL, 0.481 mmol), 4-dimethylaminopyridine (2 mg), and benzyl isocyanate (50 μL, 0.405 mmol). The reaction mixture was stirred for 48 h at room temperature, evaporated, and then subjected to flash silica gel chromatography using 15% acetone/methylene chloride as eluant to yield the title compound; FAB mass spectrum: m/z 439 (M+1).

400 MHz $^1$H NMR (CDCl$_3$): δ0.87 (s, 6H); 2.90 (s, 3H); 3.00 (dd, 1H); 4.33 (m, 2H); 4.90 (m, 1H) and 5.11 (m, 1H).

EXAMPLE 41

3-Oxo-4-aza-4-methyl-16α-hydroxy-5α-androstane (60)

Step 1: 3-Oxo-4-aza-4-methyl-16α-(4-nitrobenzoyloxy)-5α-androstane (D)

To a solution of 3-oxo-4-aza-4-methyl-16β-hydroxy-5α-androstane (34 mg, 0.0.111 mmol) in dry benzene (1.5 mL) were added triphenylphosphine (35 mg, 0.134 mmol), 4-nitrobenzoic acid (22 mg, 0.134 mmol), and diethyl azodicarboxylate (21 μL, 0.134 mmol). The reaction mixture was heated for one hour at 80° (oil bath temperature) under a nitrogen atmosphere. After removal of the benzene by evaporation under diminished pressure, the crude product mixture was subjected to flash silica gel chromatography using 2% methanol/methylene chloride as eluant to give desired product contaminated with some triphenylphosphine (97 mg) which was saponified as described in Step 2.

Step 2: 3-Oxo-4-aza-4-methyl-16α-hydroxy-5α-androstane (60).

The crude product from Step 1 (97 mg) was suspended in ethanol (0.5 mL) and treated with 0.4N sodium hydroxide (0.36 mL, 0.144 mmol). After stirring 90 min at room temperature, the reaction mixture was neutralized with several drops of glacial acetic acid, extracted with ethyl acetate (2×20 mL), washed with water (20 mL), saturated brine solution, dried (sodium sulfate), and evaporated. The product was obtained pure by flash silica gel chromatography using 20% acetone/methylene chloride as eluant; mass spectrum: m/z 305M.

400 MHz $^1$H NMR (CDCl$_3$): δ0.70 (s, 3H); 0.85 (s, 3H); 2.90 (s, 3H); 3.02 (dd, 1H); and 4.47 (m, 1H).

EXAMPLE 42

3-Oxo-4-aza-4-methyl-16α-methoxy- 5α-androstane (61)

To a solution of 3-oxo-4-aza-4-methyl-16α-hydroxy-5α-androstane (20 mg, 0.065 mmol) in dimethyl sulfoxide (0.6 mL) was added powdered potassium hydroxide (18 mg, 0.325 mmol). After stirring for 15 min at room temperature under an nitrogen atmosphere, iodomethane (20 μl, 0.325 mmol) was added and stirring was continued overnight at room temperature. The mixture was diluted with diethyl ether (25 mL), which was washed with water (2×10 mL), dried (Na$_2$SO$_4$), and evaporated. The desired product was purified by flash silica gel chromatography using 10% acetone/methylene chloride as eluant to yield the title compound; mass spectrum: m/z 319 (M).

400 MHz $^1$H NMR (CDCl$_3$): δ0.70 (s, 3H); 0.87 (s, 3H); 2.90 (s, 3H); 3.01 (dd, 1H); 3.22 (s, 3H); and 3.92 (m, 1H).

EXAMPLE 43

4-Aza-4,7β-dimethyl-5α-androstan-3,16-dione (62)

Step 1: 4-aza-4,7β-dimethyl-5α-androstan-3,17-dione-16-oxime

To 2-methyl-2-propanol (28 mL) in a round-bottom flask under a stream of nitrogen gas was added potassium tert-butoxide (1.35 g, 12.1 mmol). After complete solution was achieved, 4-aza-4,7β-dimethyl-5α-androstan-3,17-dione (1.92 g, 6.0 mmol) was added and stirring was continued for 1 hour affording a gold-colored solution. To the reaction mixture was added dropwise with stirring isoamyl nitrite (1.63 mL, 12.1 mmol), and stirring was continued overnight at room temperature affording a deep-orange solution. The mixture was then diluted with an equal volume of water, acidified to pH~2 with 2N hydrochloric acid, and extracted with diethyl ether (3×50 mL). The combined ether extracts were washed with saturated brine solution, dried (sodium sulfate), and evaporated. The crude product was subjected to flash silica gel chromatography using 5% methanol/methylene chloride as eluant to yield the title compound.

Step 2: 4-aza-4,7β-dimethyl-5α-androstan-3-one-16-oxime

To a mixture of 4-aza-4,7β-dimethyl-5α-androstan-3,17-dione-16-oxime (2.7 g, 7.79 mmol) in ethylene glycol (30 mL) were added 98% hydrazine (0.27 mL, 8.57 mmol) and powdered potassium hydroxide (2.62 g, 46.8 mmol). The mixture was heated for 3 h at 140°, cooled, diluted with water (100 mL), neutralized with concentrated hydrochloric acid to give a tan precipitate that was filtered and dried (1.7 g). Flash silica gel chromatography of this material using initially 2% methanol/methylene chloride and subsequently 5% methanol/methylene chloride as eluant gave pure product.

Step 3: 4-aza-4,7β-dimethyl-5α-androstan-3,16-dione (62)

A mixture of 4-aza-4,7β-dimethyl-5α-androstan-3-one-16-oxime (0.55 g, 1.65 mmol) in 60% acetic acid (20 mL) was heated at reflux temperature for 48 hours. The cooled mixture was diluted with water (25 mL) and extracted with methylene chloride (3×50 mL). The combined extracts were washed with saturated sodium hydrogen-carbonate solution, dried (sodium sulfate), and evaporated. Flash silica gel chromatography using 2% methanol/methylene chloride afforded pure product; mass spectrum: m/z 317 (M).

400 MHz $^1$H NMR (CDCl$_3$): δ0.88 (s, 3H); 0.89 (s, 3H); 1.00 (d, 3H); 2.90 (s, 3H); and 3.07 (dd, 1H).

EXAMPLE 44

3-Oxo-4-aza-4,7β-dimethyl-16β-hydroxy-5α-androstane (63)

A solution of 4-aza-4,7β-dimethyl-5α-androstan-3,16-dione (390 mg, 1.23 mmol) in methanol (8 mL) was cooled in an ice bath and treated with sodium borohydride (140 mg, 3.68 mmol) for 30 min. The reaction mixture was diluted with water and extracted with methylene chloride (3×50 mL). The combined organic extracts were washed with saturated brine solution, dried (Na$_2$SO$_4$), and evaporated. The desired product was purified by flash silica gel chromatography using initially 10% acetone/methylene chloride and subsequently 20% acetone/methylene chloride as eluant to yield the title compound; mass spectrum: m/z 391 (M).

400 MHz $^1$H NMR (CDCl$_3$): δ0.83 (s, 3H); 0.96 (s, 3H); 1.03 (d, 3H); 2.90 (s, 3H); 3.00 (dd, 1H); and 4.36 (m, 1H).

EXAMPLE 45

3-Oxo-4-aza-4,7β-dimethyl-16β-methoxy-5α-androstane (64)

To a solution of 3-oxo-4-aza-4,7β-dimethyl-16β-hydroxy-5α-androstane (20 mg, 0.0.063 mmol) in dimethyl sulfoxide (0.5 mL) was added powdered potassium hydroxide (18 mg, 0.313 mmol). After stirring for 15 min at room temperature under an nitrogen atmosphere, iodomethane (20 μl, 0.313 mmol) was added and stirring was continued overnight at room temperature. The mixture was diluted with diethyl ether (25 mL), which was washed with water, saturated brine solution, dried (Na$_2$SO$_4$), and evaporated. The desired product was purified by flash silica gel chromatography using 1.5% methanol/methylene chloride as eluant to yield the title compound; mass spectrum: m/z 334 (M+1).

400 MHz $^1$H NMR (CDCl$_3$): δ0.83 (s, 3H); 0.89 (s, 3H); 1.03 (d, 3H); 2.90 (s, 3H); 3.00 (dd, 1H); 3.24 (s, 3H); and 3.80 (m, 1H).

EXAMPLE 46

3-Oxo-4-aza-4,7β-dimethyl-16β-ethyloxy-5α-androstane (65)

This compound was prepared in a similar fashion as Example 45, but substituting iodoethane in place of iodomethane and potassium hydride in N,N-dimethylformamide in place of potassium hydroxide in dimethyl sulfoxide; mass spectrum: m/z 347 (M).

400 MHz $^1$H NMR (CDCl$_3$): δ0.83 (s, 3H); 0.90 (s, 3H); 1.03 (d, 3H); 1.18 (t, 3H); 2.90 (s, 3H); 3.00 (dd, 1H); 3.39 (m, 2H); and 4.40 (m, 1H).

EXAMPLE 47

3-Oxo-4-aza-4,7β-dimethyl-16β-allyloxy-5α-androstane (66)

This compound was prepared in a similar fashion as Example 45, but substituting allyl bromide in place of iodomethane; mass spectrum: m/z 359 (M).

400 MHz $^1$H NMR (CDCl$_3$): δ0.83 (s, 3H); 0.91 (s, 3H); 1.04 (d, 3H); 2.90 (s, 3H); 3.00 (dd, 1H); 3.90 (m, 2H); 3.96 (m, 1H); 5.11–5.29 (m, 2H); and 5.85–5.93 (m, 1H).

EXAMPLE 48

3-Oxo-4-aza-4,7β-dimethyl-16β-benzyloxy-5α-androstane (67)

This compound was prepared in a similar fashion as Example 46, but substituting benzyl bromide in place of iodoethane; mass spectrum: m/z 409 (M).

400 MHz $^1$H NMR (CDCl$_3$): δ0.85 (s, 3H); 0.95 (s, 3H); 1.04 (d, 3H); 2.90 (s, 3H); 3.00 (dd, 1H); 4.01 (m, 1H); 4.43 (q, 2H); and 7.31 (m, 5H).

EXAMPLE 49

3-Oxo-4-aza-4,7β-dimethyl-16β-(3,3-dimethylallyloxy)-5α-androstane (68)

This compound was prepared in a similar fashion as Example 45 but substituting 3,3-dimethylallyl bromide in place of iodomethane;

400 MHz $^1$H NMR (CDCl$_3$): δ0.82 (s, 3H); 0.90 (s, 3H); 1.02 (d, 3H); 1.67 (s, 3H); 1.71 (s, 3H); 2.90 (s, 3H); 3.00 (dd, 1H); 3.93 (m, 1H); and 5.31 (m, 1H).

EXAMPLE 50

3-Oxo-4-aza-4,7β-dimethyl-16β-(n-propyloxy)-5α-androstane (69)

A solution of 3-oxo-4-aza-4,7β-dimethyl-16β-allyloxy-5α-androstane (13.0 mg, 0.036 mmol) in ethyl acetate (0.5 mL) was hydrogenated at atmospheric pressure in the presence of platinum oxide (4 mg) for 30 min at room temperature. The catalyst was removed by filtration through a Millex-HV 0.45 gm Filter Unit. Purification was achieved by flash silica gel chromatography using 1% methanol/methylene chloride as eluant to yield the title compound; mass spectrum: m/z 361 (M).

400 MHz $^1$H NMR (CDCl$_3$): δ0.82 (s, 3H); 0.89 (s, 3H); 0.89 (t, 3H); 1.05 (d, 3H); 2.90 (s, 3H); 3.00 (dd, 1H); 3.29 (t, 2H); and 3.89 (m, 1H).

EXAMPLE 51

3-Oxo-4-aza-4,7β-dimethyl-16β-(3-methyl-1-butyloxy)-5α-androstane (70)

A solution of 3-oxo-4-aza-4,7β-dimethyl-16β-(3,3-dimethylallyloxy)- 5α-androstane (12 mg) in ethyl acetate (0.5 mL) was hydrogenated at atmospheric pressure in the presence of 10% palladium-on-charcoal (3 mg) for 30 min at room temperature. The catalyst was removed by filtration through a Millex-HV 0.45 μm Filter Unit. Purification was achieved by flash silica gel chromatography using 2% methanol/methylene chloride as eluant to yield the title compound; mass spectrum: m/z 389M.

400 MHz $^1$H NMR (CDCl$_3$): δ0.82 (s, 3H); 0.88 (s, 3H); 1.03 (d, 3H); 2.90 (s, 3H); 3.00 (dd, 1H); 3.33 (m, 2H); and 3.88 (m, 1H).

EXAMPLE 52

3-Oxo-4-aza-4,7β-dimethyl-16β-(t-butoxy)-5α-androstane (71)

To a solution of 3-oxo-4-aza-4,7β-dimethyl-16β-hydroxy-5α-androstane (20 mg, 0.063 mmol) in methylene chloride (0.5 mL) cooled in an ice-bath were added t-butyl trichloroacetimidate (23 μL, 0.126 mmol) and trifluoromethanesulfonic acid (0.56 μL, 0.0063 mmol). The reaction mixture was allowed to reach room temperature, and after one hour additional amounts of t-butyl trichloroacetimidate (23 μL) and trifluoromethanesulfonic acid (0.56 μL) were added. After one hour, a third addition of each reagent was made, and the reaction mixture was stirred for 5 h at room temperature. The mixture was diluted with diethyl ether (50 mL), washed with 1N aqueous sodium hydroxide (10 mL), 1N hydrochloric acid (10 mL), saturated sodium hydrogencarbonate solution, dried (sodium sulfate), and evaporated. The crude product was purified by flash silica gel chromatography using 10% acetone/methylene chloride as eluant to yield the title compound; mass spectrum: m/z 375 (M).

400 MHz $^1$H NMR (CDCl$_3$): δ0.82 (s, 3H); 0.90 (s, 3H); 1.03 (d, 3H); 1.11 (s, 9H); 2.90 (s, 3H); 3.00 (dd, 1H); and 4.00 (m, 1H).

EXAMPLE 53

3-Oxo-4-aza-4,7β-dimethyl-16β-(4-cyanophenoxy)-5α-androstane (72)

To a solution of 3-oxo-4-aza-4,7β-dimethyl-16β-hydroxy-5α-androstane (20 mg, 0.063 mmol) in N,N-dimethylformamide (0.5 mL) was added powdered potassium hydride (35 weight%) (15 mg, 0.126 mmol). After stirring for 15 min at room temperature under an nitrogen atmosphere, 4-fluorobenzonitrile (38 mg, 0.315 mmol) was added and stirring was continued for 2 hours at room temperature. The mixture was diluted with methylene chloride (25 mL) and quenched in ice-water. The aqueous layer was extracted with methylene chloride (3×25 mL) and the combined organic layers were washed with saturated brine solution, dried (sodium sulfate) and evaporated. The desired product was purified by flash silica gel chromatography using initially 1.5% methanol/methylene chloride and subsequently 2% methanol/methylene chloride as eluant to yield the title compound; mass spectrum: m/z 420 (M).

400 MHz $^1$H NMR (CDCl$_3$): δ0.86 (s, 3H); 0.92 (s, 3H); 1.04 (d, 3H); 2.90 (s, 3H); 3.02 (dd, 1H); 4.76 (m, 1H); 6.87 (m, 2H); and 7.53 (m, 2H).

EXAMPLE 54

3-Oxo-4-aza-4,7β-dimethyl-16β-(4-trifluoromethylphenoxy)-5α-androstane (73)

This compound was prepared in a similar fashion as Example 53, but substituting 4-fluorobenzotrifluoride in place of 4-fluorobenzonitrile; mass spectrum: m/z 463 (M).

400 MHz $^1$H NMR (CDCl$_3$): δ0.85 (s, 3H); 0.93 (s, 3H); 1.04 (d, 3H); 2.90 (s, 3H); 3.02 (dd, 1H); 4.76 (m, 1H); 6.88 (d, 2H); and 7.50 (d, 2H).

EXAMPLE 55

3-Oxo-4-aza-4,7β-dimethyl-16β-(4-chlorophenoxy)-5α-androstane (74)

This compound was prepared in a similar fashion as Example 53, but substituting 1-chloro-4-fluorobenzene in place of 4-fluorobenzonitrile; mass spectrum: m/z 430 (M+1).

400 MHz $^1$H NMR (CDCl$_3$): δ0.85 (s, 3H); 0.93 (s, 3H); 1.03 (d, 3H); 2.90 (s, 3H); 3.02 (dd, 1H); 5.28 (m, 1H); 6.74 (d, 2H); and 7.1.9 (d, 2H).

EXAMPLE 56

3-Oxo-4-aza-4,7β-dimethyl-16β-(4-fluorophenoxy)-5α-androstane (75)

This compound was prepared in a similar fashion as Example 53, but substituting 1,4-difluorobenzene in place of 4-fluorobenzonitrile; mass spectrum: m/z 414 (M+1).

400 MHz $^1$H NMR (CDCl$_3$): δ0.85 (s, 3H); 0.94 (s, 3H); 1.04 (d, 3H); 2.91 (s, 3H); 3.02 (dd, 1H); 4.65 (m, 1H); 6.75 (m, 2H); and 6.92 (m, 2H).

EXAMPLE 57

3-Oxo-4-aza-4,7β-dimethyl-16α-hydroxy-5α-androstane

Step 1: 3-Oxo-4-aza-4,7β-dimethyl-16α-(4-nitrobenzoyloxy)-5α-androstane (F)

To a solution of 3-oxo-4-aza-4,7β-dimethyl-16β-hydroxy-5α-androstane (178 mg, 0.560 mmol) in dry benzene (10 mL) were added triphenylphosphine (294 mg, 1.12 mmol), 4-nitrobenzoic acid (187 mg, 1.12 mmol), and diethyl azodicarboxylate (176 μL, 1.12 mmol). The reaction mixture was heated for one hour at 80° (oil bath temperature) under a nitrogen atmosphere. After removal of the benzene by evaporation under diminished pressure, the crude product mixture was subjected to flash silica gel chromatography using 2% methanol/methylene chloride as eluant to give desired product contaminated with some triphenylphosphine (404 mg) which was saponified as described in Step 2.

400 MHz $^1$H NMR (CDCl$_3$): δ0.80 (s, 3H); 0.88 (s, 3H); 1.03 (d, 3H); 2.90 (s, 3H); 3.05 (dd, 1H); and 5.48 (m, 1H).

Step 2: 3-Oxo-4-aza-4,7β-dimethyl-16α-hydroxy-5α-androstane (76)

The crude product from Step 1 (404 mg) was suspended in ethanol (5 mL) and treated with 0.4N sodium hydroxide (1.82 mL, 0.728 mmol). After stirring 90 min at room temperature, the reaction mixture was neutralized with several drops of glacial acetic acid, extracted with ethyl acetate (100 mL), washed with water (2×25 mL), saturated brine solution, dried (sodium sulfate), and evaporated. The product was obtained pure by flash silica gel chromatography using 20% acetone/methylene chloride as eluant; mass spectrum: m/z 319 (M).

400 MHz $^1$H NMR (CDCl$_3$): δ0.71 (s, 3H); 0.82 (s, 3H); 1.02 (d, 3H); 2.90 (s, 3H); 3.03 (dd, 1H); and 4.42 (m, 1H).

EXAMPLE 58

3-Oxo-4-aza-4,7β-dimethyl-16α-(n-propyloxy)-5α-androstane (77)

To a solution of 3-oxo-4-aza-4,7β-dimethyl-16α-hydroxy-5α-androstane (20 mg, 0.063 mmol) in N,N-dimethylformamide (0.65mL) was added potassium hydride (35 weight%) (15 mg, 0.126 mmol). After stirring for 15 min at room temperature under a nitrogen atmosphere, allyl bromide (27 μl, 0.315 mmol) was added and stirring was continued for 2 h. Additional amounts of potassium hydride (15 mg) and allyl bromide (27 μL) were added, and stirring was continued overnight. The mixture was diluted with diethyl ether (50 mL) and water (10 mL). The organic layer was washed with 1N hydrochloric acid (10 mL), water (10 mL), saturated brine solution, dried (Na$_2$SO$_4$), and evaporated. The desired product was purified by flash silica gel chromatography using 2% methanol/methylene chloride as eluant. This material was hydrogenated in ethyl acetate (0.5 mL) in the presence of 10% palladium-on-charcoal for 2 hours. The catalyst was removed by filtration through a Millex-HV 0.45 μm Filter Unit. Purification was achieved by flash silica gel chromatography using 10% isopropanol/hexane as eluant to yield the title compound; mass spectrum: m/z 361 (M).

400 MHz $^1$H NMR (CDCl$_3$): δ0.76 (s, 3H); 0.82 (s, 3H); 0.90 (t, 3H); 1.02 (d, 3H); 2.90 (s, 3H); 3.02 (dd, 1H); 3.29 (t, 2H); and 3.98 (m, 1H).

EXAMPLE 59

3-Oxo-4-aza-4,16α-dimethyl-16β-hydroxy-5α-androstane (78)

To a solution of 4-aza-4-methyl-5α-androstan-3,16-dione (50 mg, 0.165 mmol) cooled to -40° was added dropwise with stirring methylmagnesium bromide (3.0M solution in diethyl ether) (275 μL, 0.825 mmol). The reaction mixture was allowed to reach room temperature and stirred for 2 h under a nitrogen atmosphere. The reaction was quenched with saturated ammonium chloride solution (25 mL) and extracted with methylene chloride (2×50 mL). The combined organic extracts were washed with saturated brine solution, dried (sodium sulfate) and evaporated. The desired product was obtained pure by flash silica gel chromatography using 2% methanol/methylene chloride as eluant; mass spectrum: m/z 319 (M).

400 MHz $^1$H NMR (CDCl$_3$): δ0.88 (s, 3H); 0.98 (s, 3H); 1.31 (s, 3H); 2.90 (s, 3H); and 3.00 (dd, 1H).

EXAMPLE 60

3-Oxo-4-aza-4,7β,16α-trimethyl-16β-hydroxy-5α-androstane (79)

This compound was prepared in a similar fashion as Example 59, but substituting 4-aza-4,7β-dimethyl-5α-androstan-3,16-dione in place of 4-aza-4-methyl-5α-androstan-3,16-dione as starting material; mass spectrum: m/z 333 (M).

400 MHz $^1$H NMR (CDCl$_3$): δ0.82 (s, 3H); 0.98 (s, 3H); 1.01 (d, 3H); 1.30 (s, 3H); 2.90 (s, 3H); and 3.00 (dd, 1H).

EXAMPLE 61

3-Oxo-4-aza-4,16α-dimethyl-16β-methoxy-5α-androstane (80)

To a solution of 3-oxo-4-aza-4,16α-dimethyl-16β-hydroxy-5α-androstane (31 mg, 0.097 mmol) in N,N-dimethylformamide (0.5 mL) was added potassium hydride (35 weight%) (23 mg, 0.194 mmol). After stirring for 15 min at room temperature, iodomethane (32 μL, 0.485 mmol) was added, and stirring was continued overnight at room temperature. The reaction mixture was diluted with diethyl ether, washed with 2N hydrochloric acid (10 mL), water (10 mL), saturated brine solution, dried (sodium sulfate), and evaporated. The desired product was obtained pure by flash silica gel chromatography using 2% methanol/methylene chloride as eluant; mass spectrum: m/z 333 (M).

400 MHz $^1$H NMR (CDCl$_3$): δ0.88 (s, 3H); 0.90 (s, 3H); 1.22 (s, 3H); 2.90 (s, 3H); 3.00 (dd, 1H); and 3.17 (s, 3H).

EXAMPLE 62

3-Oxo-4-aza-4,7β,16α-trimethyl-16β-methoxy-5α-androstane (81)

This compound was prepared in a similar fashion as Example 61, but substituting 3-oxo-4-aza-4,7β-trimethyl-16β-hydroxy-5α-androstane in place of 3-oxo-4-aza-4,16α-dimethyl-16β-hydroxy-5α-androstane as starting material; mass spectrum: m/z 347 (M).

400 MHz $^1$H NMR (CDCl$_3$): δ0.82 (s, 3H); 0.90 (s, 3H); 1.02 (d, 3H); 1.22 (s, 3H); 2.90 (s, 3H); 3.00 (dd, 1H); and 3.18 (s, 3H).

EXAMPLE 63

3-Oxo-4-aza-4,7β-dimethyl-16β-methanethio-5α-androstane (82)

Step 1: 3-Oxo-4-aza-4,7β-dimethyl-16β-(acetylthio)-5α-androstane (G)

A 25-mL round-bottom flask was charged with dry tetrahydrofuran (4 mL) and triphenylphosphine (177 mg, 0.676 mmol) under a nitrogen atmosphere. The flask was cooled in an ice-bath and diisopropyl azodicarboxylate (133 μL, 0.676 mmol) was added, and the mixture was stirred for 30 min at 0°. To the reaction mixture was added a solution of 3-oxo-4-aza-4,7β-dimethyl-16α-hydroxy-5α-androstane (108 mg, 0.338 mmol) and thiolacetic acid (49 μL, 0.676 mmol) in tetrahydrofuran (2.0 mL). The reaction mixture was stirred for 1 h at 0° and then an additional hour at room temperature. The mixture was evaporated and subjected to flash chromatography on silica gel using 10% acetone/methylene chloride as eluant to give the desired product contaminated with some triphenylphosphine. The mixture was used without further purification in Step 2.

400 MHz $^1$H NMR (CDCl$_3$): δ0.80 (s, 3H); 0.82 (s, 3H); 1.00 (d, 3H); 2.28 (s, 3H); 2.90 (s, 3H); 3.00 (dd, 1H); and 3.80 (m, 1H).

Step 2: 3-Oxo-4-aza-4,7β-dimethyl-16β-(mercapto)-5α-androstane (H)

To a solution of product mixture from Step 1 (208 mg) in ethanol (4.0 mL) was added 0.4N sodium hydroxide (1.8 mL, 0.716 mmol) under a nitrogen atmosphere. The reaction mixture was stirred at room temperature for 1 h, neutralized with several drops of acetic acid, diluted with ethyl acetate (100 mL), washed with water (2×10 mL), saturated brine solution, dried (sodium sulfate), and evaporated. Pure 16-mercaptan was obtained by flash silica gel chromatography using 20% acetone/hexane as eluant.

400 MHz $^1$H NMR (CDCl$_3$): δ0.82 (s, 3H); 0.93 (s, 3H); 1.02 (d, 3H); 2.90 (s, 3H); 3.00 (dd, 1H); and 3.28 (m, 1H).

Step 3: 3-Oxo-4-aza-4,7β-dimethyl-16β-(methanethio)-5α-androstane (82)

To a solution of 3-oxo-4-aza-4,7β-dimethyl-16β-(mercapto)-5α-androstane (18 mg, 0.054 mmol) in dry tetrahydrofuran (0.5 mL) was added sodium hydride (80% dispersion in mineral oil) (3.2 mg, 0.108 mmol) under a nitrogen atmosphere. After stirring 15 min at room temperature, iodomethane (17 μL, 0.270 mmol) was added, and stirring was continued for 3 h at room temperature. The reaction mixture was diluted with methylene chloride (50 mL), washed with water (10 mL), saturated brine solution, dried (sodium sulfate), and evaporated. Flash silica gel chromatography using 10% isopropanol/hexane as eluant afforded pure desired product; mass spectrum: m/z 349 (M).

400 MHz $^1$H NMR (CDCl$_3$): δ0.82 (s, 3H); 0.91 (s, 3H); 1.04 (d, 3H); 2.10 (s, 3H); 2.90 (s, 3H); 3.01 (dd, 1H); and 3.08 (m, 1H).

EXAMPLE 64

3-Oxo-4-aza-4,7β-dimethyl-16β-ethanethio-5α-androstane (83)

This compound was prepared in a similar fashion as Example 53, but substituting iodoethane in place of iodomethane in Step 3; mass spectrum: m/z 363 (M).

400 MHz $^1$H NMR (CDCl$_3$): δ0.82 (s, 3H); 0.91 (s, 3H); 1.03 (d, 3H); 1.24 (t, 3H); 2.57 (q, 2H); 2.90 (s, 3H); 3.00 (dd, 1H); and 3.18 (m, 1H).

EXAMPLE 65

3-Oxo-4-aza-4,7β-dimethyl-16β-(1-propanethio)-5α-androstane (84)

This compound was prepared in a similar fashion as Example 53, but substituting 1-iodopropane in place of iodomethane in Step 3; mass spectrum: m/z 377 (M).

400 MHz $^1$H NMR (CDCl$_3$): δ0.82 (s, 3H); 0.90 (s, 3H); 0.98 (t, 3H); 1.03 (d, 3H); 2.51 (t, 2H); 2.90 (s, 3H); 3.01 (dd, 1H); and 3.13 (m, 1H).

EXAMPLE 66

3-Oxo-4-aza-4,7β-dimethyl-16β-ethanesulfonyl-5α-androstane (85)

To a solution of 3-oxo-4-aza-4,7β-dimethyl-16β-ethanethio-5α-androstane (17 mg, 0.047 mmol) in methanol (1.0 mL) was added a solution of OXONE, monopersulfate compound (19 mg) in water (1 mL). After stirring 2 h at room temperature, an additional amount of OXONE (19 mg) in water (0.5 mL) was added, and stirring was continued for 10 min. The reaction mixture was diluted with water (25 mL) and extracted with methylene chloride (3×50 mL). The combined organic extracts were washed with saturated brine solution, dried (sodium sulfate), and evaporated. Flash silica gel chromatography using 2% methanol/methylene chloride as eluant afforded pure desired product; mass spectrum; m/z 395 (M).

400 MHz $^1$H NMR (CDCl$_3$): δ0.85 (s, 3H); 0.92 (s, 3H); 1.03 (d, 3H); 1.39 (t, 3H); 2.91 (s, 3H); 2.99 (q, 2H); 3.00 (dd, 1H); and 3.41 (m, 1H).

EXAMPLE 67

3-Oxo-4-aza-4,7β-dimethyl-16β-fluoro-5α-androstane

To a solution of 3-oxo-4-aza-4,7β-dimethyl-16α-hydroxy-5α-androstane (18 mg, 0.056 mmol) in methylene chloride (0.5 mL) at room temperature diethylaminosulfur trifluoride (19 μL, 0.144 mmol). After stirring one hour at room temperature, the reaction mixture was diluted with methylene chloride (25 mL), washed with water (25 mL), saturated sodium hydrogen carbonate solution (10 mL), saturated brine solution (10 mL), dried (sodium sulfate), and evaporated. The product was purified by flash silica gel chromatography using 10% acetone/methylene chloride as eluant to yield the title compound; mass spectrum: m/z 321 (M).

400 MHz $^1$H NMR spectrum (CDCl$_3$): δ0.87 (s, 3H); 0.92 (s, 3H); 1.04 (d, 3H); 2.90 (s, 3H); 3.01 (dd, 1H); and 5.12 (dim, 1H).

EXAMPLE 68

Preparation of
4-aza-4,7β-dimethyl-5α-androstan-3,17-dione
(Compound E in Scheme, 5 above)

Step 1: Synthesis of 3-Acetoxy-Androstat-5-en-17-ol

To a solution of 100 mg. (0.303 mmol) of 3-acetoxyandrost-5-en-17-one in 3 ml EtOH at −10° C., was added 22.9 mg (0.606 mmol) of sodium borohydride with stirring. After the reaction mixture was stirred for one and ½ hours, the mixture was diluted with 10 ml water, the ethanol solvent removed under vacuum, and the residue extracted with ethyl acetate. The organic layer was washed with aqueous Na$_2$CO$_3$, brine, dried over sodium sulfate and concentrated to leave a residue of crude title compound. Proton NMR confirmed the assigned structure.

Step 2: Synthesis of 3-Acetoxy-Androst-5-en-17-ol, 17-t-butyl-dimethylsilyl ether To a solution of the androstan-17-ol, from the previous synthesis, being 4.5 g (13.55 mmol) in 50 ml. dimethylformamide at 23° C. was added 2.76 g (40–65 mmol) imidazole followed by 3.063 g (20.32 mmol) of t-butyldimethylsilyl chloride. The reaction mixture was stirred and a solid began to precipitate. Twenty additional ml of DMF were added and the mixture further stirred overnight. The mixture was poured into 1 liter water, the solid filtered and washed with water. The solid was dissolved in ethylacetate, the organic layer washed with brine and dried over sodium sulfate, concentrated to yield the silyl protected 17-ol title compound. The proton NMR confirmed the assigned structure.

Step 3: 7-one-17β-ol, 17-t-butyldimethylsilyl ether

To a solution of the TBMS protected 17-ol from the previous synthesis, being 5.6 g (12.55 mmol) in 100 ml acetonitrile at 23° C. was added 90% t-butyl hydrogen peroxide, 3.958 g (43.92 mol), and 138 mg chromium hexacarbonyl. After refluxing the mixture under nitrogen for 24 hours, the reaction mixture was poured into one liter water, solid was filtered, the residue washed with 500 ml water and the residue dissolved in 350 ml methylene chloride. The organic layer was washed with brine, dried over sodium sulfate and concentrated to yield crude material. Thin layer chromatography (3:1 hexane/ethyl acetate on silica gel) showed the presence of starting material. The solid was purified by column chromatography over silica gel by elution with 7% ethyl acetate/hexane to yield the title compound. Proton NMR confirmed the assigned structure.

Step 4: Synthesis of 3,7-dihydroxy-7-methyl-androst-5-en-17β-ol, 17-t-butyldimethylsilyl ether To a solution of the product from the previous synthesis, being 440 mg (0.956 mmol) in dry tetrahydrofuran at 0° C. was added dropwise methyl magnesium chloride over 5–10 minutes. The reaction mixture was then allowed to stir at room temperature for 24 hours, then poured into saturated aqueous ammonium chloride. The THF solvent was removed under vacuum and the aqueous phase extracted with ethyl acetate. The organic layer was washed with brine, dried, concentrated to yield crude product. Proton NMR confirmed the assigned structure of the title compound which was used in the next step without further purification.

Step 5: Synthesis of 7-methyl-androst-4,6-dien-3-one-17β-ol, 17-t-butyldimethylsilyl ether The above Grignard product, 3.5 g (7.142 mmol) was dissolved in 50 ml toluene/50 ml. cyclohexanone and 20 ml of solvent distilled off under vacuum. To this was added 4.54 g aluminum isopropoxide and the reaction mixture refluxed overnight for 15 hours. The mixture was cooled, diluted with ethyl acetate, washed with sodium potassium tartarate, brine, and the organic layer was concentrated under vacuum and the residue steam distilled. The residue was extracted with ethyl acetate, washed with brine, dried and purified by column chromatography on silica gel, eluting with 5% EtOAc/hexane to yield the title compound.

Step 6: Synthesis of 7β-methyl-androst-5-en-3-one-17β-ol, t-butyldimethylsilyl ether To a solution of 370 mg of the product of the previous synthesis, in 5.5 ml ammonia, 1 ml THF, 1 ml. toluene, was added 50 mg. of metallic lithium in small pieces. After stirring the blue solution for 2 hours, a solution of 1,2-dibromethane in 2 ml THF was added. After stirring the solution at −78° C. for 10 minutes, 250 mg of ammonium chloride was added and the mixture stirred for 10 minutes. The excess ammonia was removed by evaporation under a nitrogen steam. The reaction mixture was diluted with brine, extracted with ethyl acetate. The organic layer was washed with brine, dried and concentrated to yield crude material which was used as such in the next synthesis.

Step 7: Synthesis of 7β-methyl-androst-4-en-3-on-17β-ol, t-butyldimethylsilyl ether To a solution of the product of the previous synthesis, being 432 mg in 4 ml THF was added 150 microliters DBU (1,8-diaza-bicyclo[5.4,0]undec-7-ene under nitrogen with stirring. The mixture was refluxed for 1.5 hours, then cooled, diluted with NH$_4$Cl solution. The solvent THF was removed under vacuum and the residue extracted with ethyl acetate. The organic layer was washed with brine, dried and concentrated under reduced pressure to yield crude material. The titled product was purified by chromatography on silica gel using 10% EtOAc/hexane as eluant.

Step 8: Synthesis of 17β-(t-butyldimethylsilyloxy)-7β-methyl-5-oxo-A-nor-3,5-secoandrostan-3-oic acid To a solution of 884 mg of the product of the previous synthesis in 15 ml. t-butyl alcohol at 80° C. was added 248 mg sodium carbonate in 1.5 ml water followed by a dropwise addition over 15–20 minutes of a mixture of 2.273 g sodium periodate with 16.8 mg potassium permanganate in 8 ml. water. The reaction mixture was heated at 80° C. for 2 hours, cooled, filtered, the residue washed with water, and then the extract L- concentrated under vaccum. The extract was acidified with aqueous HCl, extracted with ethyl acetate and the organic layer washed with aqueous NaHSO$_3$, brine, dried and concentrated to yield crude 9. The proton NMR confirmed the assigned structure.

Step 9: Synthesis of 4,7β-dimethyl-4-aza-androst-5-en-3-one-17β-ol, t-butyldimethylsilyl ether To a solution of the product of the previous synthesis, 840 mg in 5 ml ethylene glycol, was added 1.5 g sodium acetate and 737 mg methylamine hydrochloride. After stirring the reaction mixture 4 hours at 180° C., the mixture was cooled, diluted with water, extracted with ethyl acetate, dried and concentrated to afford crude title compound. Proton NMR confirmed the assigned structure.

Step 10: Synthesis of 4,7β-dimethyl-4-aza-androst-5-en-3-one-17β-ol

To a solution of 700 mg of the product of the previous example, in 20 ml of acetonitrile at 0° C., was added 500 microliters. aqueous HF. After stirring the reaction mixture for one hour, the HF was neutralized with aqueous sodium carbonate, diluted with water, acetonitrile removed under vacuum, and the residue extracted with ethyl acetate. The organic layer was dried, concentrated to give crude title compound which was further purified by preparative chromatography on silica gel using 3:1 chloroform/acetone.

Step 11: Synthesis of 4,7β-dimethyl-4-aza-androstan-3-one-17β-ol

To a solution of the product of the previous synthesis, being 350 mg in 10 ml acetic acid was added 100 mg platinum dioxide and the resulting mixture was evacuated and flushed with hydrogen. The reaction was shaken overnight at room temperature under 40 Psig hydrogen pressure. The solution was filtered concentrated. The residue was worked up with ethyl acetate, the organic layer was then concentrated under vacuum, diluted with ethyl acetate, washed with aqueous NaHCO$_3$, brine, dried, concentrated to yield the title compound. Mass Spec: 320 (M+1).

Step 12: Synthesis of 4-aza-4,7β-dimethyl-5α-androstan-3,17-dione

The product of the previous synthesis, 1.013 g (3.176 mmol) was placed with 6 ml methylene chloride into a dry flask. Powdered molecular 4 Å sieves, 1.6 g, and 0.558 g (4.76 mmol) of N-methyl-morpholine-N-oxide (NMO) and then tetrapropyl-ammonium perruthanate (TPAP), 55 mg (0.159 mmol) were added. The reaction was stirred for 2 hours, diluted with 150 ml ethyl acetate and filtered. The filtrate was evaporated to dryness to yield crude product which was recrystallized from EtOAc to yield pure product, mp 135°–138° C. Elemental Analysis Calc'd for $C_{20}H_{31}NO_2$, mw=317.48 Calc'd: C, 75.67; H, 9.84; N, 4.41 Found: C, 75.16; H, 10.22; N, 4.13 Mass Spec. 318 (M+1).

The following Examples (69 to 117) are prepared in a similar fashion as Example 53, but substituting the appropiate 4-fluoro derivatives in place of 4-fluorobenzonitrile.

EXAMPLE 69

3-Oxo-4-aza-4,7β-dimethyl-16β-(4-methylsulfonylphenoxy)-5α-androstane

Mass spectrum: m/z 474 (M+1). 400 MHz $^1$H NMR (CDCl$_3$): δ0.85 (s, 3H); 0.93 (s, 3H); 1.04 (d, 3H); 2.90 (s, 3H); 3.00 (s, 3H); 4.80 (m,1H); 6.92 (d. 2H); 7.81 (d, 2H).

EXAMPLE 70

3-Oxo-4-aza-4,7β-dimethyl-16β-(3-pyridyloxy)-5α-androstane

Mass spectrum: m/z 397 (M+1). 400 MHz $^1$H NMR (CDCl$_3$): δ0.85 (s, 3H); 0.94 (s, 3H); 1.04 (d, 3H); 2.91 (s, 3H); 3.02 (dd, 1H); 4.75 (m, 1H); 7.21 (m, 2H); 8.22 (m, 2H).

EXAMPLE 71

3-Oxo-4-aza-4,7β-dimethyl-16β-(4-phenylphenoxy)-5α-androstane

Mass spectrum: m/z 472 (M+1). 400 MHz $^1$H NMR (CDCl$_3$): δ0.85 (s, 3H); 0.96 (s, 3H); 1.05 (d, 3H); 2.91 (s, 3H); 3.02 (dd, 1H); 4.76 (m, 1H); 6.9 (d, 2H); 7.26 (m, 1H); 7.43 (m, 2H); 7.52 (m, 4H).

EXAMPLE 72

3-Oxo-4-aza-4,7β-dimethyl-16β-(3-chlorophenoxy)-5α-androstane

Mass spectrum: m/z 431 (M+1). 400 MHz $^1$H NMR (CDCl$_3$): δ0.85 (s, 3H); 0.93 (s, 3H); 1.05 (d, 3H); 2.90 (s, 3H); 4.68 (m, 1H); 6.71 (m, 1H); 6.80 (m, 1H); 6.88 (m, 1H); 7.13 (m, 1H).

EXAMPLE 73

3-Oxo-4-aza-4,7β-dimethyl-16β-(4-trifluoromethoxyphenoxy)-5α-androstane

Mass spectrum: m/z 480(M+1). 400 MHz $^1$H NMR (CDCl$_3$): δ0.85 (s, 3H); 0.94 (s, 3H); 1.04 (d, 3H); 2.91 (s, 3H); 3.02 (dd, 1H); 4.69 (m, 1H); 6.78 (m, 2H); 7.09 (m, 2H).

EXAMPLE 74

3-Oxo-4-aza-4,7β-dimethyl-16β-(2-chlorophenoxy)-5α-androstane

Mass spectrum: m/z 431 (M+1). 400 MHz $^1$H NMR (CDCl$_3$): δ0.85 (s, 3H); 0.99 (s, 3H); 1.04 (d, 3H); 2.91 (s, 3H); 3.03 (dd, 1H); 4.80 (m, 1H); 6.81 (m, 2H); 7.24 (m, 1H); 7.32 (m, 2H).

EXAMPLE 75

3-Oxo-4-aza-4,7β-dimethyl-16β-(2-pyrazinyloxy)-5α-androstane

Mass spectrum: m/z 398 (M+1). 400 MHz $^1$H NMR (CDCl$_3$): δ0.85 (s, 3H); 0.95 (s, 3H); 1.04 (d, 3H); 2.90 (s, 3H); 3.02 (dd, 1H); 5.34 (m, 1H); 8.04 (d, 2H); 8.15 (1H).

EXAMPLE 76

3-Oxo-4-aza-4,7β-dimethyl-16β-(2-pyrimidinyloxy)-5α-androstane

Mass spectrum: m/z 398 (M+1). 400 MHz $^1$H NMR (CDCl$_3$): δ0.85 (s, 3H); 0.95 (s, 3H); 1.04 (d, 3H); 2.90 (s, 3H); 3.02 (dd, 1H); 5.35 (m, 1H); 6.89 (m, 1H); 8.15 (d, 2H);

EXAMPLE 77

3-Oxo-4-aza-4,7β-dimethyl-16β-[4-(1-pyrryl)-phenoxy]-5α-androstane

Mass spectrum: m/z 461 (M+1). 400 MHz $^1$H NMR (CDCl$_3$): δ0.85 (s, 3H); 0.95 (s, 3H); 1.05 (d, 3H); 2.91 (s, 3H); 4.73 (m, 1H); 6.30 (m, 2H); 6.84 (m, 2H); 6.96 (m, 2H); 7.25 (m, 2H).

EXAMPLE 78

3-Oxo-4-aza-4,7β-dimethyl-16β-(3-cyanophenoxy)-5α-androstane

Mass spectrum: m/z 420 (M). 400 MHz $^1$H NMR (CDCl$_3$): δ0.85 (s,3H); 0.93 (s, 3H); 1.04 (d, 3H); 2.91 (s, 3H); 3.02 (dd, 1H); 4.71 (m, 1H); 7.05 (m, 2H); 7.22 (m, 1H); 7.32 (m, 1H).

EXAMPLE 79

3-Oxo-4-aza-4,7β-dimethyl-16β-(1-naphthyloxy)-5α-androstane

Mass spectrum: m/z 445 (M). 400 MHz $^1$H NMR (CDCl$_3$): δ0.86 (s, 3H); 1.03 (s, 3H); 1.07 (d, 3H); 2.92 (s, 3H); 3.02 (dd, 1H); 6.70 (d, 1H); 7.32 (m, 2H); 7.44 (m, 2H); 7.78 (m, 1H); 8.24 (1H).

EXAMPLE 80

3-Oxo-4-aza-4,7β-dimethyl-16β-(3-chloro-4-methylphenoxy)-5α-androstane

Mass spectrum: m/z 445(M+1). 400 MHz $^1$H NMR (CDCl$_3$): δ0.84 (s, 3H); 0.92 (s, 3H); 1.04 (d, 2H); 2.26 (s, 3H); 2.92 (s,3H); 4.76 (m, 1H); 6.62 (m, 1H); 6.81 (m, 1H); 7.12 (d, 1H).

EXAMPLE 81

3-Oxo-4-aza-4,7β-dimethyl-16β-[4-(5-oxazolyl)phenoxy]-5α-androstane

Mass spectrum: m/z 463 (M+1). 400 MHz $^1$H NMR (CDCl$_3$): δ0.85 (s, 3H); 0.95 (s, 3H); 1.05 (d, 3H); 2.91 (s, 3H); 4.76 (m, 1H); 6.86 (d, 2H); 7.21 (s, 1H); 7.53 (d, 2H); 7.84 (s, 1H).

EXAMPLE 82

3-oxo-4-aza-4,7β-dimethyl-16β-(4-nitrophenoxy)-5α-androstane (101)

This compound was prepared in a similar fashion as Example 53, but substituting 1-fluoro-4-nitrobenzene in place of 4-fluorobenzonitrile; 400 MHz $^1$H NMR (CDCl$_3$): δ0.85 (s, 3H); 0.94 (s, 3H); 1.05 (d, 3H); 2.92 (s, 3H); 3.03 (dd, 1H); 4.81 (q, 1H); 6.87 (d, 2H); 8.17 (d, 2H).

EXAMPLE 83

3-oxo-4-aza-4,7β-dimethyl-16β-(4-aminophenoxy)-5α-androstane (102)

To a solution of 3-oxo-4-aza-4,7β-dimethyl-16β-(4-amino-phenoxy)- 5α-androstane (163 mg, 0.36 mmol) in ethylacetate (8 mL) and methanol (8 mL) was added 10% Pd on carbon (25 mg, 0.23 mmol). It was then stirred for four hours under a hydrogen atmosphere at room temperature. It was then filtered through celite and evaporated to afford 148 mg of the title compound. No purification was needed. Mass spectrum: m/z 411 (M+1). 400 MHz $^1$H NMR (CDCl$_3$): δ0.84 (s, 3H); 0.94 (s, 3H); 1.37 (d, 3H); 2.90 (s, 3H); 3.03 (dd, 1H); 4.64 (q, 1H); 6.70 (d, 2H); 6.78 (d, 2H).

EXAMPLE 84

3-oxo-4-aza-4,7β-dimethyl-16β-(4-acetylaminophenoxy)-5α-androstane (103)

To a solution of 3-oxo-4-aza-4,7β-dimethyl-16β-(4-amino-phenoxy)- 5α-androstane (48 mq, 0.116 mmol) in methylene chloride (1 mL) and pyridine (0.037 mL, 0.46 mmol) was added acetic anhydride (0.022 mL, 0.23 mmol) and DMAP (5 mg, 0.04 mmol). The reaction was stirred overnight at room temperature under a nitrogen atmosphere. It was then diluted with methylene chloride (50 mL), washed with water (50 mL) and brine (50 mL). The organic phase was then dried over sodium sulfate and evaporated. The crude product was purified by preparative TLC (silica gel, 1000 microns) using 5% methanol/methylene chloride to give 51 mg of the title compound. Mass spectrum: m/z 453 (M+1). 400 MHz $^1$H NMR (CDCl$_3$): δ0.84 (s, 3H); 0.93 (s, 3H); 1.04 (d, 3H); 2.13 (s, 3H); 2.92 (s, 3H); 3.03 (dd, 1H); 4.68 (q, 1H); 6.76 (d, 2H); 7.11 (s, 1H); 7.33 (d, 2H).

EXAMPLE 85

3-oxo-4-aza-4,7β-dimethyl-16β-(4-benzoylaminophenoxy)-5α-androstane (104)

This compound was prepared in a similar fashion as Example 84, but substituting benzoyl chloride in place of acetic anhydride, triethylamine in place of pyridine and DMAP was not used; mass spectrum: m/z 515 (M+1). 400 MHz $^1$H NMR (CDCl$_3$): δ0.84 (s, 3H); 0.94 (s, 3H); 1.05 (d, 3H); 2.92 (s, 3H); 3.04 (dd, 1H); 4.73 (q, 1H); 6.82 (d, 2H);

7.49 (m, 5H); 7.72 (s, 1H); 7.84 (d, 2H).

EXAMPLE 86

3-oxo-4-aza-4,7β-dimethyl-16β-
(4-methylsulfonamidophenoxy)-5α-androstane
(105)

This compound was prepared in a similar fashion as Example 84, but substituting tosyl chloride in place of acetic anhydride; mass spectrum: m/z 565 (M+1). 400 MHz $^1$H NMR (CDCl$_3$): δ0.84 (s, 3H); 0.93 (s, 3H); 1.03 (d, 3H); 2.37 (s, 3H); 2.92 (s, 3H); 3.02 (dd, 1H); 4.63 (q, 1H); 6.34 (s, 1H); 6.67 (d, 2H); 6.91 (d, 2H); 7.19 (d, 2H); 7.56 (d, 2H).

EXAMPLE 87

3-oxo-4-aza-4-(2,4-dimethoxybenzyl)-7β-methyl-
16β-hydroxy-5α-androstane (106)

This compound was prepared in a similar fashion as compound 63 described in the Scheme 5, except that the corresponding benzyl analog of (Compound E in Scheme 5) was made via similar synthesis of Example 68, except 2,4-dimethoxy-benzylamine was used in place of methylamine in Step 9.

EXAMPLE 88

3-oxo-4-aza-4-(2,4-dimethoxybenzyl)-7β-methyl-
16β-(4-chlorophenoxy)- 5α-androstane (107)

This compound was prepared in a similar fashion as Example 55, but substituting 3-oxo-4-aza-4-(2,4-dimethoxy benzyl)-7β-methyl-16β-hydroxy-5α-androstane in place of 3-oxo-4-aza-4,7β-dimethyl-16β-hydroxy-5α-androstane. No purification was done prior to the next reaction.

EXAMPLE 89

3-oxo-4-aza-7β-methyl-16β-(4-chlorphenoxy)-
5α-androstane (108)

To a solution of 3-oxo-4-aza-4-(2,4-dimethoxy benzyl)-7β-methyl-16β-(4-chlorophenoxy)-5α-androstane (130 mg, 0.23 mmol) in methylene chloride (1 mL) was added trifluoroacetic acid (1 mL). The reaction was stirred overnight at room temperature. Then the solvent was evaporated and the residue taken up in methylene chloride. The organic phase was washed with saturated sodium bicarbonate and brine. It was then dried over sodium sulfate and evaporated. The crude compound was purified by preparative TLC (silica gel, 1000 microns) using 20% acetone/methylene chloride to yield the title compound. 400 MHz $^1$H NMR (CDCl$_3$): δ0.86 (s, 3H); 0.93 (s, 3H); 1.01 (d, 3H); 3.07 (dd, 1H); 4.67 (q, 1H); 5.49 (s, 1H); 6.73 (d, 2H); 7.18 (d, 2H).

EXAMPLE 90

3-oxo-4-aza-7β-methyl-16β-phenoxy-5α-androstane
(109)

To a solution of 3-oxo-4-aza-7β-methyl-16β-(4-chlorophenoxy)-5α-androstane in methanol was added 20% Pd on carbon. This solution was shaken under a hydrogen atmosphere at 48 psig for one day. It was then filtered through celite and evaporated. The crude compound was then purified by flash silica gel chromatography using 20% acetone/methylene chloride to elute the title compound. 400 MHz $^1$H NMR (CDCl$_3$): δ0.86 (s, 3H); 0.95 (s, 3H); 1.01 (d, 2H); 3.08 (dd, 1H); 4.71 (q, 1H); 5.48 (s, 1H); 6.81 (d, 2H); 6.89 (t, 1H); 7.24 (t, 2H).

EXAMPLE 91

3-oxo-4-aza-7β-methyl-16β-phenoxy-
5α-androst-1-ene (110)

To a solution of 3-oxo-4-aza-7β-methyl-16β-phenoxy-5α-androstane (145 mg, 0.35 mmol) in toluene (3 mL) was added DDQ (95 mg, 0.42 mmol), BSTFA (360 mg, 1.4 mmol) and triflic acid (4.04 mg, 0.027 mmol). This solution was stirred overnight at room temperature under a nitrogen atmosphere. Then methylacetoacetate (4.06 mg, 0.035 mmol) was added and the solution was stirred. After one hour, the reaction was refluxed overnight. It was then poured into water (75 mL) containing sodium carbonate (160 mg) and sodium bisufite (120 mg). The aqueous phase was then extracted with methylene chloride (40 mL) (3×) and the organic phases were combined. The organic phase was washed with water (50 mL) and brine (50 mL). It was dried over sodium sulfate and evaporated. The crude compound was purified by flash silica gel chromatography using 15% acetone/methylene chloride to elute the title compound. 400 MHz $^1$H NMR (CDCl$_3$): δ0.92 (s, 3H); 0.96 (s, 3H); 1.02 (d, 3H); 3.34 (dd, 1H); 4.72 (q, 1H); 5.31 (s, 1H); 5.80 (d, 1H); 6.80 (d, 1H); 6.82 (d, 2H); 6.89 (t, 1H); 7.24 (t, 2H).

EXAMPLE 92

3-oxo-4-aza-7β-methyl-16β-(4-chlorophenoxy)-
5α-androst-1-ene (111)

This compound was prepared in a similar fashion as Example 91, but substituting 3-oxo-4-aza-7p-methyl-16β-(4-chlorophenoxy)- 5α-androstane in place of 3-oxo-4-aza-7β-methyl-16β-phenoxy-5α-androstane. 400 MHz $^1$H NMR (CDCl$_3$): δ0.92 (s, 3H); 0.95 (s, 3H); 1.02 (d, 2H); 3.34 (dd, 1H); 4.67 (q, 1H); 5.27 (s, 1H); 5.80 (d, 1H); 6.73 (d, 2H); 6.78 (d, 1H); 7.18 (d, 2H).

EXAMPLE 93

3-oxo-4-aza-4,7β-dimethyl-16β-phenoxy-
5α-androstane (112)

To a solution of 3-oxo-4-aza-7β-methyl-16β-phenoxy-5α-androstane (60 mg, 0.16 mmol) in N,N-dimethylformamide (1 mL) was added sodium hydride (8 mg, 0.21 mmol), a 60% dispersion in mineral oil. After stirring for 30 min at room temperature under a nitrogen atmosphere, methyl iodide (40 mg, 0.28 mmol) was added. The reaction was stirred overnight. It was diluted with ethylacetate (50 mL) and washed with 1N hydrochloric acid (50 mL), water (50 mL) and brine (50 mL). The organic phase was dried over sodium sulfate and evaporated. The crude product was purified by flash silica gel chromatography using 10% acetone/methylene chloride to elute the title compound. 400 MHz $^1$H NMR (CDCl$_3$): δ0.85 (s, 3H); 0.95 (s, 3H); 1.05 (d, 3H); 2.91 (s, 3H); 3.02 (dd, 1H); 4.72 (q, 1H); 6.81 (d, 2H); 6.89 (t, 1H); 7.24 (t, 2H).

EXAMPLE 94

3-oxo-4-aza-4,7β-dimethyl-16β-(4-chlorophenoxy)-5α-androst-1-ene (113)

This compound was prepared in a similar fashion as Example 93, but substituting 3-oxo-4-aza-7β-methyl-16β-(4-chlorophenoxy)- 5α-androstan-1-ene in place of 3-oxo-4-aza-7β-methyl-16β-phenoxy-5α-androstane. 400 MHz $^1$H NMR (CDCl$_3$): δ0.87 (s, 3H); 0.95 (s, 3H); 1.07 (d, 2H); 2.93 (s, 1H); 3.34 (dd, 1H); 4.68 (q, 1H); 5.84 (d, 1H); 6.69 (d, 1H); 6.73 (d, 2H); 7.18 (d, 2H).

EXAMPLE 95

3-oxo-4-aza-4-(2,4-dimethoxybenzyl)-7β-methyl-16β-(3-chloro-4-methylphenoxy)-5α-androstane (114)

This compound was prepared in a similar fashion as Example 88, but substituting 2-chloro-4-fluorotoluene in place of 1-chloro-4-fluorobenzene. No purification was done prior to the next reaction.

EXAMPLE 96

3-oxo-4-aza-7β-methyl-16β-(3-chloro-4-methylphenoxy)-5α-androstane (115)

This compound was prepared in a similar fashion as Example 89, but substituting 3-oxo-4-aza-4-(2,4-dimethoxybenzyl)-7β-methyl-16β-(3-chloro-4-methylphenoxy)-5α-androstane in place of 3-oxo-4-aza-4-(2,4-dimethoxy benzyl)-7β-methyl-16β-(4-chlorophenoxy)-5α-androstane. 400 MHz $^1$H NMR (CDCl$_3$): δ0.86 (s, 3H); 0.93 (s, 3H); 1.01 (d, 3H); 2.26 (s, 3H); 3.08 (dd, 1H); 4.66 (q, 1H); 5.59 (s, 1H); 6.62 (m, 1H); 6.81 (d, 1H); 7.06 (d, 1H).

EXAMPLE 97

3-oxo-4-aza-7β-methyl-16β-(4-methylphenoxy)-5α-androstane (116)

This compound was prepared in a similar fashion as Example 90, but substituting 3-oxo-4-aza-7β-methyl-16β-(3-chloro-4-methyl-phenoxy)-5α-androstane in place of 3-oxo-4-aza-7β-methyl-16β-(4-chloro-phenoxy)-5α-androstane. 400 MHz $^1$H NMR (CDCl$_3$): δ0.86 (s, 3H); 0.94 (s, 3H); 1.03 (d, 3H); 2.25 (s, 3H); 4.69 (q, 1H); 6.71 (d, 2H); 7.03 (d, 2H).

EXAMPLE 98

3-oxo-4-aza-7β-methyl-16β-(4-methylphenoxy)-5α-androst-1-ene (117)

This compound was prepared in a similar fashion as Example 91, but substituting 3-oxo-4-aza-7β-methyl-16β-(4-methylphenoxy)-5α-androstane in place of 3-oxo-4-aza-7β-methyl-16β-phenoxy-5α-androstane. 400 MHz $^1$H NMR (CDCl$_3$): δ0.92 (s, 3H); 0.96 (s, 3H); 1.03 (d, 3H); 2.25 (s, 3H); 3.34 (dd, 1H); 4.68 (q, 1H); 5.35 (s, 1H); 5.81 (d, 1H); 6.71 (d, 2H); 6.79 (d, 1H); 7.03 (d, 2H).

EXAMPLE 99

3-oxo-4-aza-7β-methyl-16β-(4-methylphenoxy)-5α-androstane (118)

This compound was prepared in a similar fashion as Example 93, but substituting 3-oxo-4-aza-7β-methyl-16β-(4-methylphenoxy)- 5α-androstane in place of 3-oxo-4-aza-7β-methyl-16β-phenoxy-5α-androstane. 400 MHz $^1$H NMR (CDCl$_3$): δ0.85 (s, 3H); 0.94 (s, 3H); 1.04 (d, 3H); 2.25 (s, 3H); 2.91 (s, 3H); 3.05 (dd, 1H); 4.69 (q, 1H); 6.71 (d, 2H); 7.04 (d, 2H).

EXAMPLE 100

3-Oxo-4-aza-4,7β-dimethyl-16β-fluoro-5α-androstane

This compound was prepared by treatment of intermediate (12) (Scheme 5) with diethylaminosulfur trifluoride in methylene chloride at room temperature followed by chromatography on silica gel; 64% yield; m/z 321 (M); 400 MHz $^1$H NMR spectrum (CDCl$_3$): 0.87 (s, 3H); 0.92 (s, 3H); 1.04 (d, 3H); 2.90 (s, 3H), 5.12 (m, H).

EXAMPLE 101

3-Oxo-4-aza-4,7β-dimethyl-16β-cyano-5α-androstane

This compound is obtained by conversion of intermediate (25) (Scheme 7) to its methansulfonate derivative by treatment with methanesulfonyl chloride or methanesulfonic anhydride in methylene chloride in the presence of an organic base, such as pyridine and triethylamine, and 4-dimethylaminopyridine (DMAP). Displacement of the methanesulfonate group is effected by heating in an appropriate solvent, such as N,N-dimethylformamide or dimethylsulfoxide, in the presence of sodium or potassium cyanide.

EXAMPLE 102

3-Oxo-4-aza-4-methyl-16β-(1-hexyl)-5α-androstane

Step 1: 3-Oxo-4-aza-4-methyl-16β-(1-hexenyl)-5α-androstane

To a 50-mL round-bottom flask under nitrogen was added 1-hexyl-triphenylphosphonium bromide (141 mg, 0.33 mmol) followed by freshly distilled tetrahydrofuran (1 mL). The mixture was cooled to 0° C., and butyllithium (2.5M solution in hexanes, 132 mL, 0.33 mmol) affording a bright orange solution. The solution was stirred at 0° C. for 10 min., and was charged with a solution of 4-aza-4-methyl-5α-androstan-3,16-dione (50 mg, 0.165 mmol) in tetrahydrofuran (0.5 mL). The reaction mixture was allowed to reach room temperature and stirred overnight. The mixture was then partitioned between water (10 mL) and ethyl acetate (20 mL), the organic layer separated, washed with 0.5N hydrochloric acid (2×10 mL), saturated brine solution, dried (Na$_2$SO4), and evaporated. The title compound was purified by flash silica gel chromatography using 1% methanol/methylene chloride as eluant. This material (29.6 mg) was used without further purification in Step 2.

Step 2: 3-Oxo-4-aza-4-methyl-16β-(1-hexyl)-5α-androstane

A solution of the product obtained in Step 1 (22 mg) in ethyl acetate (0.5 mL) was hydrogenated in the presence of platinum oxide (5 mg) under a balloon atmosphere of hydrogen gas for 1 hour at room temperature. The catalyst was removed by filtration through a Millex-HV disposable filter, and the filtrate was evaporated. The title compound was purified by flash silica gel chromatography using 20% acetone/hexane as eluant; yield 5.2 mg. Mass spectrum: m/z 374 (M+1). 400 MHz $^1$H NMR (CDCl$_3$): δ2.42 (dd, 2H), 2.90 (s, 3H), and 3.00 (dd, 1H).

EXAMPLE 103

4-aza-4,7β-dimethyl-16b-(4-chlorobenzylidene)-5α-androstan-3-one (128)

Following Reaction Scheme 14, solution of 4-aza-4,7β-dimethyl-5α-androstan-3,17-dione (32 mg, 0.1 mmol), sodium hydride (5 mg, 1.02 eq), diethyl 4-chlorobenzylphosphonate (27 mg, 1.02 eq) and DMF (0.5mL) were heated to 80° C. for 1 hour. The reaction was cooled, diluted with dichloromethane and washed with water (x2), brine, dried over anhydrous magnesium sulfate, filtered and concentrated. The desired product was purified by silica gel chromatography (hexanes:isopropanol 4:1) 11.5:1 mixture of E/Z isomers: m/z=389 $^1$H NMR(500 MHz, CDCl$_3$):0.75 (s, 3H); 0.82 (s, 3H); 0.90 (d, 3H); 2.96 (s, 3H); 3.08 (dd, 1H); 6.34 (s, 0.4H); 6.41 (s, 0.6H); 7.18–7.38 (m, 5H).

EXAMPLE 104

4-aza-4,7β-dimethyl-16-benzylidene-5α-androstan-3-one (127)

This example was prepared in a similar fashion as 4-aza-4,7β-dimethyl-16-(4-chlorobenzylidene)-5α-androstan-3-one but substituting diethyl benzylphosphonate for diethyl 4-chlorobenzylphosphonate: m/z=390

$^1$H NMR(500 MHz, CDCl$_3$): 0.75 (s, 3H); 0.88 (s, 3H); 1.05 (d, 3H); 2.94 (s, 3H); 3.08 (dd, 1H); 6.28 (s, 0.4H); 6.35 (s, 0.6H); 7.15–7.35(m, 5H).

EXAMPLE 105

4-aza-4,7β-dimethyl-16-(4-methylbenzylidene)-5α-androstan-3-one (129)

This example was prepared in a similar fashion as 4-aza-4,7β-dimethyl-16-(4-chlorobenzylidene)-5α-androstan-3-one but substituting diethyl 4-methylphosphonate for diethyl 4-chlorobenzylphosphonate: m/z=404

$^1$H NMR (500 MHz, CDCl$_3$): 0.78 (s, 3H); 0.85 (s, 3H); 1.1 (d, 3H); 2.32 (s, 3H); 2.94 (s, 3H);3.08 (dd, 1H); 6.30 (s, 0.4H); 6.38 (s, 0.6H); 7.10–7.24 (m, 5H).

EXAMPLE 106

4-aza-4,7β-dimethyl-16-(4-chlorobenzyl)-5α-androstan-3-one (130)

To a solution of 4-aza-4,7β-dimethyl-16-(4-chlorobenzylidene)- 5α-androstan-3-one (33 mg) in ethanol (4 mL) was added 5% Rh/C and the black suspension stirred under ahydrogen balloon. After 2 hours the mixture was filtered to remove catalyst, concentrated and purified on silica gel (hexanes:acetone 3:1) to give the desired product as a 3:1 mixture of isomers: m/z 427

$^1$H NMR (500 MHz, CDCl$_3$): 0.84 (s,3H); 0.86 (s,3H); 1.02 (d, 3H); 2.92 (bs, 2.7H); 2.93 (bs, 1.3H); 2.98 (s, 3H); 3.02 (dd, 1H); 7.10 (d, 2H), 7.25 (d, 2H).

EXAMPLE 107

4-aza-4,7β-dimethyl-16-(4-methylbenzyl)-5α-androstan-3-one (131)

This example was prepared similarly to the procedure used for 4-aza-4,7β-dimethyl-16-(4-chlorobenzyl)-5α-androstan-3-one: m/z=408

$^1$H NMR (500 MHz, CDCl$_3$): 0.86(s, 6H); 1.04 (d, 3H); 2.33 (s, 3H); 2.95 (s, 2H); 2.96 (s, 1H); 3.05 (dd, 1H); 7.06–7.11 (m, 4H).

EXAMPLE 108

4-aza-4,7β-dimethyl-16-(3-pyridylmethyl)-5α-androstan-3-one (132)

This example was prepared similarly to the procedure used for 4-aza-4,7β-dimethyl-16-(4-chlorobenzyl)-5α-androstan-3-one except 3-pyridylmethyl-dimethylphosphonate was used: m/z=395

$^1$H NMR (500 MHz, CDCl$_3$):0.89 (s, 3H); 0.88 (s, 3H); 1.03(d, 3H); 2.93 (bs, 2H); 2.94 (bs, 1H); 2.98 (s, 3H); 3.04 (dd, 1H); 7.10 (d, 2H), 7.25 (d, 2H); 7.58 (s, 1H); 8.55 (s, 2H).

EXAMPLE 109

4-aza-4,7β-dimethyl-16α-methanesulfonyl-5α-androstan-3-one (119)

Following Reaction Scheme 13, to a solution of 4-aza-4, 7β-dimethyl-16α-hydroxy-5α-androstan-3-one (65 mg, 0.2 mmol) in anhydrous dichloromethane was added a catalytic amount of DMAP followed with methanesulfonic anhydride (45 mg, 1.1 eq). After 15 min, the reaction was diluted with dichloromethane, washed with 1M HCl (×3), 1M sodium bicarbonate, water and brine, dried over anhydrous magnesium sulfate filtered and concentrated to yield the desired compound of suffcient purity: m/z=398

$^1$H NMR (500 MHz, CDCl$_3$): 0.78 (s, 3H); 0.85 (s, 3H); 1.02 (d, 3H); 2.95 (s, 3H); 3.1 (dd, 2H); 5.18 (m, 1H);

EXAMPLE 110

4-aza-4,7β-dimethyl-16β-thiophenoxy-5α-androstan-3-one (120)

To a solution of thiophenol (50 μL, 2.5 eq) in anhydrous THF was added sodium hydride (20 mg, 2.6 eq). After stirring 20 min, a THF solution of 4-aza-4,7β-dimethyl-16α-methanesulfonyl-5α-androstan-3-one (65 mg. 0.2 mmol) was added and the mixture stirred 20 hours at ambient temperature. The reaction was quenched with 1M ammonium chloride and diluted with ethyl acetate, washed with water and brine, dried over anhydrous magnesium sulfate filtered and concentrated. The desired compound was purified by silica gel chromatography (hexanes:isopropanol 9:1): m/z=412

$^1$H NMR (500 MHz, CDCl$_3$): 0.86 (s, 3H); 0.96 (s, 3H); 1.06 (d, 3H); 2.94 (s, 3H); 3.06 (dd, 2H); 3.65 (m, 1H); 7.26–7.70 (m, 5H).

EXAMPLE 111

4-aza-4,7β-dimethyl-16β-(4-chlorothiophenoxy)-5α-androstan-3-one (121)

This compound was prepared in a similar fashion as 4-aza- 4,7β-dimethyl-16β-thiophenoxy-5α-androstan-3-one but substituting 4-chlorothiophenol in place of thiophenol: m/z=446

$^1$H NMR (500 MHz, CDCl$_3$): 0.85 (s,3H); 0.96 (s, 3H); 1.04 (d, 3H); 2.94 (s, 3H); 3.02 (dd, 2H); 3.61 (m, 1H); 7.22 (d, 2H); 7.32 (d, 2H).

EXAMPLE 112

4-aza-4,7β-dimethyl-16β-(4-fluorothiophenoxy)-5α-androstan-3-one (122)

This compound was prepared in a similar fashion as 4-aza-4,7β-dimethyl-16β-thiophenoxy-5α-androstan-3-one but substituting 4-fluorothiophenol in place of thiophenol: m/z=431

$^1$H NMR (500 MHz, CDCl$_3$): 0.85 (s, 3H); 0.96 (s, 3H); 1.05 (d, 3H); 2.92 (s, 3H); 3.03 (dd, 2H); 3.51 (m, 1H); 6.99 (d, 2H); 7.35 (d, 2H).

EXAMPLE 113

4-aza-4,7β-dimethyl-16β-(4-methylthiophenoxy)-5α-androstan-3-one (123)

This compound was prepared in a similar fashion as 4-aza-4,7β-dimethyl-16β-thiophenoxy-5α-androstan-3-one but substituting 4-methylthiophenol in place of thiophenol:m/z=426

$^1$H NMR(500 MHz, CDCl$_3$): 0.75 (s, 3H); 0.95 (s, 3H); 1.1 (d, 3H); 2.31 (s, 3H): 2.94 (s, 3H); 3.02 (dd, 2H); 3.59 (m, 1H); 7.09 (d, 2H); 7.22 (d, 2H).

EXAMPLE 114

4-aza-4,7β-dimethyl-16β-(4-methoxythiophenoxy)-5α-androstan-3-one (124)

This compound was prepared in a similar fashion as 4-aza-4,7β-dimethyl-16β-thiophenoxy-5α-androstan-3-one but substituting 4 -methoxythiophenol in place of thiophenol: m/z=443

$^1$H NMR (500 MHz, CDCl$_3$): 0.81 (s,3H); 0.93 (s,3H); 1.18 (d,3H); 2.93 (s,3H); 3.02 (dd,2H); 3.50 (m,1H); 3.81 (s,3H); 7.45 (d,2H); 7.67 (d,2H).

EXAMPLE 115

4-aza-4,7β-dimethyl-16β-phenylsulfinyl-5α-androstan-3-one (125)

To a solution of 4-aza-4,7β-dimethyl-16β-thiophenoxy-5α-androstan-3-one (20 mg, 0.05 mmol) in dicloromethane at 0° C. was added mCPB A (11 mg, 1 eq) and the solution stirred 1 hour. The reaction was diluted with dichloromethane and washed with 1M sodium bicarbonate, water, brine and dried over anhydrous sodium sulfate. The desired compound was purified by silica gel chromatography to yield a 4.6:1 mixture of diastereomers: m/z=428

$^1$H NMR(500 MHz, CDCl$_3$): 0.83 (s, 3H); 0.92 (s, 3H); 1.01 (d, 3H); 2.92 (s, 3H); 3.01 (dd, 2H); 3.19 (m, 0.85H); 3.55 (m, 0.15H); 7.5–7.70 (m, 5H).

EXAMPLE 116

4-aza-4,7β-dimethyl-16β-phenylsulfonyl-5α-androstan-3-one (126)

A solution of 4-aza-4,7β-dimethyl-16β-phenylsulfinyl-5α-androstan-3-one 912 mg, 0.03 mmol) in dichloromethane was treated with mCPBA (9 mg, 1.5 eq) for 3 hours. The reaction was diluted with dichloromethane and washed with 1M sodium bicarbonate, water, brine and dried over anhydrous sodium sulfate. The desired compound was purified by silica gel chromatography (hexanes:isopropanol 7:3): m/z=444

$^1$H NMR (500 MHz, CDCl$_3$): 0.85 (s, 3H); 0.91 (s, 3H); 1.0 (d, 3H); 2.95 (s, 3H); 3.05 (dd, 2H); 3.55 (m, 0.15H); 7.41 (t, 1H); 7.55 (t, 2H); 7.90 (d, 1H), 7.90 (d, 1H).

EXAMPLE 117

3-Oxo-4-aza-4,16β-dimethyl-5α-androstane

This compound is made by converting the readily available 4-aza-4,16β-dimethyl-androstan-3,17-dione to the 17-triflate. Reduction of the 17-triflate through conventional methods yields the titled 16-βmethyl analog.

Mass spectrum: m/z 304 (M+1) 400 MHz NMR (CDCl$_3$): δ0.76 (s, 3H); 0.85 (s, 3H); 1.04 (d, 3H); 2.90 (s, 3H); 3.01 (dd, 1H).

What is claimed is:

1. A method of treating acne comprising the step of administering to a person in need thereof a therapeutically effective amount of a 5α-reductase inhibitor and at least one member selected from the group consisting of an antibacterial agent, a keratolytic agent and an anti-inflammatory agent.

2. The method of claim 1 wherein said 5α-reductase inhibitor is a 5α-reductase 1 inhibitor.

3. The method of claim 2 further comprising a 5α-reductase 2 inhibitor.

4. The method of claim 3 wherein said 5α-reductase 2 inhibitor is finasteride, episteride or turosteride.

5. The method of claim 2 wherein said 5α-reductase 1 inhibitor is selected from the group consisting of (I.):

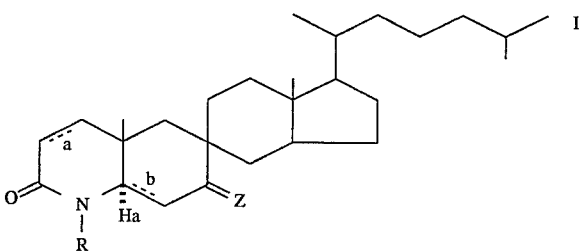

or a pharmaceutically acceptable salt or ester thereof, wherein for Structure I:

R is selected from hydrogen, methyl, ethyl, —OH, —NH$_2$, and —SCH$_3$; the dashed lines "- - -" a and b independently represent a single bond or a double bond providing that when b is a double bond, the 5α hydrogen, Ha, is absent;

═Z is selected from:
  1) oxo,
  2) α-hydrogen and a β-substituent selected from:
    a) C$_1$–C$_4$ alkyl,
    b) C$_2$–C$_4$ alkenyl,
    c) CH$_2$COOH, d) —OH,
e) —COOH,
f) —COO(C$_1$-C$_4$ alkyl),
g) —OC(O)NR$^1$R$^2$ wherein R$^1$ and R$^2$ independently are selected from:
  i) H,
  ii) C$_1$–C$_4$ alkyl,
  iii) phenyl, and
  iv) benzyl, or
  R$^1$ and R$^2$ together with the nitrogen atom to which they are attached represent a 5–6 membered saturated heterocycle, optionally containing one other heteratom selected from —O—, —S— and —N(R')— wherein R' is —H or methyl;
h) C$_1$–C$_4$ alkoxy,
i) C$_3$–C$_6$ cycloalkoxy,
j) —OC(O)—C$_{1-4}$ alkyl,
k) halo,
l) hydroxy-C$_1$–C$_2$ alkyl,
m) halo-C$_1$–C$_2$ alkyl,
n) —CF$_3$, and
o) C$_3$–C$_6$ cycloalkyl;
3) =CHR$^3$; wherein R$^3$ is selected from —H and C$_1$–C$_4$ alkyl; and
4) spirocyclopropane-R$^3$ of structure:

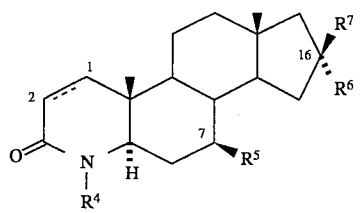

and

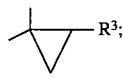

or a pharmaceutically acceptable salt or ester thereof wherein:

the C$_1$–C$_2$ carbon-carbon bond may be a single bond, or a double bond as indicated by the dashed line;

R$^4$ is selected from the group consisting of hydrogen and C$_{1-10}$ alkyl;

R$^5$ is selected from the group consisting of hydrogen and C$_{1-10}$ alkyl; one of R$^6$ and R$^7$ is selected from the group consisting of hydrogen and methyl, and the other is selected from the group consisting of:
(a) amino;
(b) cyano;
(c) fluoro;
(d) methyl;
(e) OH;
(f) —C(O)NR$_b$R$_c$, where R$_b$ and R$_c$ are independently H, C$_{1-6}$ alkyl, aryl, or arylC$_{1-6}$ alkyl; wherein the alkyl moiety can be substituted with 1–3 of: halo; C$_{1-4}$ alkoxy; or trifluoromethyl; and the aryl moiety can be substituted with 1–3 of: halo; C$_{1-4}$alkyl; C$_{1-4}$ alkoxy; or trifluoromethyl;
(g) C$_{1-10}$ alkyl-X—;
(h) C$_{2-10}$ alkenyl-X—;
wherein the C$_{1-10}$ alkyl in (g) and C$_{2-10}$ alkenyl in (h) can be unsubstituted or substituted with one to three of:
  i) halo; hydroxy; cyano; nitro; mono-, di- or trihalomethyl; oxo; hydroxysulfonyl; carboxy;
  ii) hydroxyC$_{1-6}$alkyl; C$_{1-6}$alkyloxy; C$_{1-6}$ alkylthio; C$_{1-6}$alkylsulfonyl; C$_{1-6}$ alkyloxycarbonyl; in which the C$_{1-6}$ alkyl moiety can be further substituted with 1–3 of: halo; C$_{1-4}$ alkoxy; or trifluoromethyl;
  iii) arylthio; aryl; aryloxy; arylsulfonyl; aryloxycarbonyl; in which the aryl moiety can be further substituted with 1–3 of: halo; C$_{1-4}$ alkyl; C$_{1-4}$ alkoxy; or trifluoromethyl;
  iv) —C(O)NR$_b$R$_c$; —N(R$_b$)—C(O)—R$_c$; —NR$_b$R$_c$; where R$_b$ and R$_c$ are defined above;
(i) aryl-X—;
(j) heteroaryl-X—, wherein heteroaryl is a 5, 6 or 7 membered heteroaromatic ring containing at least one member selected from the group consisting of: one ring oxygen atom, one ring sulfur atom, 1–4 ring nitrogen atoms, or combinations thereof; in which the heteroaromatic ring can also be fused with one benzo or heteroaromatic ring; wherein the aryl in (i) and heteroaryl in (j) can be unsubstituted or substituted with one to three of:
  v) halo; hydroxy; cyano; nitro; mono-, di- or trihalomethyl; mono-, di- or trihalomethoxy; C$_{2-6}$ alkenyl; C$_{3-6}$ cycloalkyl; formyl; hydrosulfonyl; carboxy; ureido;
  vi) C$_{1-6}$ alkyl; hydroxy C$_{1-6}$ alkyl; C$_{1-6}$ alkyloxy; C$_{1-6}$ alkyloxy C$_{1-6}$alkyl; C$_{1-6}$ alkylcarbonyl; C$_{1-6}$ alkylsulfonyl; C$_{1-6}$ alkylthio; C$_{1-6}$ alkylsulfinyl; C$_{1-6}$ alkylsulfonamido; C$_{1-6}$ alkylarylsulfonamido; C$_{1-6}$ alkyloxy-carbonyl; C$_{1-6}$ alkyloxycarbonyl C$_{1-6}$alkyl; R$_b$R$_c$N—C(O)—C$_{1-6}$alkyl; C$_{1-6}$ alkanoylamino C$_{1-6}$ alkyl; aroylamino C$_{1-6}$ alkyl; wherein the C$_{1-6}$ alkyl moiety can be substituted with 1–3 of: halo; C$_{1-4}$alkoxy; or trifluoromethyl;
  vii) aryl; aryloxy; arylcarbonyl; arylthio; arylsulfonyl; arylsulfinyl; arylsulfonamido; aryloxycarbonyl; wherein the aryl moiety can be substituted with 1–3 of: halo; C$_{1-4}$alkyl; C$_{1-4}$alkoxy; or trifluoromethyl;
  viii) —C(O)NR$_b$R$_c$; —O—C(O)—NR$_b$R$_c$; —N(R$_b$)—C(O)—R$_c$; —NR$_b$R$_c$; R$_b$—C(O)—N(R$_c$)—; where R$_b$ and R$_c$ are defined in (f) above; and —N(R$_b$)—C(O)—OR$_g$, wherein R$_g$ is C$_{1-6}$alkyl or aryl, in which the alkyl moiety can be substituted with 1–3 of: halo; C$_{1-4}$alkoxy; or trifluoromethyl, and the aryl moiety can be substituted with 1–3 of: halo; C$_{1-4}$alkyl; C$_{1-4}$ alkoxy, or trifluoromethyl; —N(R$_b$)—C(O)NR$_c$R$_d$, wherein R$_d$ is selected from H, C$_{1-6}$ alkyl, and aryl; in which said C$_{1-6}$alkyl and aryl can be substituted as described above in (f) for R$_b$ and R$_c$;
  ix) a heterocyclic group, which is a 5, 6 or 7 membered ring, containing at least one member selected from the group consisting of: one ring oxygen atom, one ring sulfur atom, 1–4 ring nitrogen atoms, or combinations thereof; in which the heterocyclic ring can be aromatic, unsaturated, or saturated, wherein the heterocyclic ring can be fused with a benzo ring, and wherein said heterocyclic ring can be substituted with one to three substituents, as defined above for v), vi), vii) and viii), excluding ix) a heterocyclic group; and
(k) R$^6$ and R$^7$ taken together can be carbonyl oxygen;
(l) R$^6$ and R$^7$ taken together can be =CH—R$_g$, wherein R$_g$ is defined in viii); and wherein:

X is selected from the group consisting of:
—O—; —S(O)$_n$—; —C(O)—; —CH(R$_e$)—; —C(O)—O—*; —C(O)—N(R$_e$)—*; —N(R$_e$)—C(O)—O—*; —O—C(O)—N(R$_e$)—*; —N(R$_e$)C(O)—N(R$_e$)—; —O—CH(R$_e$)—*; —N(R$_e$)—; wherein R$_e$ is H, C$_{1-3}$ alkyl, aryl, aryl-C$_{1-3}$ alkyl, or unsubstituted or substituted heteroaryl, as defined above in (j);

wherein the asterisk (*) denotes the bond which is attached to the 16-position in Structure II; and n is zero, 1 or 2.

6. The method of claim 5 wherein said 5α-reductase inhibitor is of the structural formula:

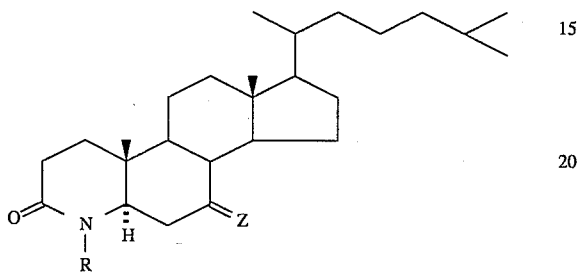

where R is H or CH$_3$.

7. The method of claim 5 wherein said 5α-reductase is of the structural formula:

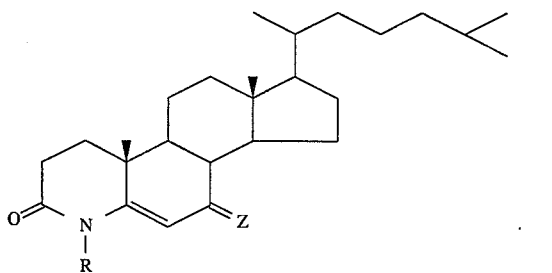

8. The method of claim 5 wherein said 5α-reductase inhibitor is of the structural formula:

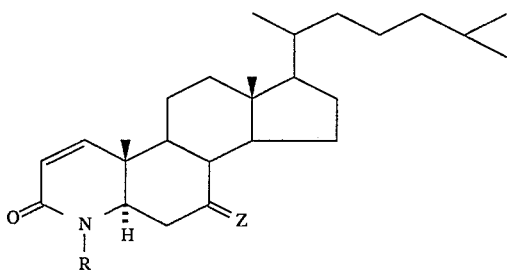

9. The method of claim 5 wherein Z is α-hydrogen and the β-substituent is C$_1$–C$_4$alkyl, or C$_2$–C$_4$alkenyl.

10. The method of claim 5 wherein said 5α reductase inhibitor compound of Formula II, R$^4$ is hydrogen or methyl and R$^5$ is hydrogen or methyl.

11. The method of claim 5 wherein said 5α reductase inhibitor compound of Formula II, R$^6$ and R$^7$ are selected from unsubstituted or substituted aryloxy, C$_{1-10}$ alkyloxy or C$_{1-10}$ alkylthio.

12. The method of claim 5 wherein Formula II, the C$_1$–C$_2$ carbon-carbon bond is a single bond, R$^4$ is methyl, R$^5$ is methyl, R$^7$ is selected from unsubstituted or substituted aryloxy, and R$^6$ is hydrogen.

13. The method of claim 5 wherein said Formula II:
one of R$^6$ and R$^7$ is selected from the group consisting of hydrogen and methyl, and the other is selected from the group consisting of:
(b) cyano;
(c) fluoro;
(e) OH;
(g) C$_{1-10}$ alkyl-X—; or C$_{1-10}$ alkyl-X—, where alkyl can be substituted with aryl, and wherein aryl in turn can be substituted with 1–2 of halo or C$_{1-6}$alkyl;
(h) C$_{2-10}$ alkenyl-X—;
(i) aryl-X—;
(j) heteroaryl-X—, wherein heteroaryl is a 5 or 6 membered heteroaromatic ring containing 1–2 ring nitrogen atoms; wherein the aryl in (i) and heteroaryl in (j) can be unsubstituted or substituted with one to two of:
x) halo; cyano; nitro; trihalomethyl; trihalomethoxy; C$_{1-6}$ alkyl; aryl; C$_{1-6}$ alkylsulfonyl; C$_{1-6}$ alkylarylsulfonamino;
xi) —NR$_b$R$_c$; R$_b$—C(O)—N(R$_c$)—; wherein R$_b$ and R$_c$ are independently H, C$_{1-6}$ alkyl, aryl, or arylC$_{1-6}$alkyl; wherein the alkyl moiety can be substituted with 1–3 of: halo; C$_{1-4}$alkoxy; or trifluoromethyl; and the aryl moiety can be substituted with 1–3 of: halo; C$_{1-4}$alkyl; C$_{1-4}$ alkoxy; or trifluoromethyl;
xii) a heterocyclic group, which is a 5 membered aromatic ring, containing one ring nitrogen atom, or one ring oxygen and one ring nitrogen atom; and
(k) wherein R$^6$ and R$^7$ taken together can be carbonyl oxygen; and wherein:

X is selected from the group consisting of:
—O—; —S(O)$_n$—; —CH(R$_e$)—; —C(O)—N(R$_e$)—*; —O—C(O)—N(R$_e$)—*;
wherein R$_e$ is H, C$_{1-3}$ alkyl, aryl, aryl C$_{1-3}$ alkyl;
wherein the asterisk (*) denotes the bond which is attached to the 16-position in Structure II; and n is zero or 2.

14. The method of claim 5 wherein said compound is selected from the group consisting of:
7β-ethyl-4-methyl-4-aza-cholest-5-en-3-one;
7β-ethyl-4-methyl-4-aza-cholestane-3-one;
7β-ethyl-4-aza-5α-cholestan-3-one;
7β-carboxymethyl-4-aza-cholest-5-en-3-one;
7β-carboxymethyl-4-aza-cholestan-3-one;
7β-propyl-4-methyl-4-aza-cholestan-5-en-3-one;
7β-propyl-4-methyl-4-aza-5α-cholestan-3-one;
7β-propyl-4-aza-5α-cholestan-3-one;
7β-methyl-4-aza-cholest-5-en-3-one;
7β-methyl-4-aza-cholestan-3-one;
4,7β-dimethyl-4-aza-cholest-5-en-3-one;
4,7β-dimethyl-4-aza-5α-cholestan-3-one;
4-methyl-4-aza-5α-cholestan-3,7-dione;
7β-acetoxy-4-methyl-4-aza-5α-cholestan-3-one;
7β-hydroxy-4-methyl-4-aza-5α-cholestane-3-one;
7β-methoxy-4-methyl-4-aza-5α-cholestane-3-one;
7β-hydroxymethyl-4-aza-5α-cholestane-3-one;
7β-bromomethyl-4-aza-5α-cholestane-3-one;
7β-chloromethyl-4-aza-5α-cholestane-3-one;
7β-fluoromethyl-4-aza-5α-cholestane-3-one;
7β-carboxy-4-aza-5α-cholestane-3-one;
7β-trifluoromethyl-4-aza-cholest-5-en-3-one;
7β-methoxy-4-methyl-4-aza-cholesta-5-en-3-one;
7β-cyclopropyloxy-4-methyl-4-aza-5α-cholestane-3-one;
7β-propylidene-4-methyl-4-aza-5α-cholestane-3-one;
7β-(2-ethyl)spiroethylene-4-methyl-4-aza-5α-cholestane-3-one;

7β-methyl-4-aza-5α-cholest-1-en-3-one;
4-aza-4,7β-dimethyl-5α-androstane-3,16-dione;
4-aza-4-methyl-5α-androstan-3,16-dione;
3-oxo-4-aza-4-methyl-16β-hydroxy-5α-androstane;
3-oxo-4-aza-4-methyl-16β-(benzylaminocarbonyloxy)-5α-androstane;
3-oxo-4-aza-4-methyl-16β-benzoylamino-5α-androstane;
3-oxo-4-aza-4-methyl-16β-methoxy-5α-androstane;
3-oxo-4-aza-4-methyl-16β-allyloxy-5α-androstane;
3-oxo-4-aza-4-methyl-16β-(n-propyloxy)-5α-androstane;
3-oxo-4-aza-4-methyl-16α-hydroxy-5α-androstane;
3-oxo-4-aza-4-methyl-16β-(phenoxy)-5α-androstane;
3-oxo-4-aza-7β-methyl-16β-(phenoxy)-5α-androst-1-ene;
3-oxo-4-aza-4-methyl-16α-methoxy-5α-androstane;
3-oxo-4-aza-4-methyl-16β-(4-chlorophenoxy)-5α-androstane;
3-oxo-4-aza-7β-methyl-16β-(4-chlorophenoxy)-5α-androst-1-ene;
3-oxo-4-aza-7β-methyl-16β-(4-chlorophenoxy)-5α-androstane;
3-oxo-4-aza-7β-methyl-16β-(3-chloro-4-methylphenoxy)-5α-androstane;
3-oxo-4-aza-7β-methyl-16β-(4-methylphenoxy)-5α-androstane;
3-oxo-4-aza-7β-methyl-16β-(4-methylphenoxy)-5α-androst-1-ene;
3-oxo-4-aza-7β-methyl-16β-[4-(1-pyrrolyl)phenoxy]-5α-androst-1-ene;
3-oxo-4-aza-4,7β-dimethyl-16β-hydroxy-5α-androstane;
3-oxo-4-aza-4,7β-dimethyl-16β-methoxy-5α-androstane;
3-oxo-4-aza-4,7β-dimethyl-16β-allyloxy-5α-androstane;
3-oxo-4-aza-4,7β-dimethyl-16β-(3,3-dimethylallyloxy)-5α-androstane;
3-oxo-4-aza-4,7β-dimethyl-16β-(n-propyloxy)-5α-androstane;
3-oxo-4-aza-4,7β-dimethyl-16β-(iso-pentoxy)-5α-androstane;
3-oxo-4-aza-4,16α-dimethyl-16β-hydroxy-5α-androstane;
3-oxo-4-aza-4,7β-dimethyl-16β-ethyloxy-5α-androstane;
3-oxo-4-aza-4,7β-dimethyl-16β-benzyloxy-5α-androstane;
3-oxo-4-aza-4,7β-dimethyl-16α-hydroxy-5α-androstane;
3-oxo-4-aza-4,7β-dimethyl-16β-methylthio-5α-androstane;
3-oxo-4-aza-4,7β-dimethyl-16β-(n-propylthio)-5α-androstane;
3-oxo-4-aza-4,7β-dimethyl-16β-fluoro-5α-androstane;
3-oxo-4-aza-4,7β-dimethyl-16β-cyano-5α-androstane;
3-oxo-4-aza-4-methyl-16β-(1-hexyl)-5α-androstane;
3-oxo-4-aza-4,7β-dimethyl-16β-(n-propyl)-5α-androstane;
3-oxo-4-aza-4,7β-dimethyl-16β-benzyl-5α-androstane;
3-oxo-4-aza-4,7β-dimethyl-16β-(4-chlorobenzyl)-5α-androstane;
3-oxo-4-aza-4,16α-dimethyl-16β-methoxy-5α-androstane;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(tert-butyloxy)-5α-androstane;
3-oxo-4-aza-4,7β-dimethyl-16β-(3-methyl-1-butyloxy)-5α-androstane;
3-oxo-4-aza-4,7β-dimethyl-16α-(n-propyloxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-ethylthio-5α-androstane;
3-oxo-4-aza-4,7β-dimethyl-16β-ethylsulfonyl-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-(3-pyridyloxy)-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-(2-pyrazinyloxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-(2-pyrimidinyloxy)-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
3-oxo-4-aza-4,7β-dimethyl-16β-(4-chlorophenoxy)-5α-androst-1-ene;
3-oxo-4-aza-4,7β-dimethyl-16-(4-chlorobenzylidene)-5α-androstane;
3-oxo-4-aza-4,7β-dimethyl-16-benzylidene-5α-androstane;
3-oxo-4-aza-4,7β-dimethyl-16-(4-methylbenzylidene)-5α-androstane;
3-oxo-4-aza-4,7β-dimethyl-16-(4-chlorobenzyl)-5α-androstane;
3-oxo-4-aza-4,7β-dimethyl-16-(4-methylbenzyl)-5α-androstane;
3-oxo-4-aza-4,7β-dimethyl-16-(3-pyridylmethyl)-5α-androstane;
3-oxo-4-aza-4,7β-dimethyl-16α-methanesulfonyl-5α-androstane;
3-oxo-4-aza-4,7β-dimethyl-16β-thiophenoxy-5α-androstane;
3-oxo-4-aza-4,7β-dimethyl-16β-(4-chlorothiophenoxy)-5α-androstane;
3-oxo-4-aza-4,7β-dimethyl-16β-(4-fluorothiophenoxy)-5α-androstane;
3-oxo-4-aza-4,7β-dimethyl-16β-(4-methylthiophenoxy)-5α-androstane;
3-oxo-4-aza-4,7β-dimethyl-16β-(4-methoxythiophenoxy)-5α-androstane;
3-oxo-4-aza-4,7β-dimethyl-16β-phenylsulfinyl-5α-androstane;

3-oxo-4-aza-4,7β-dimethyl-16β-phenylsulfonyl-5α-androstane;
3-oxo-4-aza-4,7β,16α-trimethyl-16β-(4-trifluoromethylphenoxy)-5α-androstane;
3-oxo-4-aza-4,7β,16α-trimethyl-16β-hydroxy-5α-androstane;
3-oxo-4-aza-4,7β,16α-trimethyl-16β-methoxy-5α-androstane;
pharmaceutically acceptable salts thereof.

15. The method of claim 14 wherein said 5α reductase inhibitor compound is selected from the group consisting of:
7β-ethyl-4-methyl-4-azacholestan-3-one;
7β-propyl-4-methyl-4-aza-5α-cholestan-3-one;
4,7β-dimethyl-4-aza-5α-cholestan-3-one;
3-oxo-4-aza-4,7β-dimethyl-16β-(4-cyanophenoxy)-5α-androstane;
3-oxo-4-aza-4,7β-dimethyl-16β-(3-cyanophenoxy)-5α-androstane;
3-oxo-4-aza-4,7β-dimethyl-16β-(4-nitrophenoxy)-5α-androstane;
3-oxo-4-aza-4,7β-dimethyl-16β-(1-naphthyloxy)-5α-androstane;
3-oxo-4-aza-4,7β-dimethyl-16β-(3-chloro-4-methylphenoxy)-5α-androstane;
3-oxo-4-aza-4,7β-dimethyl-16β-(4-methylphenoxy)-5α-androstane;
3-oxo-4-aza-4,7β-dimethyl-16β-(4-trifluoromethylphenoxy)-5α-androstane;
3-oxo-4-aza-4,7β-dimethyl-16β-(4-trifluoromethoxyphenoxy)-5α-androstane;
3-oxo-4-aza-4,7β-dimethyl-16β-(4-methylsulfonylphenoxy)-5α-androstane;
3-oxo-4-aza-4,7β-dimethyl-16β-[4-(4-tolylsulfonylamino)phenoxy]-5α-androstane;
3-oxo-4-aza-4,7β-dimethyl-16β-[(4-phenyl)phenoxy)-5α-androstane;
3-oxo-4-aza-4,7β-dimethyl-16β-(4-fluorophenoxy)-5α-androstane;
3-oxo-4-aza-4,7β-dimethyl-16β-[4-(5-oxazolyl)phenoxy]-5α-androstane;
3-oxo-4-aza-4,7β-dimethyl-16β-[4-(1-pyrryl)phenoxy]-5α-androstane;
3-oxo-4-aza-4,7β-dimethyl-16β-(4-aminophenoxy)-5α-androstane;
3-oxo-4-aza-4,7β-dimethyl-16β-(4-acetylaminophenoxy)-5α-androstane;
3-oxo-4-aza-4,7β-dimethyl-16β-(4-benzoylaminophenoxy)-5α-androstane;
3-oxo-4-aza-4,7β-dimethyl-16β-(4-chlorophenoxy)-5α-androstane;
3-oxo-4-aza-4,7β-dimethyl-16β-(phenoxy)-5α-androstane;
3-oxo-4-aza-4,7β-dimethyl-16β-(2-chlorophenoxy)-5α-androstane;
3-oxo-4-aza-4,7β-dimethyl-16β-(3-chlorophenoxy)-5α-androstane;
and the pharmaceutically acceptable salts thereof.

16. The method of claim 15 wherein said 5α reductase inhibitor compound is selected from:
4,7β-dimethyl-4-aza-5α-cholestan-3-one;
3-oxo-4-aza-4,7β-dimethyl-16β-(4-chlorophenoxy)-5α-androstane, 3-oxo-4-aza-4,7β-dimethyl-16β-[4-(1-pyrryl)phenoxy]-5α-androstane,
or a pharmaceutically acceptable salt thereof.

17. The method of claim 1 wherein said antibacterial is selected from the group consisting of: aminoglycosides, amphenicols, ansamycins, beta-lactams, lincosamides, macrolides, polypeptides, tetracyclines, 2,4,-diaminopyrimidines, nitrofurans, quinolones, sulfonamides, and sulfones, or mixture thereof.

18. The method of claim 1 wherein said antibacterial is selected from the group consisting of:
(a) aminoglycosides, including amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, streptonicozid, tobramycin;

(b) amphenicols, including azidamfenicol, chloramphenicol, chloramphenicol palmitate, chloramphenicol pantothenate, florfenicol, thiamphenicol;

(c) ansamycins, including rifamide, rifampin, rifamycin SV, rifaximin;

(d) beta-lactams, including imipenem, cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, pivcefalexin, cefbuperazone, cefmetazole, cefminox, cefotetan, cefoxitin, aztreonam, carumonam, tigemonam, flomoxef, moxolactam, amidinocillin, amidinocillin pivoxil, amoxicillin, ampicillin, apalcillin, aspoxicillin, azidocillin, azlocillin, bacampicillin, benzylpenicillinic acid, benzylpenicillin sodium, carbenicillin, carfecillin sodium, carindacillin, clometocillin, cloxacillin, cyclacillin, dicloxacillin, diphenicillin sodium, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, talampicillin, temocillin, ticarcillin;

(e) lincosamides, including clindamycin, lincomycin;

(f) macrolides, including azithromycin, carbomycin, clarithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin;

(g) polypeptides, including amphomycin, bacitracin, capreomycin, colistin, enduracidin, enviomycin, fusafungine, gramicidin(s), gramicidin S, mikamycin, polymyxin, polymyxin B-methanesulfonic acid, pristinamycin, ristocetin, teicoplanin, thiostrepton, tuberactinomycin, tyrocidine, tyrothricin, vancomycin, viomycin, viomycin pantothenate, virginiamycin, zinc bacitracin;

(h) tetracyclines, including apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin, tetracycline;

(i) 2,4-diaminopyrimidines, including brodimoprim, tetroxoprim, trimethoprim;

(j) nitrofurans, including furaltadone, furazolium chloride, nifuradene, nifuratel, nifurfoline, nifurpirinol, nifurprazine, nifurtoinol, nitrofurantoin;

(k) quinolones, including amifloxacin, cinoxacin, ciprofloxacin, difloxacin, enoxacin, fleroxacin, flumequine, lomefloxacin, miloxacin, nalidixic acid, norfloxacin, ofloxacin, oxolinic acid, pefloxacin, pipemidic acid, piromidic acid, rosoxacin, temafloxacin, tosufloxacin, $OPC_{725\,1}$ fluoroquinolone (Otsuka);

(l) sulfonamides, including acetyl sulfamethoxypyrazine, acetyl sulfisoxazole, azosulfamide, benzylsulfamide, chloramine-B, chloramine-T, dichloramine-T, formosulfathiazole, N-formylsulfisomidine, N-beta-D-glucosylsulfanilamide, mafenide, 4'-(methylsulfamoyl)sulfanilanilide, p-nitrosulfathiazole, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, N-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole;

(m) sulfones, including acedapsone, acediasulfone, acetosulfone sodium, dapsone, diathymosulfone, glucosulfone sodium, solasulfone, succisulfone, sulfanilic acid, p-sulfanilylbenzylamine, p,p'-sulfonyldianiline-N,N'-digalactoside, sulfoxone sodium, thiazolsulfone; and (n) the group consisting of: cycloserine, mupirocin, tuberin, clofoctol, hexedine, methenamine, methenamine anhydromethylene-citrate, methenamine hippurate, methenamine mandelate, methenamine sulfosalicylate, nitroxoline, xibornol, benzoyl peroxide, or mixtures thereof.

19. The method of claim 18 wherein said antibacterial is clindamycin, OPC7251 (Otsuka) fluoroquinolone or erythromycin.

20. The method of claim 1 wherein said keratolytic agent is selected from the group consisting of algestone acetophenide, azelaic acid, benzoyl peroxide, benzoyl peroxide/erythromycin, cyoctol, dichloroacetic acid, metronidazole, motretinide, resorcinol, salicylic acid, sulfur, tetroquinone, alpha-hydroxy acids, glycolic acid, and mixtures thereof.

21. The method of claim 20 wherein said keratolytic agent is benzoyl peroxide, benzoyl peroxide/erythromycin, or salicylic acid.

22. The method of claim 1 wherein said anti-inflammatory is selected from the group consisting of:
aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, glucocorticoids or mixture thereof.

23. The method of claim 1 wherein said anti-inflammatory is selected from the group consisting of:

(a) aminoarylcarboxylic acid derivatives, including enfenamic acid, etofenamate, flufenamic acid, isonixin, meclofenamic acid, mefenamic acid, niflumic acid, talniflumate, terofenamate, tolfenamic acid;

(b) arylacetic acid derivatives, including acemetacin, alclofenac, amfenac, bufexamac, cinmetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin, zomepirac;

(c) arylbutyric acid derivatives, including bumadizon, butibufen, fenbufen, xenbucin;

(d) arylcarboxylic acids, including clidanac, ketorolac, tinoridine;

(e) arylpropionic acid derivatives, including alminoprofen, benoxaprofen, bucloxic acid, carprofen, fenoprofen, flunoxaprofen, flurbiprofen, ibuprofen, ibuproxam, indoprofen, ketoprofen, loxoprofen, miroprofen, naproxen, oxaprozm, piketoprofen, pirprofen, pranoprofen, protizinic acid, suprofen, tiaprofenic acid;

(f) pyrazoles, including difenamizole, epirizole;

(g) pyrazolones, including apazone, benzpiperylon, feprazone, mofebutazone, morazone, oxyphenbutazone, phenylbutazone, pipebuzone, propyphenazone, ramifenazone, suxibuzone, thiazolinobutazone;

(h) salicylic acid derivatives, including acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salicylsulfuric acid, salsalate, sulfasalazine;

(i) one member selected from the group consisting of: epsilon-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, tenidap;

(j) glucocorticoids, including 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethaxsone, diflorasone, diflucortolone, defluprednate, enoxolone, fluazacort, flucloronide, flumethasone, flunisolide, fluocinolone acetonide, fluocinonide, fluocortin butyl, fluocortolone flujorometholone, fluperolone acetate, fluprednidene acetat, fluprednisolone, flurandrenolide, formocortal, halcinonide, halometasone, halopredone acetate, hydrocortamate, hydrocortisone, hydrocortisone acetate, hydrocortisone phosphate, hydrocortisone 21-sodium succinate, hydrocortisone tebutate, maziprednone, medrysone, meprednisone, methylprednisonole, mometasone furoate, paramethasone prednicarbate, prednisolone, prednisolone 21-diethylaminoacetate, prednisolone sodium phosphate, prednisolone sodium succinate, prednisolone sodium 21-m-sulfobenzoate, prednisoione 21-stearoylglycolate, prednisolone tebutate, prednisolone 21-trimethylacetate, prednisone, prednival, prednylidene, prednylidene 21-diethylaminoacetate, tixocotrol, triamcinolone, triamcinolone acetonide, triamcinolone benetonide, triamcinolone hexacetonide, or mixture thereof.

24. The method of claim 23 wherein said anti-inflammatory is prednisone.

25. A method of inhibiting acne-related 5α-reductase or the isozymes thereof, comprising the step of administering to a person in need of such inhibition a therapeutically effective amount each of the 5α-reductase inhibitor and at least one member selected from an antibacterial, keratolytic and anti-inflammatory agent.

26. A pharmaceutical composition comprising a pharmaceutically acceptable carrier and a therapeutically effective amount of a 5α-reductase inhibitor and at least one member selected from an antibacterial, keratolytic and anti-inflammatory agent.

27. The pharmaceutical composition of claim 26 wherein said 5α-reductase inhibitor is a 5α-reductase 1 inhibitor.

28. The pharmaceutical composition of claim 26 wherein said 5α-reductase inhibitor is a 5α-reductase 2 inhibitor.

29. The pharmaceutical composition of claim 26 wherein said 5α-reductase inhibitor is a mixture of 5α-reductase 1 and 2 inhibitors.

30. The pharmaceutical composition of claim 27 wherein the 5α-reductase 1 inhibitor is selected from the group consisting of: 4,7-β-dimethyl-4-aza-5α-cholestan-3-one; 3-oxo-4-aza-4,7β-dimethyl-16β-(4-chlorophenoxy]-5α-androstane, 3-oxo-4-aza-4,7β-dimethyl-16β-[4-[1-pyrrolyl)phenoxy)-5α-androstane, or a pharmaceutically acceptable salt thereof.

31. A pharmaceutical composition comprising a pharmaceutically acceptable carrier and a therapeutically effective amount of a 5α-reductase 1 inhibitor, as defined in claim 3, and at least one member selected from an antibacterial, keratolytic and anti-inflammatory agent.

* * * * *

UNITED STATES PATENT AND TRADEMARK OFFICE
CERTIFICATE OF CORRECTION

PATENT NO. : 5,543,417

DATED : Aug. 6, 1996

INVENTOR(S) : J. Waldstreicher

It is certified that error appears in the above-identified patent and that said Letters Patent is hereby corrected as shown below:

In Claim 14, at Column 100, line 46, delete "7β-propyl-4-methyl-4-aza-cholestan-5-en" and substitute therefor -- 7β-propyl-4-methyl-4-aza-cholest-5-en --.

Signed and Sealed this

Third Day of December, 1996

Attest:

BRUCE LEHMAN

*Attesting Officer*    *Commissioner of Patents and Trademarks*